US012741133B2

(12) United States Patent
Benza et al.

(10) Patent No.: US 12,741,133 B2

(45) Date of Patent: Sep. 22, 2026

(54) BIATRIAL CATHETERS AND CARDIOPULMONARY SUPPORT SYSTEMS

(71) Applicant: Ohio State Innovation Foundation, Columbus, OH (US)

(72) Inventors: Raymond Benza, Columbus, OH (US); Ryan C. Brune, Bexley, OH (US); Rebecca R. Vanderpool, Columbus, OH (US); Walter G. Vancleave, III, Pickerington, OH (US)

(73) Assignee: Ohio State Innovation Foundation, Columbus, OH (US)

( * ) Notice: Subject to any disclaimer, the term of this patent is extended or adjusted under 35 U.S.C. 154(b) by 330 days.

(21) Appl. No.: 18/279,927

(22) PCT Filed: Mar. 4, 2022

(86) PCT No.: PCT/US2022/018917

§ 371 (c)(1),
(2) Date: Sep. 1, 2023

(87) PCT Pub. No.: WO2022/187625

PCT Pub. Date: Sep. 9, 2022

(65) Prior Publication Data

US 2024/0139495 A1 May 2, 2024

Related U.S. Application Data

(60) Provisional application No. 63/157,127, filed on Mar. 5, 2021.

(51) Int. Cl.

| | |
|---|---|
| ***A61B 17/00*** | (2006.01) |
| ***A61M 25/00*** | (2006.01) |

(Continued)

(52) U.S. Cl.

CPC ...... *A61M 60/117* (2021.01); *A61M 25/0026* (2013.01); *A61M 25/005* (2013.01);

(Continued)

(58) Field of Classification Search

CPC ............ A61M 60/117; A61M 25/0026; A61M 25/005; A61M 25/007; A61M 2025/0002;

(Continued)

(56) References Cited

U.S. PATENT DOCUMENTS

| | | | | |
|---|---|---|---|---|
| 5,738,649 A | | 4/1998 | Macoviak | |
| 5,861,003 A | * | 1/1999 | Latson | A61B 17/0057 606/213 |

(Continued)

FOREIGN PATENT DOCUMENTS

| | | | | |
|---|---|---|---|---|
| CN | 107684659 A | | 2/2018 | |
| WO | 2005/037345 A2 | | 4/2005 | |
| WO | WO-2019241522 A1 | * | 12/2019 | A61M 1/3659 |

OTHER PUBLICATIONS

European Patent Office. Communication pursuant to Rule 164(1) EPC. Issued in EP Application No. 22764137.0 on Jan. 8, 2025. 13 pages.

(Continued)

*Primary Examiner* — Carl H Layno
*Assistant Examiner* — Anh-Khoa N Dinh
(74) *Attorney, Agent, or Firm* — Meunier Carlin & Curfman LLC

(57) ABSTRACT

A catheter comprising: a first portion having a proximal end and a distal end, a second portion having a proximal end and a distal end, and a third portion having a proximal end and a distal end; wherein the first and the second portions comprise an outflow lumen; wherein the third portion comprises an inflow lumen and the outflow lumen; wherein the first portion has a helical portion having a first length and (Continued)

extending from the distal end of the first portion toward the distal end of the second portion; and wherein the catheter is configured to be inserted into a patient body such that the first portion penetrates an atrial septum to extend into a left atrium to assist with systemic perfusion with oxygenated blood. Also disclosed are septum fixation and docking assemblies, and the systems are using the same.

20 Claims, 26 Drawing Sheets

(51) Int. Cl.
*A61M 25/04* (2006.01)
*A61M 60/109* (2021.01)
*A61M 60/117* (2021.01)

(52) U.S. Cl.
CPC ... *A61M 25/007* (2013.01); *A61M 2025/0002* (2013.01); *A61M 2205/02* (2013.01); *A61M 2205/3327* (2013.01); *A61M 2205/3331* (2013.01); *A61M 2210/125* (2013.01)

(58) Field of Classification Search
CPC ...... A61M 2205/02; A61M 2205/3327; A61M 2205/3331; A61M 2210/125; A61M 1/3659; A61M 1/3666; A61M 60/109; A61M 60/279; A61M 60/38; A61M 1/1698; A61M 2207/00; A61M 2209/088; A61M 25/0041; A61M 25/0045; A61M 25/0068; A61M 25/04; A61M 2025/0031; A61B 17/0057; A61B 2017/00243; A61B 2017/00477; A61B 2017/00606; A61B 2017/00876; A61B 2017/3425
See application file for complete search history.

(56) References Cited

U.S. PATENT DOCUMENTS

| | | | | |
|---|---|---|---|---|
| 5,976,103 | A | 11/1999 | Martin | |
| 2006/0247575 | A1* | 11/2006 | Cartledge | A61M 25/10 604/102.01 |
| 2010/0030165 | A1* | 2/2010 | Takagi | A61L 29/085 604/525 |
| 2012/0143141 | A1 | 6/2012 | Verkaik et al. | |
| 2012/0179033 | A1* | 7/2012 | Merhi | A61F 2/013 604/529 |
| 2016/0022896 | A1 | 1/2016 | Burkhoff | |
| 2018/0333162 | A1* | 11/2018 | Saab | A61M 25/0108 |
| 2020/0155803 | A1* | 5/2020 | Caton | A61M 25/0113 |
| 2020/0376183 | A1* | 12/2020 | El Katerji | G06N 3/045 |

OTHER PUBLICATIONS

European Patent Office. Extended European search report. Issued in EP Application No. 22764137.0 on Mar. 31, 2025. 11 pages.
Aggarwal V, Einhorn BN, Cohen HA. Current status of percutaneous right ventricular assist devices: First-in-man use of a novel dual lumen cannula. Catheter Cardiovasc Interv 2016;88:390-6.
Akay B, Reoma JL, Camboni D, et al. In-parallel artificial lung attachment at high flows in normal and pulmonary hypertension models. Ann Thorac Surg 2010;90:259-65.
Antaki JF, Dennis TJ, Konishi H, et al. An improved left ventricular cannula for chronic dynamic blood pump support. Artif Organs 1995;19:671-5.
Avriel A, Klement AH, Johnson SR, de Perrot M, Granton J. Impact of Left Ventricular Diastolic Dysfunction on Lung Transplantation Outcome in Patients With Pulmonary Arterial Hypertension. Am J Transplant 2017;17:2705-11.
Barst RJ, Chung L, Zamanian RT, Turner M, McGoon MD. Functional class improvement and 3-year survival outcomes in patients with pulmonary arterial hypertension in the REVEAL Registry. Chest 2013;144:160-8.
Bartolome SD, Torres F. Severe pulmonary arterial hypertension: stratification of medical therapies, mechanical support, and lung transplantation. Heart Fail Rev 2016;21:347-56.
Belohlavek J, Rohn V, Jansa P, et al. Veno-arterial ECMO in severe acute right ventricular failure with pulmonary obstructive hemodynamic pattern. J Invasive Cardiol 2010;22:365-9.
Benza RL, Gomberg-Maitland M, Miller DP, et al. The REVEAL Registry risk score calculator in patients newly diagnosed with pulmonary arterial hypertension. Chest 2012;141:354-62.
Benza RL, Miller DP, Gomberg-Maitland M, et al. Predicting survival in pulmonary arterial hypertension: insights from the Registry to Evaluate Early and Long-Term Pulmonary Arterial Hypertension Disease Management (REVEAL). Circulation 2010;122:164-72.
Bonnet S, Provencher S. Shear Stress Maladaptation in Pulmonary Arterial Hypertension. An Ageless Concept. Am J Respir Crit Care Med 2016;193:1331-2.
Camboni D, Akay B, Pohlmann JR, et al. Veno-venous extracorporeal membrane oxygenation with interatrial shunting: a novel approach to lung transplantation for patients in right ventricular failure. J Thorac Cardiovasc Surg 2011;141:537-42, 42 el.
Camboni D, Akay B, Sassalos P, et al. Use of venovenous extracorporeal membrane oxygenation and an atrial septostomy for pulmonary and right ventricular failure. Ann Thorac Surg 2011;91:144-9.
Chen H, Shiboski SC, Golden JA, et al. Impact of the lung allocation score on lung transplantation for pulmonary arterial hypertension. Am J Respir Crit Care Med 2009;180:468-74.
Chkourko HS, Guerrero-Serna G, Lin X, et al. Remodeling of mechanical junctions and of microtubule- associated proteins accompany cardiac connexin43 lateralization. Heart Rhythm 2012;9:1133-40.e6.
Cook KE, Perlman CE, Seipelt R, Backer CL, Mavroudis C, Mockrost LF. Hemodynamic and gastransfer properties of a compliant thoracic artificial lung. Asaio J 2005;51:404-11.
Dai DF, Swanson PE, Krieger EV, Liou IW, Carithers RL, Yeh MM. Congestive hepatic fibrosis score: a novel histologic assessment of clinical severity. Mod Pathol 2014;27:1552-8.
Dalton HJ, Garcia-Filion P, Holubkov R, et al. Association of bleeding and thrombosis with outcome in extracorporeal life support. Pediatr Crit Care Med 2015;16:167-74.
Farber HW, Miller DP, Poms AD, et al. Five-Year outcomes of patients enrolled in the REVEAL Registry. Chest 2015;148:1043-54.
Ferreira A, Boston JR, Antaki Jf. A control system for rotary blood pumps based on suction detection. IEEE Trans Biomed Eng 2009;56:656-65.
Frenckner B, Broman M, Broomé M. Position of draining venous cannula in extracorporeal membrane oxygenation for respiratory and respiratory/circulatory support in adult patients. Crit Care 2018;22:163.
Frost AE, Badesch DB, Miller DP, Benza RL, Meltzer LA, McGoon MD. Evaluation of the predictive value of a clinical worsening definition using 2-year outcomes in patients with pulmonary arterial hypertension: a REVEAL Registry analysis. Chest 2013;144:1521-9.
Gomberg-Maitland M, Glassner-Kolmin C, Watson S, et al. Survival in pulmonary arterial hypertension patients awaiting lung transplantation. The Journal of heart and lung transplantation : the official publication of the International Society for Heart Transplantation 2013;32:1179-86.
Gregoric ID, Chandra D, Myers TJ, Scheinin SA, Loyalka P, Kar B. Extracorporeal membrane oxygenation as a bridge to emergency heart-lung transplantation in a patient with idiopathic pulmonary arterial hypertension. The Journal of heart and lung transplantation : the official publication of the International Society for Heart Transplantation 2008;27:466-8.
Gu S, Hu H, Dong H. Systematic Review of the Economic Burden of Pulmonary Arterial Hypertension. Pharmacoeconomics 2016;34:533-50.

(56) References Cited

OTHER PUBLICATIONS

Gwak KW, Antaki JF, Paden BE, Kang B. Safety-enhanced optimal control of turbodynamic blood pumps. Artif Organs 2011;35:725-32.
Herlihy JP, Loyalka P, Jayaraman G, Kar B, Gregoric ID. Extracorporeal membrane oxygenation using the TandemHeart System's catheters. Tex Heart Inst J 2009;36:337-41.
Hoeper MM, Tudorache I, Kuhn C, et al. Extracorporeal membrane oxygenation watershed. Circulation 2014;130:864-5.
Hoopes CW, Gurley JC, Zwischenberger JB, Diaz-Guzman E. Mechanical support for pulmonary veno- occlusive disease: combined atrial septostomy and venovenous extracorporeal membrane oxygenation. Semin Thorac Cardiovasc Surg 2012;24:232-4.
Ireland NPHCotUa. Consensus statement on the management of pulmonary hypertension in clinical practice in the UK and Ireland. Thorax 2008; 63 Suppl 2:ii1-ii41.
Kerrigan JP, Yamazaki K, Meyer RK, et al. High-resolution fluorescent particle-tracking flow visualization within an intraventricular axial flow left ventricular assist device. Artif Organs 1996;20:534-40.
Kim J, Sato H, Griffith GW, Cook KE. Cardiac Output During High Afterload Artificial Lung Attachment. ASAIO Journal 2009;55:73-7.
Knight DS, Steeden JA, Moledina S, Jones A, Coghlan JG, Muthurangu V. Left ventricular diastolic dysfunction in pulmonary hypertension predicts functional capacity and clinical worsening: a tissue phase mapping study. Journal of cardiovascular magnetic resonance : official journal of the Society for Cardiovascular Magnetic Resonance 2015;17:116.
Krack A, Sharma R, Figulla HR, Anker SD. The importance of the gastrointestinal system in the pathogenesis of heart failure. European heart journal 2005;26:2368-74.
Lai A, Demarest CT, Do-Nguyen CC, et al. 72-Hour in vivo evaluation of nitric oxide generating artificial lung gas exchange fibers in sheep. Acta Biomater 2019;90:122-31.
Lamb KM, Hirose H, Cavarocchi NC. Preparation and technical considerations for percutaneous cannulation for veno-arterial extracorporeal membrane oxygenation. J Card Surg 2013;28:190-2.
Lange PE, Nürnberg JH, Sievers HH, Onnasch DGW, Bernhard A, Heintzen PH. Response of the right ventricle to progressive pressure loading in pigs. Basic research in cardiology 1985;80:436-44.
López-Meseguer M, Quezada CA, Ramon MA, et al. Lung and heart-lung transplantation in pulmonary arterial hypertension. PLoS One 2017;12:e0187811.
McGillicuddy JW, Cook KE, Lambert MB, et al. In Parallel Artificial Lung Returns Pulmonary Resistance to Normal in Chronic Lung Disease Model. ASAIO Journal 2003;49:170.
McLaughlin VV, Archer SL, Badesch DB, et al. ACCF/AHA 2009 expert consensus document on pulmonary hypertension a report of the American College of Cardiology Foundation Task Force on Expert Consensus Documents and the American Heart Association developed in collaboration with the American College of Chest Physicians; American Thoracic Society, Inc.; and the Pulmonary Hypertension Association. Journal of the American College of Cardiology 2009;53:1573-619.
Megalla S, Holtzman D, Aronow WS, et al. Predictors of cardiac hepatopathy in patients with right heart failure. MED Sci Monit 2011;17:CR537-41.
Menon PG, Antaki JF, Undar A, Pekkan K. Aortic outflow cannula tip design and orientation impacts cerebral perfusion during pediatric cardiopulmonary bypass procedures. Ann Biomed Eng 2013;41:2588-602.
Mullens W, Abrahams Z, Francis GS, et al. Importance of venous congestion for worsening of renal function in advanced decompensated heart failure. Journal of the American College of Cardiology 2009;53:589-96.
Myers RP, Cerini R, Sayegh R, et al. Cardiac hepatopathy: clinical, hemodynamic, and histologic characteristics and correlations. Hepatology 2003;37:393-400.
Niebauer J, Volk HD, Kemp M, et al. Endotoxin and immune activation in chronic heart failure: a prospective cohort study. Lancet 1999;353:1838-42.
Ohman JW, Vemuri C, Prasad S, Silvestry SC, Jim J, Geraghty PJ. The effect of extremity vascular complications on the outcomes of cardiac support device recipients. J Vasc Surg 2014;59:1622-7.
Pohlmann JR, Akay B, Camboni D, Koch KL, Mervak BM, Cook Ke. A Low Mortality Model of Chronic Pulmonary Hypertension in Sheep. Journal of Surgical Research 2012;175:44-8.
Punnoose L, Burkhoff D, Rich S, Horn EM. Right ventricular assist device in end-stage pulmonary arterial hypertension: insights from a computational model of the cardiovascular system. Prog Cardiovasc Dis 2012;55:234-43.e2.
Rajdev S, Benza R, Misra V. Use of Tandem Heart as a temporary hemodynamic support option for severe pulmonary artery hypertension complicated by cardiogenic shock. J Invasive Cardiol 2007;19:E226-9.
Ranchoux B, Bigorgne A, Hautefort A, et al. Gut-Lung Connection in Pulmonary Arterial Hypertension. Am J Respir Cell Mol Biol 2017;56:402-5.
Ravichandran AK, Baran DA, Stelling K, Cowger JA, Salerno CT. Outcomes with the Tandem Protek Duo Dual-Lumen Percutaneous Right Ventricular Assist Device. Asaio J 2018;64:570-2.
Rosenzweig EB, Brodie D, Abrams DC, Agerstrand CL, Bacchetta M. Extracorporeal membrane oxygenation as a novel bridging strategy for acute right heart failure in group 1 pulmonary arterial hypertension. ASAIO J 2014;60:129-33.
Rosenzweig EB, Chicotka S, Bacchetta M. Right ventricular assist device use in ventricular failure due to pulmonary arterial hypertension: Lessons learned. The Journal of heart and lung transplantation : the official publication of the International Society for Heart Transplantation 2016;35:1272-4.
Roussel A, Al-Attar N, Khaliel F, et al. Arterial vascular complications in peripheral extracorporeal membrane oxygenation support: a review of techniques and outcomes. Future Cardiol 2013;9:489-95.
Rupprecht L, Lunz D, Philipp A, Lubnow M, Schmid C. Pitfalls in percutaneous ECMO cannulation. Heart Lung Vessel 2015;7:320-6.
Sato H, Griffith GW, Hall CM, et al. Seven-day artificial lung testing in an in-parallel configuration. Ann Thorac Surg 2007;84:988-94.
Sato H, Hall CM, Griffith GW, et al. Large Animal Model of Chronic Pulmonary Hypertension. ASAIO J 2008;54:396-400.
Sato H, Hall CM, Lafayette NG, et al. Thirty-day in-parallel artificial lung testing in sheep. Ann Thorac Surg 2007;84:1136-43; discussion 43.
Schäfer M, Kheyfets VO, Schroeder JD, et al. Main pulmonary arterial wall shear stress correlates with invasive hemodynamics and stiffness in pulmonary hypertension. Pulm Circ 2016;6:37-45.
Schewe RE, Scipione CN, Koch KL, Cook KE. In-parallel attachment of a low-resistance compliant thoracic artificial lung under rest and simulated exercise. Ann Thorac Surg 2012;94:1688-94.
Schmack B, Weymann A, Popov AF, et al. Concurrent Left Ventricular Assist Device (LVAD) Implantation and Percutaneous Temporary RVAD Support via CardiacAssist Protek-Duo TandemHeart to Preempt Right Heart Failure. Med Sci Monit Basic Res 2016;22:53-7.
Schmitto JD, Burkhoff D, Avsar M, et al. Two axial-flow Synergy Micro-Pumps as a biventricular assist device in an ovine animal model. The Journal of heart and lung transplantation : the official publication of the International Society for Heart Transplantation 2012;31:1223-9.
Seeto RK, Fenn B, Rockey DC. Ischemic hepatitis: clinical presentation and pathogenesis. Am J Med 2000;109:109-13.
Shu F, Parks R, Maholtz J, Ash S, Antaki JF. Multimodal flow visualization and optimization of pneumatic blood pump for sorbent hemodialysis system. Artif Organs 2009;33:334-45.
Simaan M, Ferreira A, Chen S, Antaki J. A dynamical state space representation and performance analysis of a feedback-controlled rotary left ventricular assist device. IEEE Transactions on Control Systems Technology 2009; 17:15-28.
Skoog DJ, Pohlmann JR, Demos DS, et al. Fourteen Day In Vivo Testing of a Compliant Thoracic Artificial Lung. Asaio J 2017;63:644-9.

(56) References Cited

OTHER PUBLICATIONS

Srivastava MC, Ramani GV, Garcia JP, Griffith BP, Uber PA, Park MH. Veno-venous extracorporeal membrane oxygenation bridging to pharmacotherapy in pulmonary arterial hypertensive crisis. J Heart Lung Transplant 2010;29:811-3.

Sztrymf B, Souza R, Bertoletti L, et al. Prognostic factors of acute heart failure in patients with pulmonary arterial hypertension. Eur Respir J 2010;35:1286-93.

Thenappan T, Shah SJ, Rich S, Gomberg-Maitland M. A USA-based registry for pulmonary arterial hypertension: 1982-2006. Eur Respir J 2007;30:1103-10.

Toomasian JM, Schreiner RJ, Meyer DE, et al. A polymethylpentene fiber gas exchanger for long-term extracorporeal life support. ASAIO J 2005;51:390-7.

Tudorache I, Sommer W, Kuhn C, et al. Lung transplantation for severe pulmonary hypertension-awake extracorporeal membrane oxygenation for postoperative left ventricular remodelling. Transplantation 2015;99:451-8.

Ukita R, Wu K, Lin X, et al. Zwitterionic poly-carboxybetaine coating reduces artificial lung thrombosis in sheep and rabbits. Acta Biomater 2019;92:71-81.

Wang Y, Loghmanpour N, Vandenberghe S, et al. Simulation of dilated heart failure with continuous flow circulatory support. PloS one 2014;9:e85234.

Yang F, Kormos RL, Antaki JF. High-speed visualization of disturbed pathlines in axial flow ventricular assist device under pulsatile conditions. J Thorac Cardiovasc Surg 2015;150:938-44.

Zamanian RT, Kudelko KT, Sung YK, Perez VJ, Liu J, Spiekerkoetter E. Current clinical management of pulmonary arterial hypertension. Circ Res 2014;115:131-47.

Drakos, Stavros G., et al. “Bridge to recovery: understanding the disconnect between clinical and biological outcomes.” Circulation 126.2 (2012): 230-241.

Hoganson, David M., et al. “Paracorporeal lung assist devices as a bridge to recovery or lung transplantation in neonates and young children.” The Journal of thoracic and cardiovascular surgery 147.1 (2014): 420-427.

International Searching Authority (ISA/US). International Search Report and Written Opinion. PCT Application No. PCT/US2022/018917. Issued on Jun. 30, 2022. 10 pages.

* cited by examiner

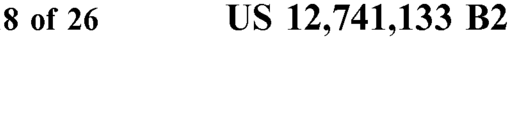
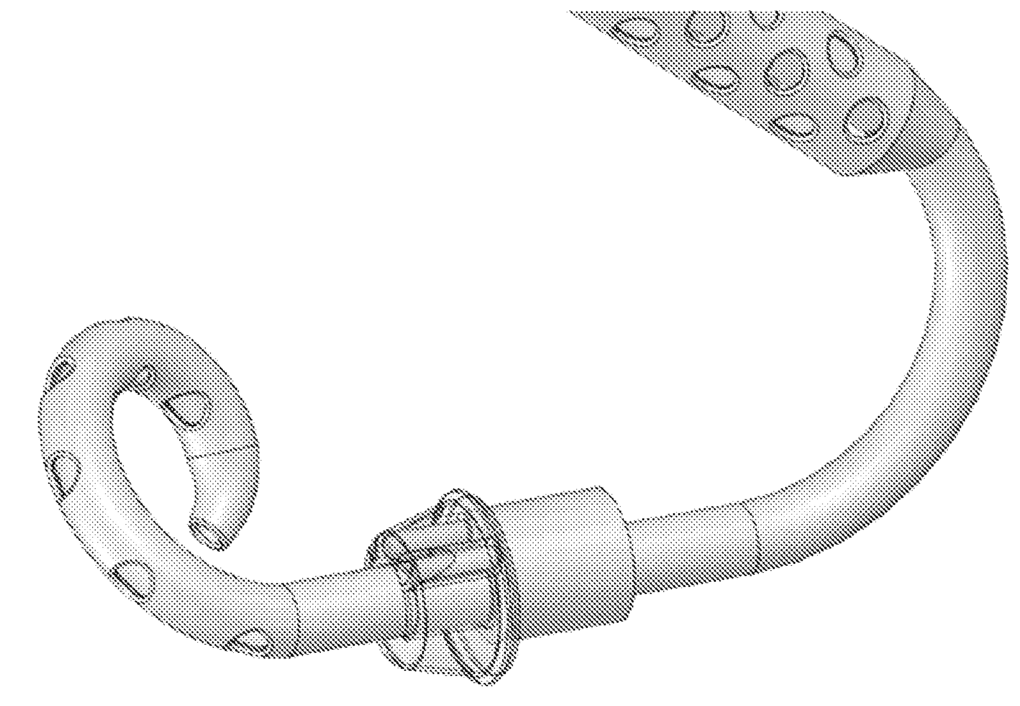
FIG.11A
FIG.11B
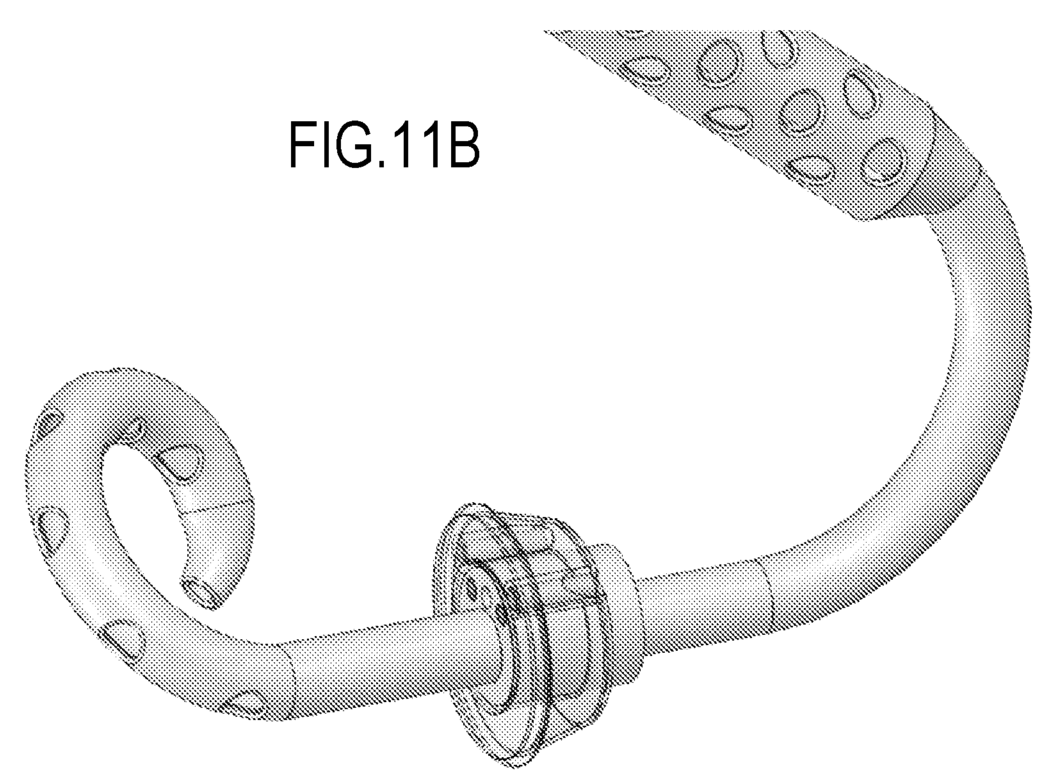

BIATRIAL CATHETERS AND CARDIOPULMONARY SUPPORT SYSTEMS

CROSS-REFERENCE TO RELATED APPLICATIONS

This application is a national stage application filed under 35 U.S.C. § 371 of PCT/US2022/018917, filed Mar. 4, 2022, which claims the benefit of U.S. Provisional Application No. 63/157,127 filed Mar. 5, 2021, the content of which is incorporated herein by reference in its entirety.

FIELD

This application relates generally to catheters for a cardiopulmonary support system in pulmonary hypertension, systems comprising such catheters, and methods of making and using the same.

BACKGROUND

It is commonly known that pulmonary arterial hypertension (PAH) is a devastating and progressive disease with a median life expectancy of 2.8 years if not treated. This disease is characterized by elevated pulmonary arterial pressure (PAP) and pulmonary vascular resistance (PVR) that can lead to devastating right ventricular (RV) failure and death. In the last two decades, new medical therapies have offered help in preventing disease progression; but even with optimal medical therapy, the 5-year survival is only 64.3%. The advent of easy-to-use oral therapies has driven a national trend of delayed referrals to expert centers. In turn, this has resulted in decreased and delayed utilization of life-saving parenteral prostacyclin.

Consequently, when they arrive at the expert centers, many PHA patients are presented in the advanced stages of right heart failure (RHF), including cardiogenic shock. For patients eligible for a lung transplant, the scarcity of donor organs, combined with the acuity of patients' illness from delayed treatment, long waiting list times, and intrinsic inequities in the lung transplant allocation system, have resulted in high mortality rates among patients waiting for a transplant. Thus, finding an optimal treatment for PAH-related RHF is of paramount importance.

PAH-related RHF affects all organ systems, particularly in the ICU setting, in which the consequences on the liver, kidneys, and gut are often catastrophic. Several lines of evidence suggest that elevated venous pressure with chronic congestion is particularly damaging to these organs. Malperfusion and congestion alter bowel wall permeability and may cause translocation of bacteria and endotoxins into the circulation, causing systemic inflammatory response or sepsis, common contributors to death in PAH patients with RHF. Therefore, contemporary consensus statements declare, "In patients with RHF refractory to treatment, mechanical support should be considered in candidates for lung transplantation (bridge to transplant) and, occasionally, in patients with a treatable cause of RHF or in hitherto treatment-naïve patients (bridge to recovery)." (Circulation. 20212; 126; 230-241; J. Thorac. Cardiovasc. Surg. 2014 January 147(1); 420-6), This alludes to emergent extracorporeal membrane oxygenation (ECMO) or other right-sided mechanical support for PAH-related RHF.

However, the currently known systems supporting PAH-related RHF have serious drawbacks. Veno-arterial (VA) ECMO is the most often utilized mechanical support approach for PAH with refractory RHF. This treatment involves removing deoxygenated blood from the right atrium (RA), introducing oxygen extracorporeally, and then delivering oxygenated blood systemically via femoral arteries. This is the "standard" ECMO circuit, which attempts to unload the RV by "bypassing" it. However, VA ECMO is still associated with a high level of procedural- and time-dependent morbidity, particularly when placed emergently. This configuration is also characterized by opposing blood flows in the aorta, one coming from the left ventricle the other from the ECMO system. In patients with femoral veno-arterial ECMO support, the lower body is supplied by blood originating from the ECMO and the upper body by blood coming from the heart. While ECMO safely maintains lower body oxygenation, upper body oxygenation, including the brain and heart, particularly the RV, can be significantly impaired as blood from the left heart often carries low oxygen content.

Thus, despite unloading the RV, the myocardium can remain ischemic and be difficult to recover in a PAH patient. This, combined with the difficulties mentioned above and prolonged waiting times for lung transplant, makes ECMO a precarious "bridge to transplant" support system. In those patients not eligible for a transplant or without a readily treatable etiology for RV decompensation (i.e., tachydysrhythmias), these short-term technologies offer limited help in prolonging life (i.e., bridge to recovery). Furthermore, the prolonged ECMO support presents a myriad of complications, including vascular damage and ischemia to the lower extremities: due to the large size of the catheter obstructing distal flow, catheter migration, and catheter repositioning needed to prevent hypoxia of the upper body (Harlequin syndrome).

Other short-term mechanical support systems, including the Protek Duo system (TandemLife/LivaNova, Pittsburgh, PA) and the RP Impella (Abiomed, Danvers, MA), are also known to be used to directly support the RV, particularly in the setting of an RV infarction or RHF related to durable left ventricular assist devices. The latter can unload the failing RV using a catheter that removes deoxygenated blood from the inferior vena cava and delivers blood directly to the PA. The former uses a dual lumen catheter that removes blood from the RA and, through an extracorporeal impeller pump and oxygenator, delivers blood directly back to the PA. However, these RV-support techniques can also have harmful limitations in patients with severe PAH, including aggravation of pulmonary vascular remodeling, pulmonary bleeding, and pulmonary edema in patients with coexistent left ventricular diastolic dysfunction. This latter phenomenon is a significant and common problem seen following lung transplants in many PAH patients because of chronic underloading of the left ventricle (LV). Thus, these devices often fail to appropriately fill the LV, leading to significant hypoxemia, systemic hypotension, poor tissue perfusion, lactic acidosis, worsening shock, and eventual end-organ failure.

Additional durable mechanical circulatory support devices designed for the LV (LVADs) in the RV configuration were also reported. These systems, similar to centrally placed ECMO, require surgical sternotomy and prolonged cardiopulmonary bypass times, which are often poorly tolerated by PAH patients. They can also result in significant PA damage and hemorrhage, similar to short-term RV mechanical support systems, resulting in premature demise. Even in the best of circumstances, the modalities mentioned above cannot provide long-term support. In fact, most nonsurgical systems are labeled only for periods of up to 1-2 weeks. These methods are also prone to catheter dislodgement—with even the most minimal movement, which can cause immediate catastrophic changes in hemodynamics and vascular injury. Consequently, patients are mostly bedridden, fostering significant physical deconditioning and psychological demise.

In light of the limitations mentioned above of existing support therapies, there is clearly a critical and immediate need for an innovative long-term right ventricular assist system. Such a system must provide two essential functions: effectively offloading the failing RV, promoting systemic perfusion with oxygenated blood without causing pulmonary edema, and preserving cognitive function. Adding this technology to the medical armamentarium would provide the necessary time for therapeutic treatment of the underlying disease and the ability to ambulate and rehabilitate without causing vascular injury. The first integral step in developing such a system is designing an innovative catheter that truly bypasses the RV, allowing recovery while at the same time supporting the systemic circulation and facilitation of medical treatment of the primary disease. These needs and others are at least partially satisfied by the present disclosure.

SUMMARY

Some aspects of the present disclosure relate to medical devices. In some aspects, disclosed herein is a catheter comprising: a first portion having a proximal end and a distal end, a second portion having a proximal end and a distal end, and a third portion having a proximal end and a distal end; wherein the first and the second portions comprise an outflow lumen; wherein the third portion comprises an inflow lumen and the outflow lumen; wherein the first portion has a helical portion having a first length and extending from the distal end of the first portion toward the distal end of the second portion; and wherein the catheter is configured to be inserted into a patient body such that the first portion penetrates an atrial septum to extend into a left atrium to assist with systemic perfusion with oxygenated blood.

Also disclosed are aspects wherein the inflow lumen has an elongated tubular body having a proximal end and a distal end and has a first diameter and configured to withdraw oxygen-depleted blood from a patient; and the outflow lumen has an elongated tubular body having a proximal end, a distal end and has a second diameter and configured to deliver oxygen-rich blood to the patient; wherein the first diameter is greater than the second diameter; wherein at least a portion of the elongated tubular body of the outflow lumen is disposed within at least a portion of the elongated tubular body of the inflow lumen; and wherein the distal end of the outflow lumen extends beyond the distal end of the inflow lumen.

In still further aspects, the helical portion of the first portion comprises a first plurality of fenestrations configured to prevent jet impingement on an endocardial surface of the left atrium and pulmonary veins.

In still further aspects, the catheter disclosed herein comprises an auxiliary member positioned radially outward of the distal end of the second portion and wherein the auxiliary member is configured to removably attach the catheter to the atrium septum.

Yet in still further aspects, the third portion of the disclosed herein catheters can comprise a portion having a second plurality of fenestrations, wherein the portion having the second plurality of fenestrations abuts the distal end of the third portion and has a third length.

Also disclosed herein is an atrial septal fixation and docking assembly comprising: an atrial member having a predetermined length, a first portion and a second portion; wherein the atrial member has a crimped profile having a first diameter and an expanded profile having a second diameter, wherein the second diameter is greater than the first diameter; wherein when the atrial member is inserted into the atrial septum to form an aperture of a predetermined dimension in the atrial septum, the first portion is fixated to a left side of the atrial septum, and the second portion is fixated to a right side of the atrial septum, wherein the atrial member encapsulates the aperture such that there is substantially no change in the predetermined dimension of the aperture for a predetermined period of time; and wherein the atrial member is configured to be delivered to the atrial septum in the crimped profile, and when the atrial member is removably fixated with the atrial septum, the atrial member is present in the expanded profile.

In still further aspects, the second portion of the atrial member can comprise one or more magnets.

Also disclosed herein are aspects directed to a long-term right ventricular assist system comprising a) any of the disclosed herein catheters; b) any of the disclosed herein atrial septal fixation and docking assemblies; and wherein the system is configured to effectively offload a failing right ventricular chamber and to promote systemic perfusion with oxygenated blood.

Also disclosed herein are methods comprising: a) inserting any of the disclosed herein atrial septal fixation and docking assemblies into an atrium septum; b) inserting any of the disclosed herein catheters, and reversibly locking the first portion of any of the disclosed herein catheters in the atrial septal fixation and docking assembly disclosed herein.

Additional aspects of the disclosure will be set forth, in part, in the detailed description, figures, and claims which follow, and in part will be derived from the detailed description or can be learned by practice of the invention. It is to be understood that both the foregoing general description and the following detailed description are exemplary and explanatory only and are not restrictive of the invention as disclosed.

BRIEF DESCRIPTION OF THE DRAWINGS

FIGS. 11A-11B show an exemplary fixation of an exemplary catheter to an exemplary atrial septal fixation and docking assembly in various aspects.

DETAILED DESCRIPTION

Figure 1:
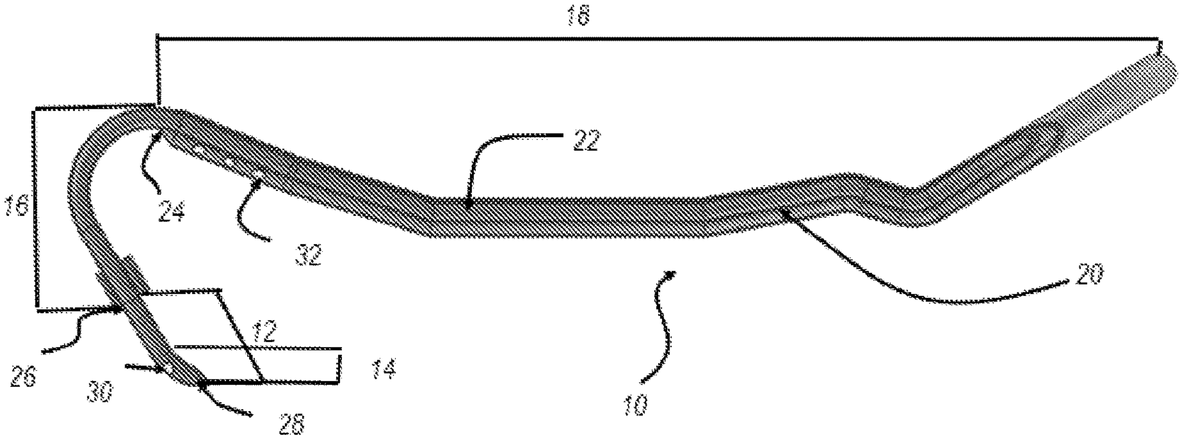
FIG. 1 is a cross-sectional view of an exemplary catheter in one aspect.

The present invention can be understood more readily by reference to the following detailed description, examples, drawings, and claims, and their previous and following description. However, before the present articles, systems, and/or methods are disclosed and described, it is to be understood that this invention is not limited to the specific or exemplary aspects of articles, systems, and/or methods disclosed unless otherwise specified, as such can, of course, vary. It is also to be understood that the terminology used herein is for the purpose of describing particular aspects only and is not intended to be limiting.

The following description of the invention is provided as an enabling teaching of the invention in its best, currently known aspect. To this end, those skilled in the relevant art will recognize and appreciate that many changes can be made to the various aspects of the invention described herein while still obtaining the beneficial results of the present invention. It will also be apparent that some of the desired benefits of the present invention can be obtained by selecting some of the features of the present invention without utilizing other features. Accordingly, those of ordinary skill in the pertinent art will recognize that many modifications and adaptations to the present invention are possible and may even be desirable in certain circumstances and are a part of the present invention. Thus, the following description is again provided as illustrative of the principles of the present invention and not in limitation thereof.

Definitions

As used in this application and in the claims, the singular forms "a," "an," and "the" include the plural forms unless the context clearly dictates otherwise. Thus, for example, reference to a "fenestration" includes aspects having two or more such fenestrations unless the context clearly indicates otherwise.

The term "comprising" and variations thereof as used herein is used synonymously with the term "including" and variations thereof and are open, non-limiting terms. Although the terms "comprising" and "including" have been used herein to describe various examples, the terms "consisting essentially of" and "consisting of" can be used in place of "comprising" and "including" to provide for more specific examples of the invention and are also disclosed. Other than in the examples, or where otherwise noted, all numbers expressing quantities of ingredients, reaction conditions, and so forth used in the specification and claims are to be understood at the very least and not as an attempt to limit the application of the doctrine of equivalents to the scope of the claims, to be construed in light of the number of significant digits and ordinary rounding approaches.

For the terms "for example," "exemplary," and "such as," and grammatical equivalences thereof, the phrase "and without limitation" is understood to follow unless explicitly stated otherwise. It is further understood that the term "exemplary" as used herein means "an example of" and is not intended to convey an indication of a preferred or ideal aspect."

Ranges can be expressed herein as from "about" one particular value and/or to "about" another particular value. When such a range is expressed, another aspect includes from the one particular value and/or to the other particular value. Similarly, when values are expressed as approximations, by use of the antecedent "about," it will be understood that the particular value forms another aspect. It should be further understood that the endpoints of each of the ranges are significant both in relation to the other endpoint, and independently of the other endpoint.

Similarly, when values are expressed as approximations, by use of the antecedent "about," it will be understood that the particular value forms another aspect. It will be further understood that the endpoints of each of the ranges are significant both in relation to the other endpoint and independently of the other endpoint. Unless stated otherwise, the term "about" means within 5% (e.g., within 2% or 1%) of the particular value modified by the term "about."

Throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6, etc., as well as individual numbers within that range, for example, 1, 2, 2.7, 3, 4, 5, 5.3, 6 and any whole and partial increments therebetween. This applies regardless of the breadth of the range.

As used herein, the terms "optional" or "optionally" mean that the subsequently described event or circumstance may or may not occur and that the description includes instances where said event or circumstance occurs and instances where it does not.

Further, the terms "coupled" and "associated" generally mean electrically, electromagnetically, and/or physically (e.g., mechanically or chemically) coupled or linked and do not exclude the presence of intermediate members between the coupled or associated items.

As used herein, the term or phrase "effective," "effective amount," or "conditions effective to" refers to such amount or condition that is capable of performing the function or property for which an effective amount or condition is expressed. As will be pointed out below, the exact amount or particular condition required will vary from one aspect to another, depending on recognized variables such as the materials employed and the processing conditions observed. Thus, it is not always possible to specify an exact "effective amount" or "condition effective to." However, it should be understood that an appropriate effective amount will be readily determined by one of ordinary skill in the art using only routine experimentation. Although the operations of exemplary aspects of the disclosed method may be described in a particular sequential order for convenient presentation, it should be understood that disclosed aspects can encompass an order of operations other than the particular sequential order disclosed. For example, operations described sequentially may, in some cases, be rearranged or performed concurrently. Further, descriptions and disclosures provided in association with one particular aspect are not limited to that aspect and may be applied to any aspect disclosed.

It will be understood that when a member is referred to as being "connected" or "coupled" to another member, it can be directly connected or coupled to the other member, or intervening members may be present. In contrast, when a member is referred to as being "directly connected" or "directly coupled" to another member, there are no intervening members present. Other words used to describe the relationship between members or layers should be interpreted in a like fashion (e.g., "between" versus "directly between," "adjacent" versus "directly adjacent," "on" versus "directly on").

As used herein, the term "and/or" includes any and all combinations of one or more of the associated listed items.

It will be understood that, although the terms "first," "second," etc., may be used herein to describe various members, components, regions, layers and/or sections, and/or steps. These members, components, regions, layers, and/or sections and/or steps should not be limited by these terms. These terms are only used to distinguish one member, component, region, layer, or section from another member, component, region, layer, section, or step. Thus, a first member, component, region, layer, section, or step discussed below could be termed a second member, component, region, layer, section, or step without departing from the teachings of example aspects.

Spatially relative terms, such as "beneath," "below," "lower," "above," "upper," and the like, may be used herein for ease of description to describe one member or feature's relationship to another member(s) or feature(s) as illustrated in the figures. It will be understood that the spatially relative terms are intended to encompass different orientations of the device in use or operation in addition to the orientation depicted in the figures. For example, if the device in the figures is turned over, members described as "below" or "beneath" other members or features would then be oriented "above" the other members or features. Thus, the term "below" can encompass both an orientation of above and below. The device may be otherwise oriented (rotated 90 degrees or at other orientations), and the spatially relative descriptors used herein are interpreted accordingly. Similarly, it is understood that the terms "proximal" and "distal" are only used to describe a spatially relative relationship between the disclosed members.

As used herein, the term "substantially" means that the subsequently described event or circumstance completely occurs or that the subsequently described event or circumstance generally, typically, or approximately occurs.

In other aspects, as used herein, the term "substantially free," when used in the context of a composition or component of a composition that is substantially absent, is intended to refer to an amount that is then about 1% by weight, e.g., less than about 0.5% by weight, less than about 0.1% by weight, less than about 0.05% by weight, or less than about 0.01% by weight of the stated material, based on the total weight of the composition.

Still further, the term "substantially" can in some aspects refer to at least about 80%, at least about 85%, at least about 90%, at least about 91%, at least about 92%, at least about 93%, at least about 94%, at least about 95%, at least about 96%, at least about 97%, at least about 98%, at least about 99%, or about 100% of the stated property, component, composition, or other condition for which substantially is used to characterize or otherwise quantify an amount or a specific property.

Still further, the term "close proximity" can in some aspects refer to a positioning of the specified member relative to a reference member and can be within about 0.01 mm from the reference member, within about 0.05 mm from the reference member, within about 0.1 mm from the reference member, within about 1 mm from the reference member, within about 5 mm from the reference member, or within about 10 mm from the reference member.

As used herein, the term "substantially," in, for example, the context "substantially identical" or "substantially similar" refers to a method or a system, or a component that is at least about 90%, at least about 91%, at least about 92%, at least about 93%, at least about 94%, at least about 95%, at least about 96%, at least about 97%, at least about 98%, at least about 99%, or about 100% by similar to the method, system, or the component it is compared to.

As used herein, the terms "substantially identical reference composition" or "substantially identical reference article" refer to a reference composition or article comprising substantially identical components in the absence of an inventive component. In another exemplary aspect, the term "substantially," in, for example, the context "substantially identical reference composition," refers to a reference composition comprising substantially identical components and wherein an inventive component is substituted with a common in the art component. For example, a substantially identical reference atrial septal fixation and docking assembly can comprise an atrial septal fixation and docking assembly comprising substantially identical components but without the presence of the at least one magnet as described.

Moreover, for the sake of simplicity, the attached figures may not show the various ways (readily discernable, based on this disclosure, by one of ordinary skill in the art) in which the disclosed system, method, and apparatus can be used in combination with other systems, methods, and apparatuses. Additionally, the description sometimes uses terms such as "produce" and "provide" to describe the disclosed method. These terms are high-level abstractions of the actual operations that can be performed. The actual operations that correspond to these terms can vary depending on the particular implementation and are, based on this disclosure, readily discernible by one of ordinary skill in the art.

Catheter and Atrial Septal Fixation and Docking Assembly

The disclosed herein aspects address a major challenge faced today in supporting patients with severe PAH: the lack of a short-term mechanical strategy to successfully manage severe, recurrent, or refractory RHF as a bridge to lung transplantation or medical optimization.

Figure 14A:
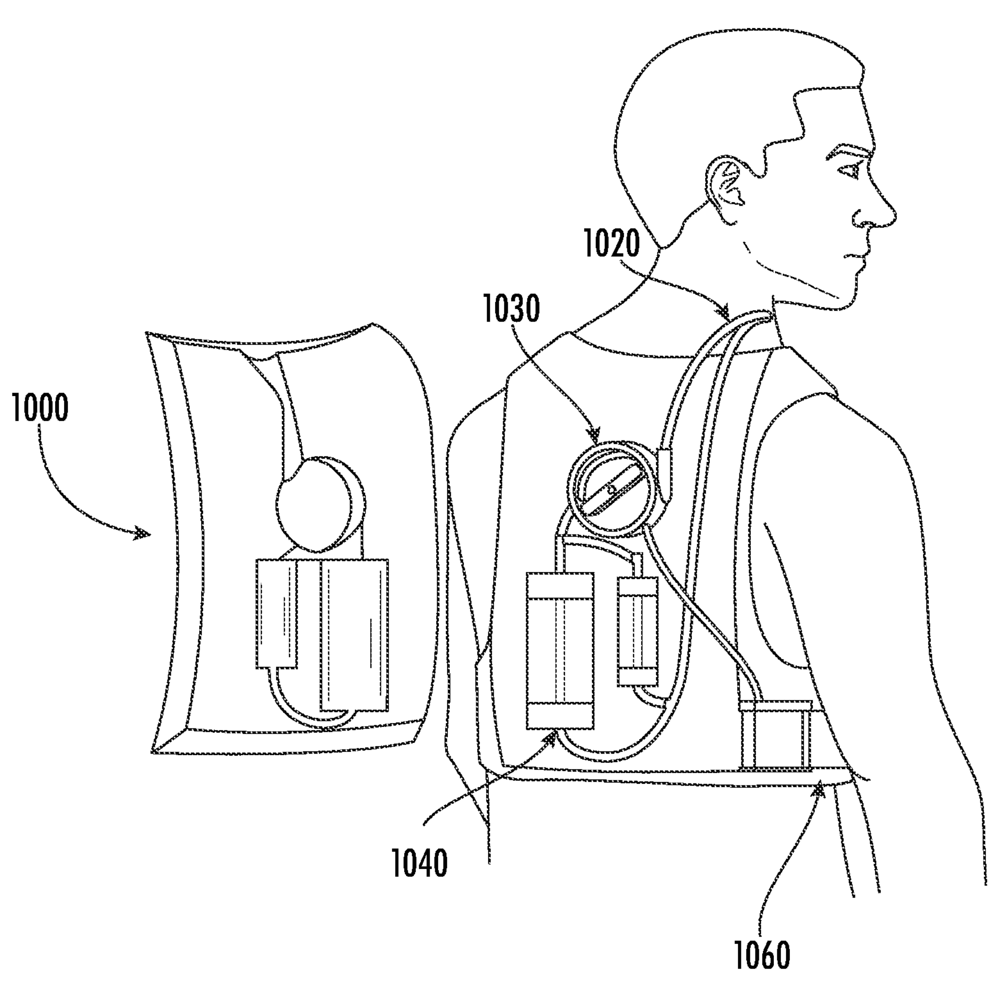
FIGS. 14A-14C show an exemplary mobile long-term right ventricular assist system in various aspects.
Figure 14B:
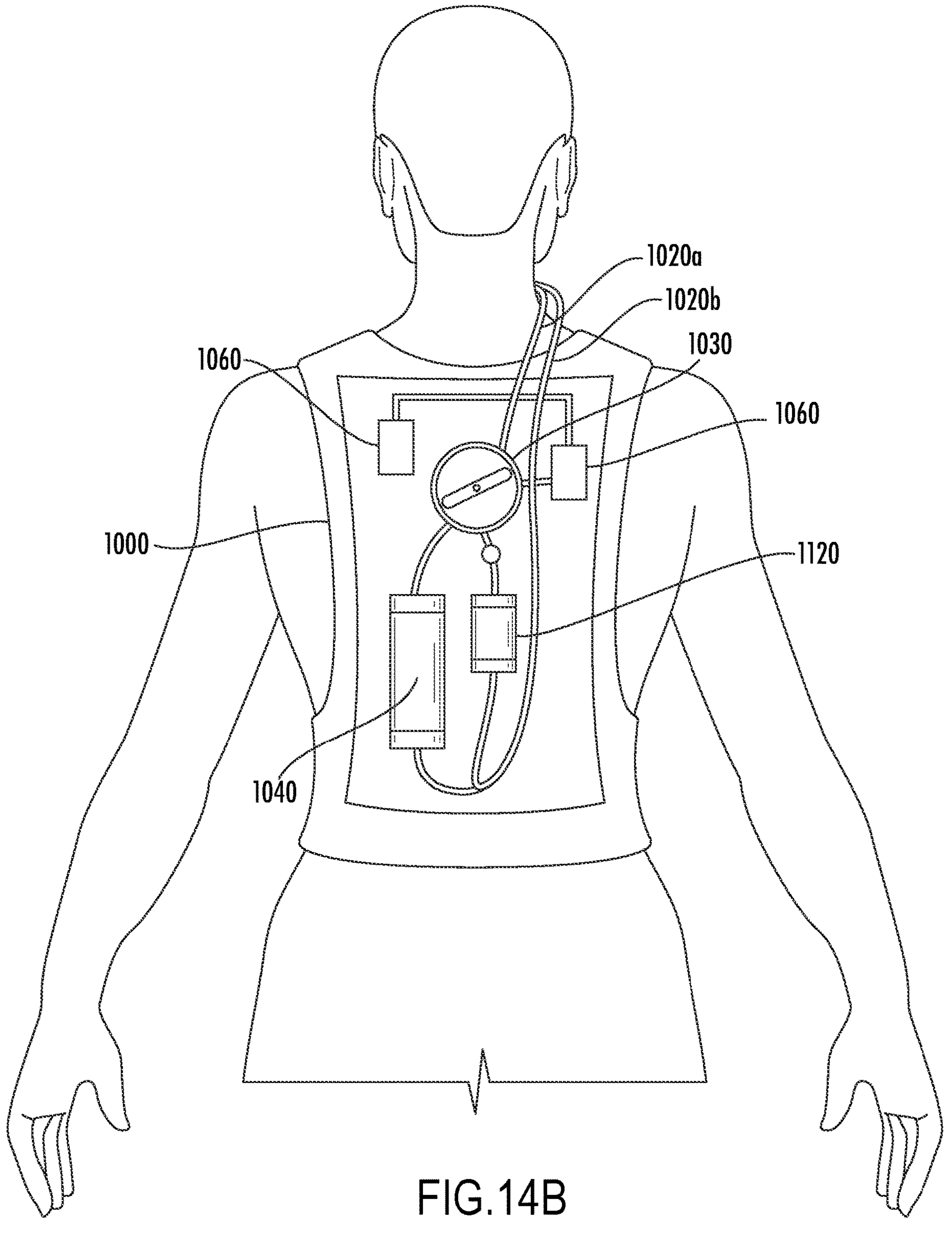
Figure 14C:
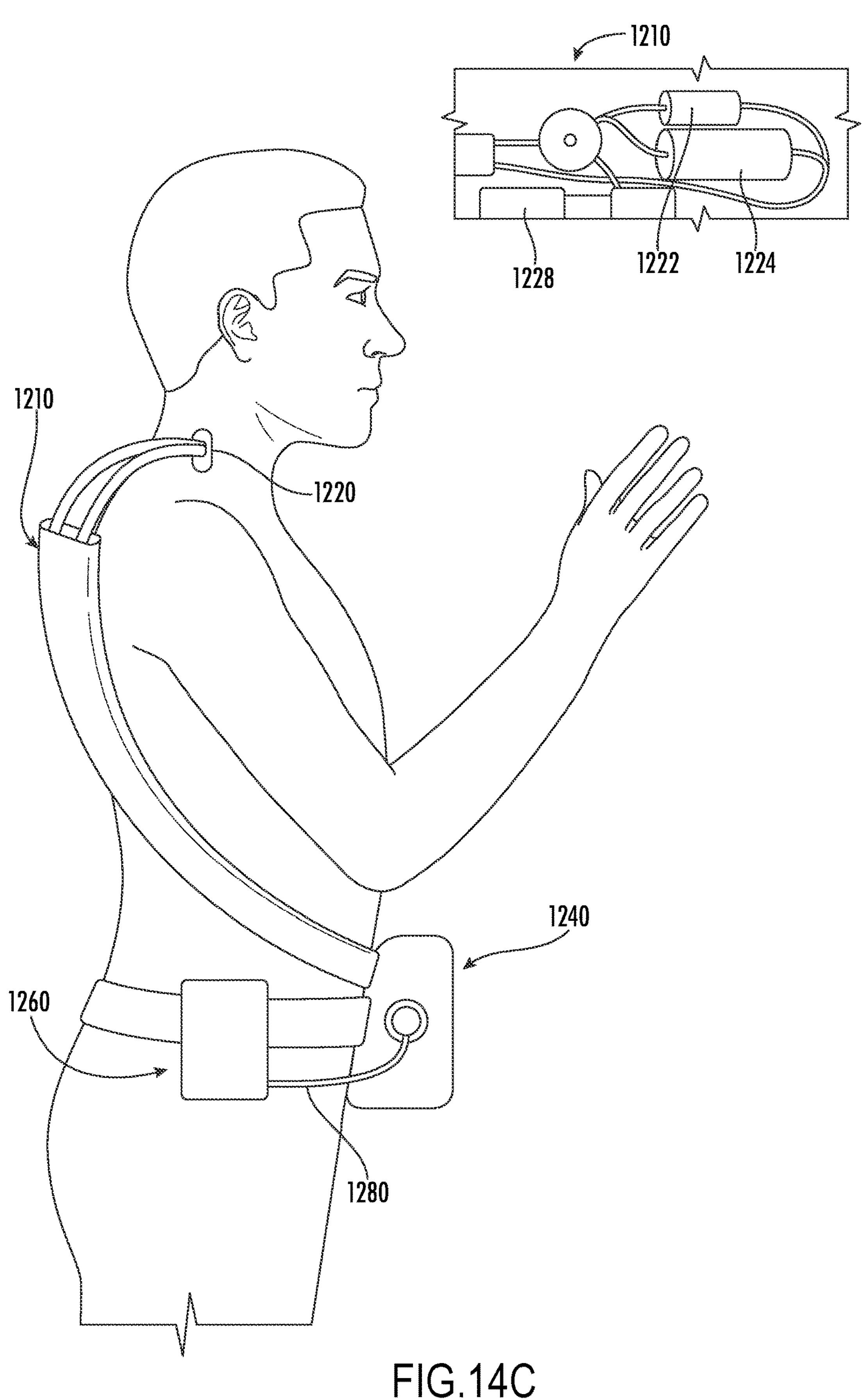

Disclosed herein are the aspects directed to a catheter and an atrial septal fixation and docking assembly that address one of the major challenges existing in supporting patients with severe PAH: the lack of a short-term mechanical strategy to successfully manage severe, recurrent, or refractory RHF as a bridge to lung transplantation, destination therapy or bridge to medical optimization. The aspects disclosed herein are further directed to a Mobile ECMO system (FIGS. 14A-14C). It is understood that the disclosed herein catheter can also be used in conjunction with a bedside mounted pump/oxygenator unit similar to a conventional ECMO configuration. In certain aspects, the disclosed herein catheter can also be called a PHope catheter.

In still further aspects and as discussed in detail below, the disclosed herein catheter can be inserted in the patient's body by any known in the art and applicable to the desired application methods. For example, and without limitations, in some aspects, the catheter can be inserted percutaneously via the internal jugular vein (left or right). In certain aspects, the insertion can be done using fluoroscopic guidance and standard echocardiographic windows. In yet further aspects, also the removal of the disclosed herein catheter can also be carried out in a similar fashion. The disclosed herein septal fixation and docking assemblies can be used to secure and protect the catheter at the level of the atrial septum. In yet other aspects, additional anchoring systems can be used to secure and protect the catheter as it exits the IJ skin site. It is understood that such an anchoring system can be any known in the art anchoring systems capable of achieving the desired result. For example, and without limitations, such systems can comprise skin fixation adhesive or Velcro® anchoring systems. Some of these systems as commercially available (for example, Baxter Health care GRIP-LOK Stabilization and Securement device).

It is understood that the catheters, fixation and docking assemblies, and further long-term right ventricular assist systems disclosed herein can help minimize cerebral and cardiac hypoxia seen commonly with traditional ECMO, potentiating RV recovery and patient cognition. Because the disclosed herein system is designed to bypass the pulmonary vasculature and offload the pulmonary arteries (PAs), shear stress and damage to the PAs can be avoided and thereby minimize complications such as pulmonary hemorrhage seen in prior configurations and allow for additional time to further treat these unloaded pulmonary arteries with oral, subcutaneous, parenteral or inhaled therapies.

The disclosed herein catheters and septal fixation and docking assemblies allow a stable and sealed trans-septal placement. Such a placement provides for translocation of RA blood to the LA: offloading the RV and pulmonary vasculature while maintaining (or enhancing) LV preload. It is understood that the former is paramount to facilitate reverse remodeling of the RV and pulmonary arterioles and allows greater flexibility to aggressively titrate parenteral prostacyclin or other medications as described above. This supplemental medical modification is key to allowing weaning strategies to treat naïve or minimally-treated patients in which shock is the presenting clinical scenario (i.e., bridge to recovery).

In still further aspects and as disclosed below, the catheters can further comprise sensoring systems that allow the blood flow to be adjusted to optimize RA and LA pressures to contemporaneously offload the RV and slowly retrain the noncompliant LV to accept more preload. In such aspects, the catheters disclosed herein can also minimize central venous congestion and pulmonary edema while providing sufficient cardiac output to restore end-organ and tissue perfusion.

It is understood that the disclosed catheters and systems allow dynamically regulate LA pressure and flow and thus minimize a well-known phenomenon compromising successful lung transplantation in PAH in that the small and "unconditioned" LVs of patients with severe PH are prone to developing diastolic dysfunction when exposed to a normal or high preload after transplantation. In the past, this under-recognized problem has frequently led to a vicious cycle of recalcitrant pulmonary edema, making it difficult and sometimes impossible to wean patients from the ventilator and thereby exposing these vulnerable patients to the associated risks of prolonged intensive care.

Still further, the aspects described below are directed to catheters that can be fixed in place and offer the opportunity for the patient to ambulate and optimize support time to allow prolonged use. In other words, by eliminating many of the complications of existing support systems, the disclosed catheters, docking assemblies, and long-term right ventricular assist systems allow the treatment of PAH by initiating support earlier and electively, prior to severe decompensation and for longer periods of time.

In other words, the disclosed catheters, docking assemblies, and long-term right ventricular assist systems allow tackling the limitations of prior modalities through its ability to: 1. Enable a novel therapeutic strategy that offloads the RV facilitating its recovery while monitoring pressure overload in the LA, minimizing complications of both pulmonary edema and LV venting; 2. Simplify insertion and removably using a venous percutaneous approach; 3. Provide appropriate catheter stability allowing for ambulation, extended use, and retrieval using a novel intra-atrial fixation system; 4. Avoid injury to the femoral artery and corresponding extremity, common to current VA ECMO and other conventional designs; 5. Minimize further injury to the pulmonary vasculature and permit favorable pulmonary vascular remodeling by reducing flow-mediated shear stress in the PAs; 6. Minimize hematological derangements by shifting flow away from the highly resistant pulmonary tree; and 7. Capitalize on upper body cannulation to allow ambulation and patient rehab. The disclosed herein catheters, docking assemblies, and long-term right ventricular assist systems can simplify and revolutionize the use of ECMO for PH and also make it possible for some patients to ambulate and possibly return home.

Again, as discussed above, the present disclosure is directed to a catheter that can be used to unload blood from the functioning right ventricle and to provide a left ventricle with oxygenized blood. In some aspects, the catheter described herein can comprise: a first portion having a proximal end and a distal end, a second portion having a proximal end and a distal end, and a third portion having a proximal end and a distal end; wherein the first and the second portions comprise an outflow lumen; wherein the third portion comprises an inflow lumen and the outflow lumen; wherein the first portion has a helical portion having a first length and extending from the distal end of the first portion toward the distal end of the second portion; and wherein the catheter is configured to be inserted into a patient body such that the first portion penetrates an atrial septum to extend into a left atrium to assist with systemic perfusion with oxygenated blood.

A partial cross-section of an exemplary catheter described in one aspect is shown in FIG. 1. The catheter 10 has a first portion 12 (shown partially), a second portion 16, and a third portion 18. The first portion has a distal end 28 and a proximal end 26. The second portion has a distal end 26 that is substantially identical to the proximal end of the first portion and a proximal end b that is substantially identical to a distal end of the third portion. The third portion also has a proximal end that is not shown as it can extend to the outside of a patient body and can be further coupled to additional systems or apparatuses if required. The first portion 12 of catheter 10 has a helical portion 14 that has a first length. It can be seen that the catheter further comprises an elongated tube of inflow lumen 20 and an elongated tube of outflow lumen 22. The third portion 18 of the catheter 10 comprises both the inflow lumen 20 and outflow lumen 22. However, the first 12 and the second 16 portions of the catheter only comprise the outflow lumen 22.

The elongated tubular body of the inflow lumen 20 also has a proximal end (not shown) and a distal end 24 (FIG. 1) that is substantially identical to the distal end of the third portion. In yet further aspects, the proximal end of the third portion can have a "y-type" configuration separating the inner (outflow) lumen oxygenated and outer (inflow) lumen deoxygenated blood. As disclosed below in more detail, the inflow lumen with deoxygenated blood can be further connected to a pump and oxygenator, and the inner (outflow) lumen extension will receive blood from the oxygenator. In certain aspects, the system can comprise more than one pump. Yet, in still further aspects, a dual-chamber pump can be used for both retrieving blood from the inlet cannula (inflow lumen) and pumping blood from the oxygenator back to the patient through the outlet cannula (outflow lumen).

The inflow lumen has a first diameter and is configured to withdraw oxygen-depleted blood from a patient. The elongated tubular body of the outflow lumen 22 has a proximal end (not shown) a portion of the distal end 28 (FIG. 1, shows a cut-off in the cross-section) that is substantially identical to the distal end of the first portion. The outflow lumen has a second diameter and is configured to deliver oxygen-rich blood to the patient. It is understood that in some aspects, the proximal end of the inflow lumen and the proximal end of the outflow lumen can be substantially the same location. However, described are also aspects where the proximal end of the inflow lumen extends beyond the proximal end of the outflow lumen or where the proximal end of the outflow lumen extends beyond the proximal end of the inflow lumen. It is further understood that both the proximal end of the inflow lumen and the proximal end of the outflow lumen extend to the outside of the patient's body, as described above.

In still further unlimiting aspects, the first diameter of the inflow lumen can be greater than the second diameter of the outflow lumen. In yet still further aspects, and as shown in FIG. 1, at least a portion of the elongated tubular body of the outflow lumen can be disposed within at least a portion of the elongated tubular body of the inflow lumen; such that the distal end of the outflow lumen extends beyond the distal end of the inflow lumen.

In still further aspects, the catheter disclosed herein can comprise the inflow lumen having a first outer layer defining an outer surface of the elongated tubular body of the inflow lumen of the catheter and a first inner layer defining an inner surface of the elongated tubular body of the inflow lumen. Yet in other aspects, the catheter disclosed herein can comprise the outflow lumen having a second outer layer defining an outer surface of the elongated tubular body, the outflow lumen, and a second inner layer defining an inner surface of the elongated tubular body of the outflow lumen. It is understood that in some aspects, the first outer layer, first inner layer, second outer layer, and the second inner layer can comprise the same material. While in yet other aspects, the first outer layer, first inner layer, second outer layer, and the second inner layer can comprise different materials. Yet in other aspects, for example, and without limitations, the first outer layer and the first inner layer can be the same or different. While in yet other aspects, the second outer layer and the second inner layer can be the same or different. Also disclosed are aspects where for example, the first outer layer is different from the second outer layer, while the first inner layer is substantially the same as the second outer layer. In such aspects, the second inner layer can be the same or different as well. It is understood that these examples are not limiting, and the layers can have any composition that is applicable for a specific purpose.

In some aspects, the first outer layer, the first inner layer, the second outer layer, and/or the second inner layer can comprise a polymeric material comprising a reinforced polyurethane, styrene-based elastomer, polyolefin-based elastomers (POE), polyethylene terephthalate (PET), polytetrafluoroethylene (PTFE), ethylene-vinyl acetate (EVA), fluorinated ethylene propylene (FEP), polyether block amide (PEBAX), or any combination thereof.

In yet still further aspects, any of the outer layers or inner layers can be lubricious. In such exemplary and unlimiting aspects, the first inner layer, the second outer layer, and/or the second inner layer can have a coefficient of friction less than about 0.5, less than about 0.4, less than about 0.3, less than about 0.2, or even less than about 0.1

In yet still further aspects, the catheter can further comprise a coating disposed at an outermost surface of the catheter. It is understood that the outermost surface of the catheter would be defined by the first outer layer in the third portion of the catheter and by the second outer layer in the second and the first portions of the catheter. In such aspects, the coating can be a hydrophilic coating. It is understood that in some aspects, the hydrophilic coating can be applied along an entire length of the catheter or just a portion of the catheter. Examples of suitable hydrophilic coatings include the Harmony™ Advanced Lubricity Coatings and other Advanced Hydrophilic Coatings available from SurModics, Inc., Eden Prairie, MN. DSM medical coatings (available from Koninklijke DSM N.V, Heerlen, the Netherlands), as well as other hydrophilic coatings (e.g., PTFE, polyethylene, polyvinylidene fluoride).

In still further aspects, the elongated tubular body of the outflow lumen can be positioned within at least a portion of the elongated tubular body of the inflow lumen such that a center of the outflow lumen is offset of a center of the inflow lumen. While in other aspects, the elongated tubular body of the outflow lumen is positioned within at least a portion of the elongated tubular body of the inflow lumen such that a center of the outflow lumen and a center of the inflow lumen substantially overlap.

Some of the exemplary aspects describing the positioning of the inflow and outflow lumens and their layers configurations are shown in FIGS. 2A-2D.

Figure 2A:
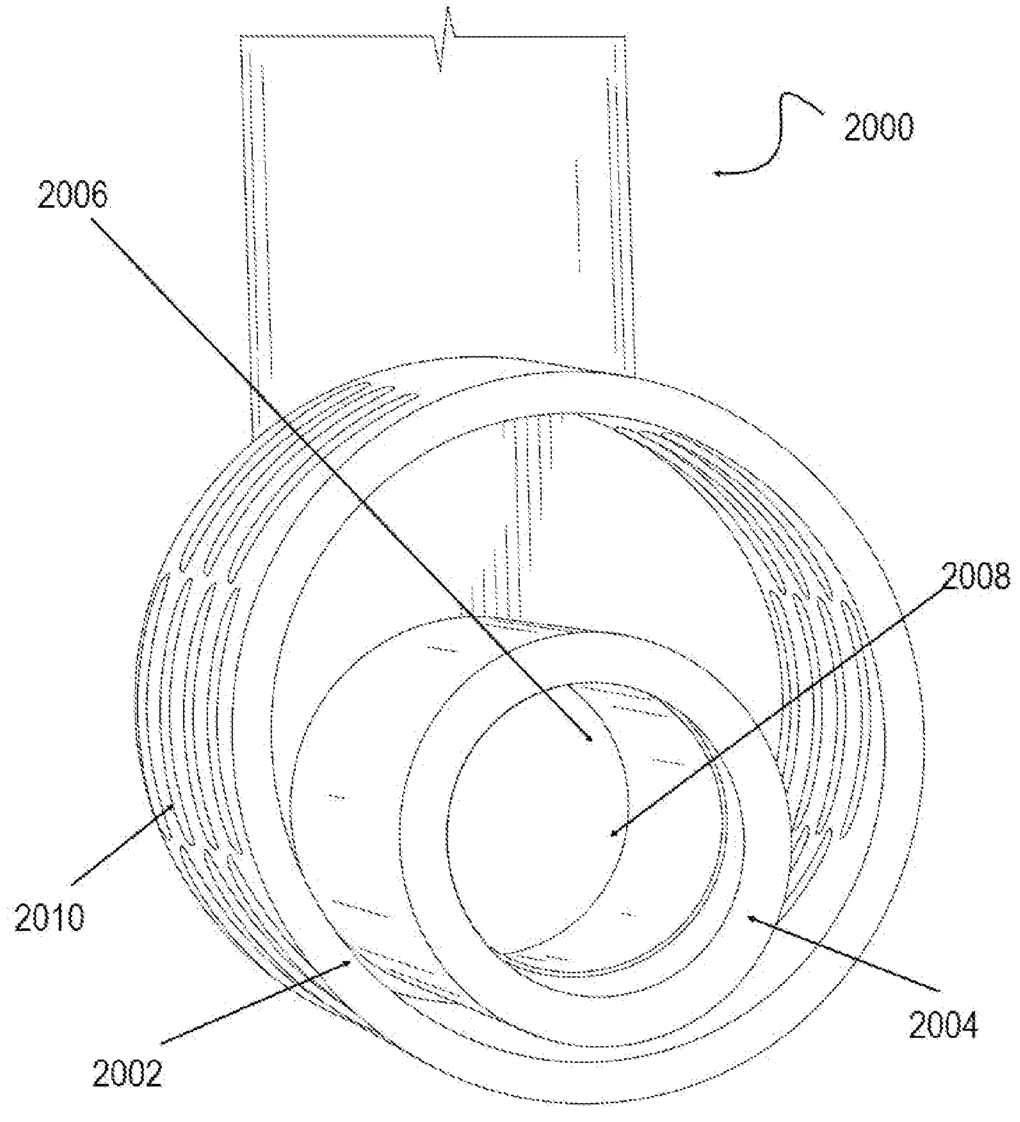
FIG. 2A-2D depict a cross-sectional view of an inflow lumen and an outflow lumen as they are positioned in a third portion of the example catheter in one aspect (FIG. 2 A); layer configurations of the catheter in various aspects (FIG. 2B-2D).

FIG. 2A shows a cross-sectional view of the third portion of the catheter 2000 where the elongated tube of the outflow lumen 2004 is positioned within the elongated tube of the inflow lumen 2002. In this exemplary and unlimiting aspect, a center 2008 of the outflow lumen 2004 is offset of a center 2006 of the inflow lumen 2002. In other words, in these aspects, the outflow lumen and inflow lumen are not concentric. However, it is understood that the aspects where the two lumens are concentric to each other along the entire length of the catheter or at least a portion of thereof are also disclosed (as shown, for example, in FIG. 2D)

In some aspects, the inflow and outflow lumens of the disclosed catheter can be positioned such that the outflow lumen can move unrestrictedly within the cavity of the inflow lumen, and its specific position within the cavity of the inflow lumen can be defined by the natural anatomy of the patient. However, in still further aspects, the outflow lumen can be fixated at a specific position within the cavity of the inflow lumen. In yet still further aspects, the catheter can comprise at least one portion where at least a portion of the second outer layer of the outflow lumen is coupled to at least a portion of the first inner layer of the inflow lumen.

Figure 2B:
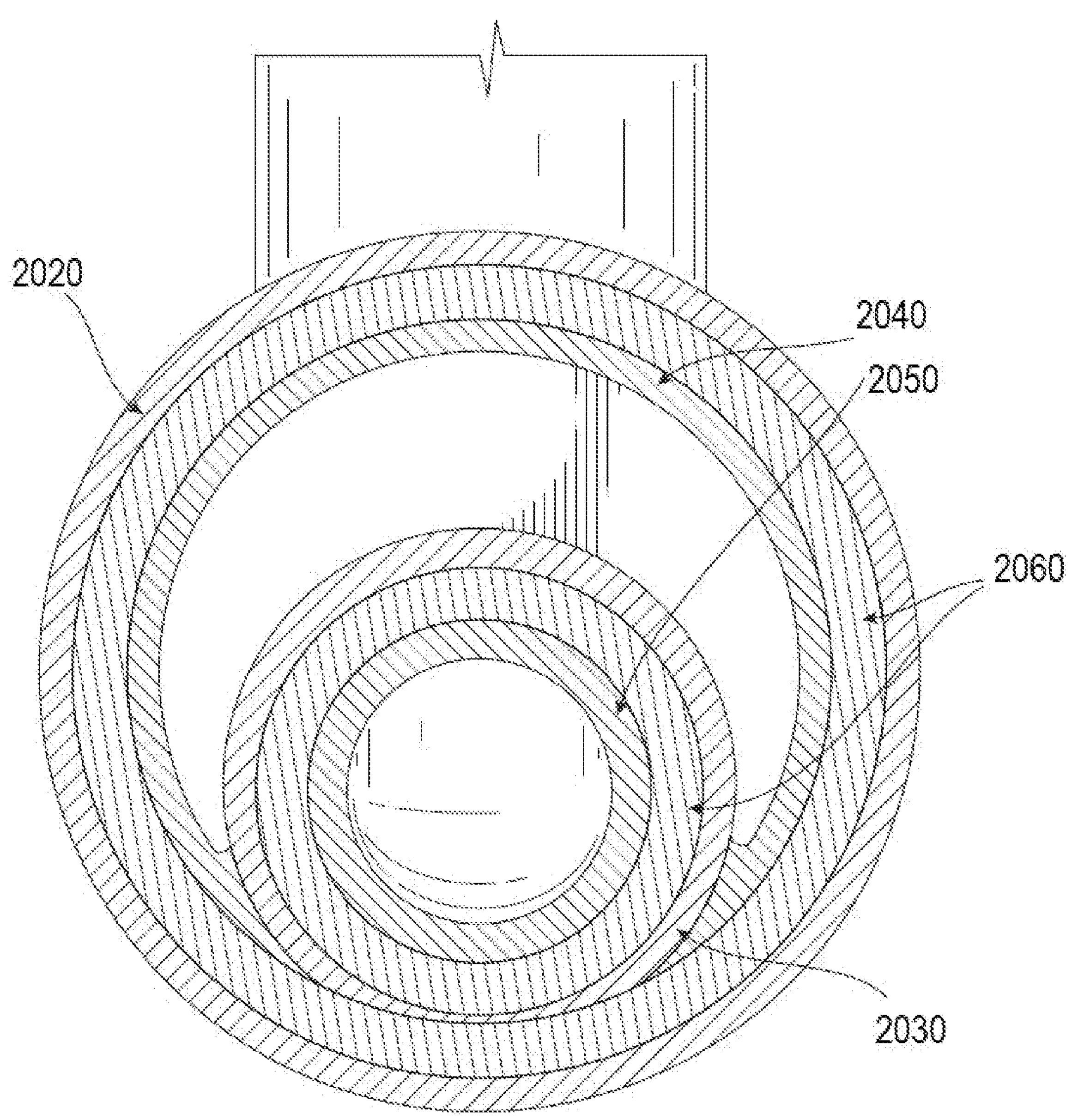
Figure 2C:
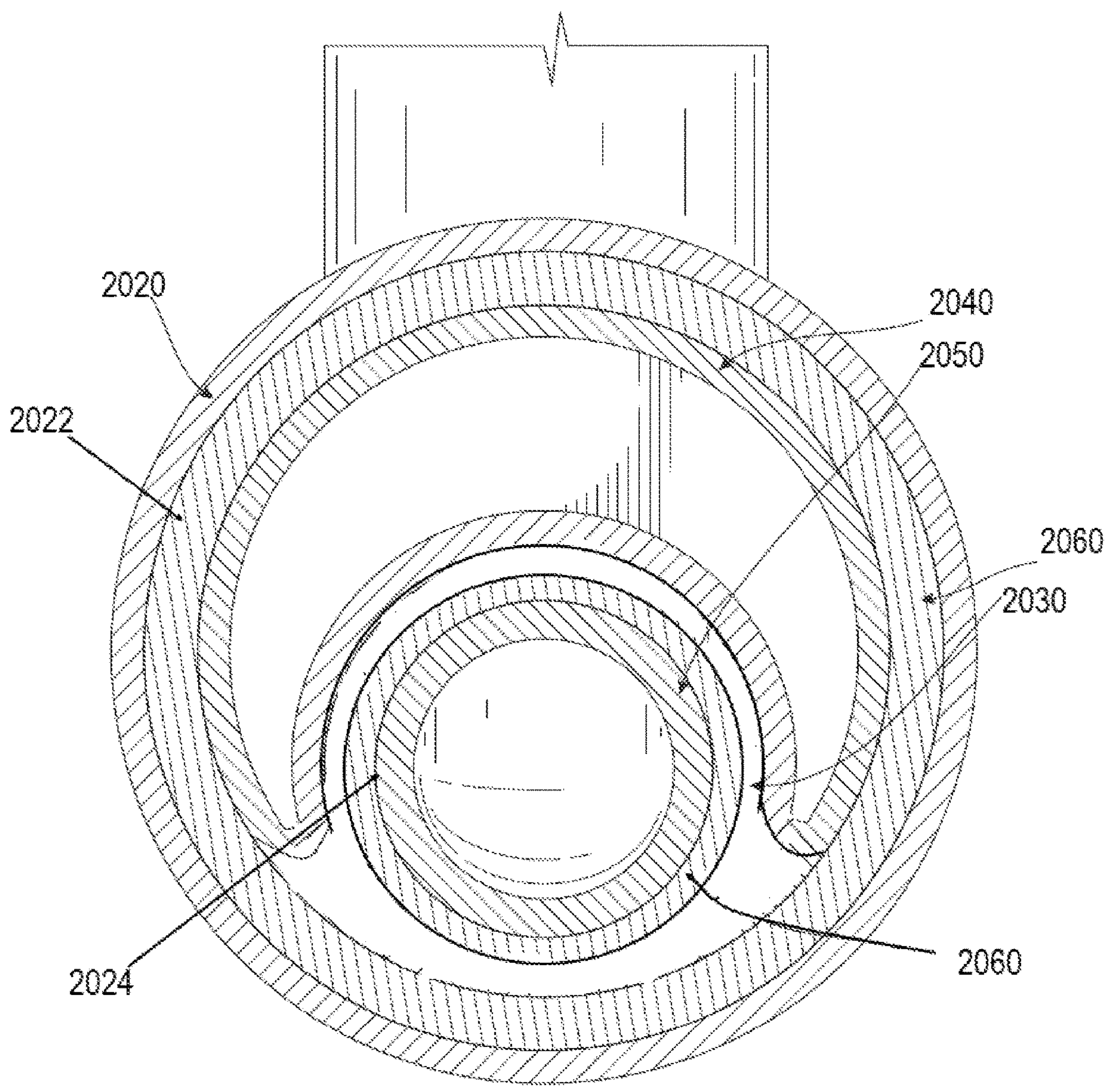

Referring now to FIGS. 2B and 2C that show some exemplary and unlimiting aspects of layer constructions for the catheter. FIG. 2B shows a configuration where the inflow lumen 2022 has a first outer layer 2020 and a first inner layer 2040, and wherein the outflow lumen 2024 has a second outer layer 2030 and a second inner layer 2050. As disclosed above, aspects where all or some of the layers are the same, are disclosed. Also disclosed are the aspects where all the layers are completely different. As shown in this aspect, the second outer layer 2030 of the outflow lumen 2024 may contact the first inner layer 2040 of the inflow lumen 2022 but is not coupled to it. In still further aspects, and as disclosed herein, the inflow and/or outflow lumen can comprise a reinforcement layer 2060.

Yet also disclosed herein are aspects where the outflow lumen 2024 has a second outer layer 2030 that at least partially coupled with the inflow lumen 2022, thereby fixating the outflow lumen with the wall of the inflow lumen and creating a "crescent-like" cavity within the inflow lumen (FIG. 2C). In this exemplary and unlimiting aspect, the second outer layer 2030 can be, for example, coupled with the reinforcing layer 2060 of the inflow lumen 2022. In such aspects, the reinforcing layer 2060 of the inflow lumen can be encapsulated in the second outer layer of the outflow lumen in at least the coupling portion. However, it is understood that the aspects where no encapsulation occurs are also disclosed. In such aspects, the second outer layer of the outflow lumen can be disposed on the reinforcing layer of the inflow layer without encapsulating it. In still further exemplary aspects, the first inner layer 2040 of the inflow lumen 2022 can also be disposed outwards of the second of the outflow lumen 2024 within the inflow lumen cavity such that all portions of the "crescent-like" cavity are covered by the first inner layer 2040 (FIG. 2C).

Figure 2D:
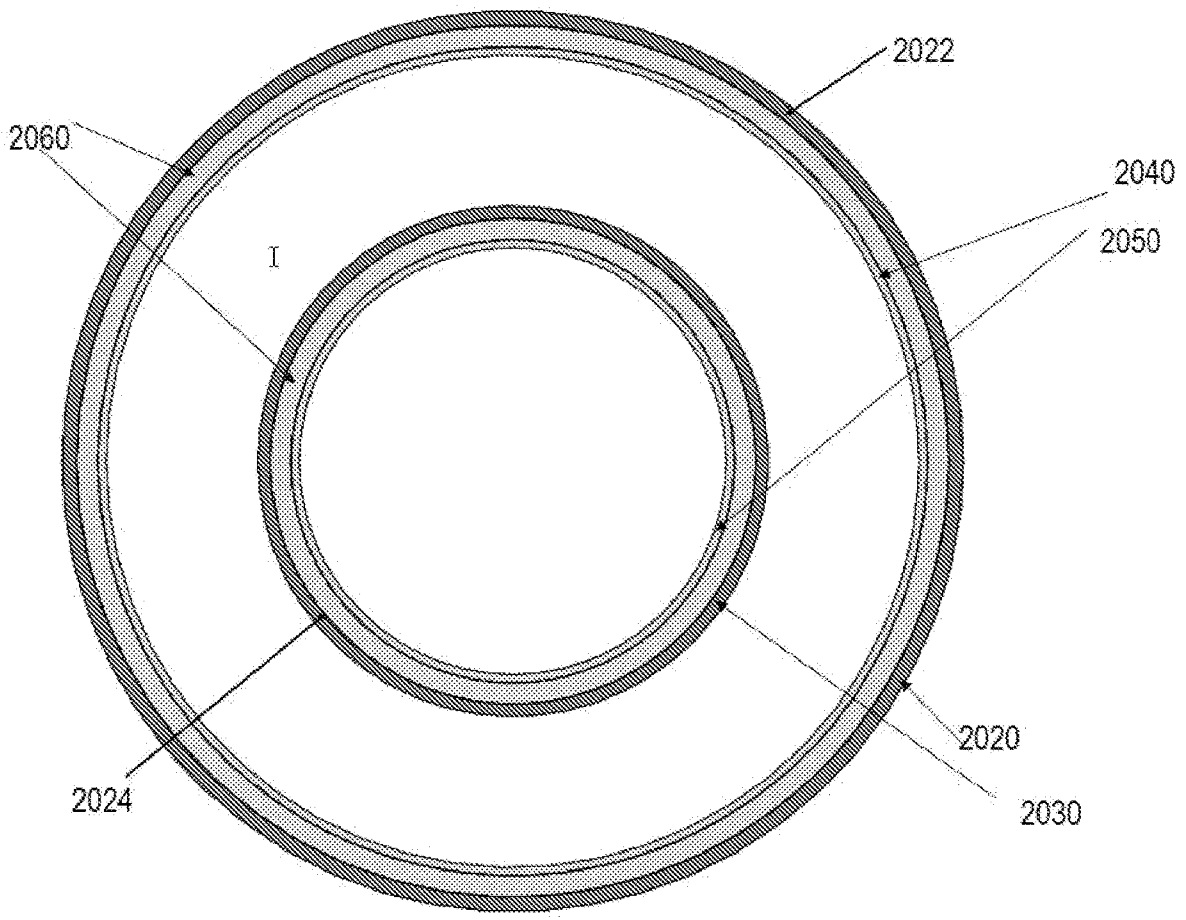

Also disclosed are aspects where the inflow and outflow lumen are disposed concentrically (FIG. 2D).

In still further aspects, and as shown in FIGS. 2A-2C, the cross-section of the blood flow channels is non-circular. It is further understood that such a cross section can be optimized to minimize pressure drop yet constraining the overall diameter to insertion of the catheter. In certain aspects, such an optimization can be achieved by using a reinforcing layer. In such aspects, the catheter can comprise a reinforcing layer. It is understood that the reinforcing layer can provide the catheter with the desired flexibility and rigidity. It is further understood that the use of the reinforcing layer can provide excellent flexibility while limiting wall thickness and thus minimizing the footprint of the catheter.

In certain aspects, the reinforcing layer can be substantially encapsulated within the outer layer. As discussed above and as shown in FIGS. 2B-2D, the reinforcing layer 2060 can be disposed between the outer layer and the inner layer. It is understood that the reinforcing layer can be made of any material that can serve the desired purpose and is compatible with medical applications. For example, the reinforcing layer can comprise a braid, a metal frame, or any combination thereof. For example, the braid can be metallic or polymeric. In some aspects, the braid comprises a flat-wound wire. Yet, in other aspects, the metal frame can comprise a laser-cut hypotube. In aspects where the braid is metallic, it can comprise stainless steel or nitinol. Yet, in other aspects, the metal frame can also comprise stainless steel or nitinol or titanium alloys, or a combination thereof. It is further understood that if braid or metal frame are present, they are flexible enough to move within the catheter to adjust to the natural anatomy of the patient and to allow the catheter to arrive at the desired destination. In yet still further aspects, the catheter is substantially kink-free. In such aspects, the disclosed herein catheter allows the surgeon to deliver it to the desired destination without adding unnecessary trauma to the surrounding tissues of the patient.

In still further aspects, the reinforcing layer can be positioned along the entire length of the catheter or along any desired portion, depending on the desired applications.

In still further aspects, the catheter can also comprise at least one radiopaque filler or marker. The radiopaque filler or marker can be positioned anywhere on the catheter. In some aspects, the radiopaque filler or marker can be positioned around the distal end of the first portion to allow fluoroscopic guidance of the catheter when it is inserted into the patient's body. Suitable materials for use as a radiopaque filler or marker include, for example, barium sulfite, bismuth trioxide, titanium dioxide, bismuth subcarbonate, or combinations thereof. The radiopaque filler can be mixed with or embedded in the first and/or second outer layer and the first and/or second inner layers of the inflow and/or outflow lumens. In yet other aspects, the reinforcement layer, if present, can serve as a radiopaque material.

In yet other aspects, the optimization can also be achieved by providing a variable the first and second diameters along the length of the catheter such that the portion external to the patient has a greater diameter than the indwelling portion, and the region of the elbow, a common source of pressure drop, is enlarged. In other words, disclosed herein are aspects where the first diameter of the inflow lumen is the same or different along the entire length of the inflow lumen. In still further aspects, the diameter of the inflow and outflow lumens are constant along the entire length of the catheter. In such aspects, it is understood that the blood flowing out of the right atrium comes back to the left atrium at substantially identical flow rates.

Yet, in some aspects, the first diameter can gradually vary along the entire length of the inflow lumen, or it can randomly vary along the entire length of the inflow lumen. Similarly, the second diameter of the outflow lumen can be the same or different along the entire length of the outflow lumen. In some aspects, the second diameter can gradually vary along the entire length of the outflow lumen, or it can randomly vary along the entire length of the outflow lumen. In still further aspects, the second diameter of the outflow lumen in the first portion can be the same or different as the second diameter of the outflow lumen in the second portion and/or third portion. It is understood, however, that in such aspects, the diameters of the catheters are configured such that the blood outflow rate is substantially identical to the blood inflow rate.

In still further aspects, the inner and/or the outer layer can further comprise a pharmaceutically active agent. In such aspects, the pharmaceutically active agent can comprise at least one of an antibiotic agent, antithrombotic agent, or any combination thereof. It is understood that any known in the art antibiotic agents and/or antithrombotic agents can be utilized. In certain aspects, for example, and without limitations, the antibiotic agents can comprise chlorhexidine, vancomycin, gentamycin, cephalosporin, or penicillin. While in other aspects, for example, and without limitations, the antithrombotic agents can comprise a heparinoid. It is further understood that these pharmaceutically active agents can be, for example, and without limitations, incorporated within the first/second outer layer and/or first/second inner layer, or they can be applied as separate coatings. However, it is understood that these agents are only exemplary and any known in the art antibiotics, anticoagulants, or antiplatelet agents.

In still further aspects, and as shown in FIG. 1, the distal end of the outflow lumen is substantially the same as the distal end of the first portion and wherein the distal end of the inflow lumen is substantially the same as the distal end of the third portion. As also shown in FIG. 1, the proximal end of the first portion extends into the distal end of the second portion, and the distal end comprises an outlet of the outflow lumen through which the oxygenated blood is delivered into the left atrium.

In some aspects, the distal end of the first portion can be tapered. However, the aspects where the distal end of the first portion is not tapered are also disclosed.

As disclosed above, the proximal end of the second portion extends into the distal end of the third portion and wherein the proximal end of the third portion comprises an outlet of the inflow lumen that is configured to deliver blood to the oxygenator.

Figure 3:
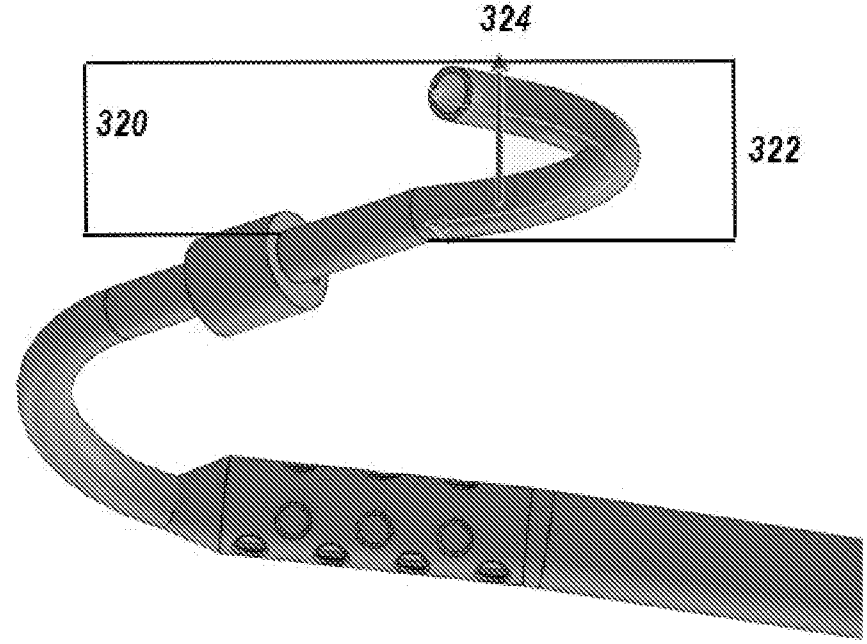
FIG. 3 is a perspective view showing an exemplary pitch of a helical portion of a first portion in one aspect.
Figure 4:
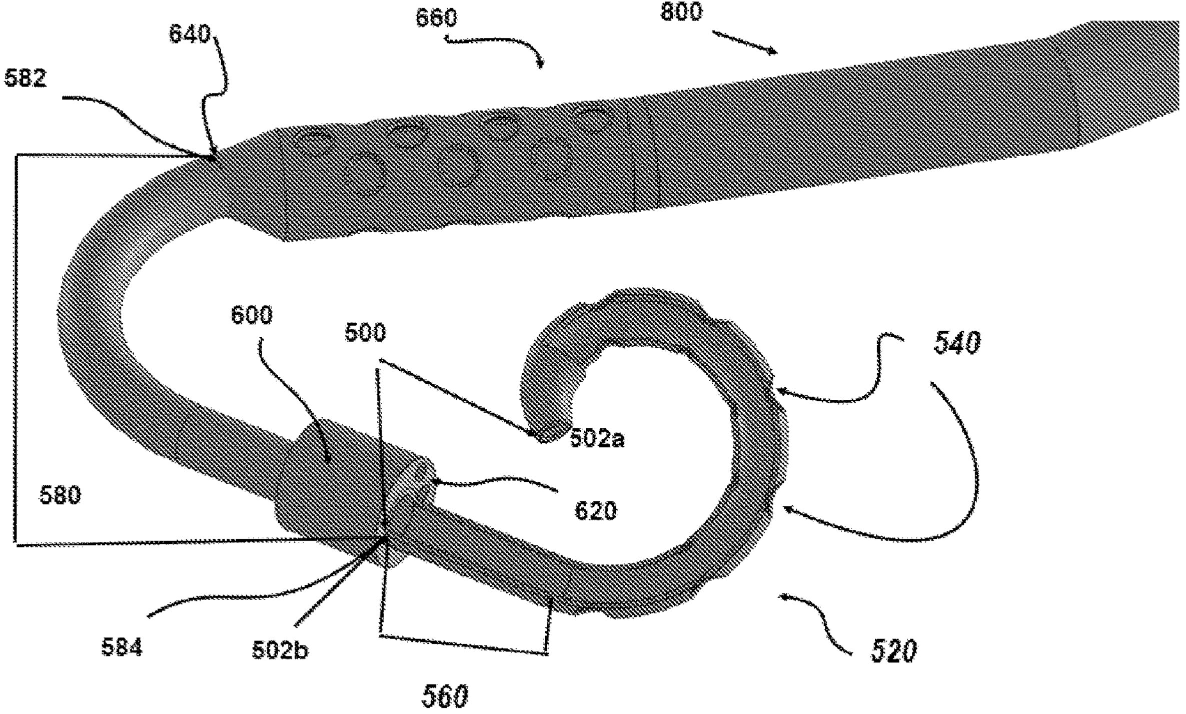
FIG. 4 is a perspective view of a first portion, a second portion, and a third portion of an exemplary catheter in one aspect.
Figure 5:
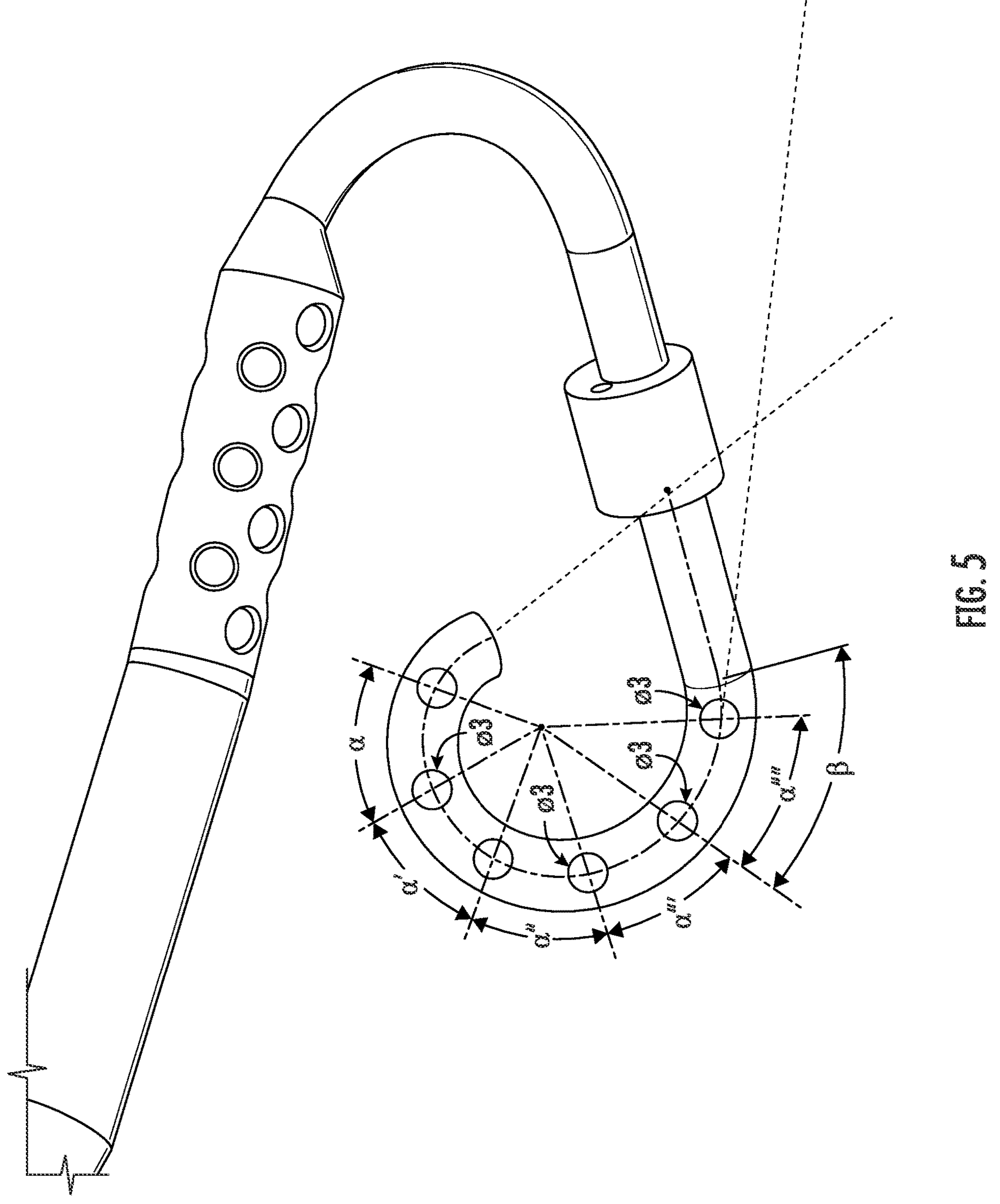
FIG. 5 shows a perspective view of an exemplary positioning of a first plurality of fenestrations in one aspect.

FIGS. 3-5 allow a closer look at the first portion of the disclosed herein catheter. Referring now to FIG. 3. FIG. 3 shows the first portion of the catheter 320 and the helical portion 322. The helical portion can follow a helical path 324, having a pitch from 0 mm to about 30 mm, including exemplary values of about 0.25 mm, about 0.5 mm, about 0.75 mm, about 1 mm, about 1.5 mm, about 2 mm, about 3 mm, about 4 mm, about 5 mm, about 7 mm, about 10 mm, about 12 mm, about 15 mm, about 17 mm, about 20 mm, about 22 mm, about 25 mm, and about 27 mm.

In yet still further aspects, the helical portion 322 can have an initial curvature radius from about 0.2 mm to about 30 mm, including exemplary values of about 0.5 mm, about 0.75 mm, about 1 mm, about 1.5 mm, about 2 mm, about 3 mm, about 4 mm, about 5 mm, about 7 mm, about 10 mm, about 12 mm, about 15 mm, about 17 mm, about 20 mm, about 22 mm, about 25 mm, and about 27 mm.

In still further aspects, the helical portion can be defined by a number of revolutions. In such aspects, the helical portion can comprise from about 0.2 to about 1.5 revolutions, including exemplary aspects of about 0.25, about 0.3, about 0.35, about 0.4, about 0.45, about 0.5, about 0.55, about 0.6, about 0.65, about 0.7, about 0.75, about 0.8, about 0.85, about 0.9, about 0.95, about 1.0, about 1.05, about 1.1, about 1.15, about 1.2, about 1.25, about 1.3, about 1.35, about 1.4 and about 1.45.

In still further aspects and as shown in FIG. 4, the first portion 500 defined by the distal end 502*a* and the proximal end 502*b* has a helical portion 520 that starts from the distal end of the first portion and extends towards its proximal end. The helical portion 520 comprises a first plurality of fenestrations 540 configured to prevent jet impingement on an endocardial surface of the left atrium. It also prevents jet impingement of pulmonary veins. It is understood that this first plurality of fenestrations can be disposed around a circumference of the first portion in a predetermined or random pattern. An exemplary aspect is shown in FIG. 5, where the fenestrations are disposed at different angles from each other ($\alpha$ through $\alpha''''$), where these angles can be the same or different. In some exemplary and unlimiting aspects, the angles can be ranged from about 5 degrees to about 180 degrees, including exemplary values of about 10 degrees, about 15 degrees, about 20 degrees, about 25 degrees, about 30 degrees, about 35 degrees, about 40 degrees, about 45 degrees, about 50 degrees, about 55 degrees, about 60 degrees, about 65 degrees, about 70 degrees, about 75 degrees, about 80 degrees, about 85 degrees, about 90 degrees, about 95 degrees, about 100 degrees, about 110 degrees, about 120 degrees, about 130 degrees, about 140 degrees, about 150 degrees, about 160 degrees, and about 170 degrees. The angle $\beta$ shows the angle of helical portion formation.

The first plurality of fenestration can comprise any number of fenestrations suitable for the specific application. For example and without limitations, the first plurality of fenestrations can comprise from 2 to 25 fenestrations, including exemplary values of 3, 4, 5, 6, 7, 8, 9, 10, 11, 12, 13, 14, 15, 16, 17, 18, 19, 20, 21, 22, 23, and 24. It is further understood that each of the plurality of fenestrations can have the same or different diameter $\phi$. It is understood that the fenestrations can be circular. However, the fenestration can have any regular and irregular shape. For example, and without limitations, the fenestrations can be triangular, star-like, oval, elliptical, rhombical, square, rectangular, trapezoid, hexagon, pentagon, octagon, and the like.

In still further aspects, it is understood that when the catheter is inserted into the patient body, the proximal end of the first portion is positioned on a left side of the atrium septum. In still further aspects, when the catheter is introduced into the patient body, the first portion of the catheter is positioned within the left atrium such that there is substantially no contact with the natural anatomy of the left atrium. In yet still, further aspects, when the catheter is introduced into the patients body, the distal end of the first portion faces downward to a mitral valve and away from a pulmonary vein (see FIG. 13).

In still further aspects, the first portion can further comprise a first sensory element. It is understood that any sensory elements can be incorporated depending on the specific application. In some aspects, the first sensory element is a first pressure sensor. These aspects can be schematically viewed in FIGS. 10A-10B. It can be seen that catheter 108 can be positioned in the heart such that it penetrates an atrium septum 106 when the first portion 118 of the catheter is positioned in the left atrium 104 and has a first plurality of fenestrations 114. It can be further seen that the first sensor 1108 can be disposed anywhere around the first plurality of fenestrations. In the aspect disclosed in FIGS. 10A-10B, the first pressure sensor is positioned closer to the distal end of the first portion. In other aspects, for example, and without limitations, the first sensor can be positioned just part left side of the atrial septum before the first plurality of fenestrations. In yet in other aspects, not shown, the first pressure sensor can be positioned anywhere within 0 to about 30 mm, including exemplary values of 0.25 mm, about 0.5 mm, about 0.75 mm, about 1 mm, about 1.5 mm, about 2 mm, about 3 mm, about 4 mm, about 5 mm, about 7 mm, about 10 mm, about 12 mm, about 15 mm, about 17 mm, about 20 mm, about 22 mm, about 25 mm, and about 27 mm from the distal end of the second portion towards the distal end of the first portion.

It is further understood that the first pressure sensor can be positioned anywhere within the first portion of the catheter. For example, and without limitations, it can be positioned in the second outer layer and/or second inner layer or within the outflow lumen cavity if desired.

In still further aspects, the first portion can further comprise at least a portion 560 (FIG. 4) that is substantially free of any fenestrations. In such exemplary and unlimiting aspects, the at least a portion of the first portion that is substantially free of any fenestrations has a length that is the same or different from the first length. In yet still further aspects, the first pressure sensor can be positioned anywhere within the length of the at least a portion of the first portion that is substantially free of any fenestrations.

It is understood that any known in the art pressure sensors that are compatible with the desired application can be utilized. For example, and without limitations, commercially available piezoelectric pressure sensors (Millar, Houston, TX) can be used to monitor LA pressure. In still further exemplary and unlimiting aspects, the pressure sensor can be connected to a control unit. Such connectivity can be achieved through wired or wireless communication. In the aspects where the wires are utilized, such wires can be routed within the second outer layer and/or the second inner layer of the first portion and externalized to a connector at the proximal end of the catheter. It is understood that the first pressure sensor is compatible with a standard patient monitor that can be further incorporated into a long-term right ventricular assist system (FIGS. 14A-14C) that will help regulate pump flow manually or automatically.

In still further aspects, and as shown in FIG. 4, the disclosed herein catheter further comprises a second portion 580. The proximal end 582 of the second portion 580 is substantially the same as the distal end 640 of the third portion 660. In some aspects, and as shown in FIG. 4, the distal end of the third portion 640 can be tapered. However, aspects where the distal end of the third portion is not tapered, are also disclosed.

It is understood that the second portion has a second length. In some aspects, the second length is the same as the first length of the first portion. While in yet other aspects, the second length is different from the first length of the first portion. In still further aspects, it is understood that when the catheter is inserted into the patient body, at least a portion of the second portion is positioned within a right atrium (see FIG. 13). In yet still, further aspect, the distal end 584 of the second portion is positioned on a right side of the atrium septum when the catheter is inserted into the patient's body.

Figure 12A:
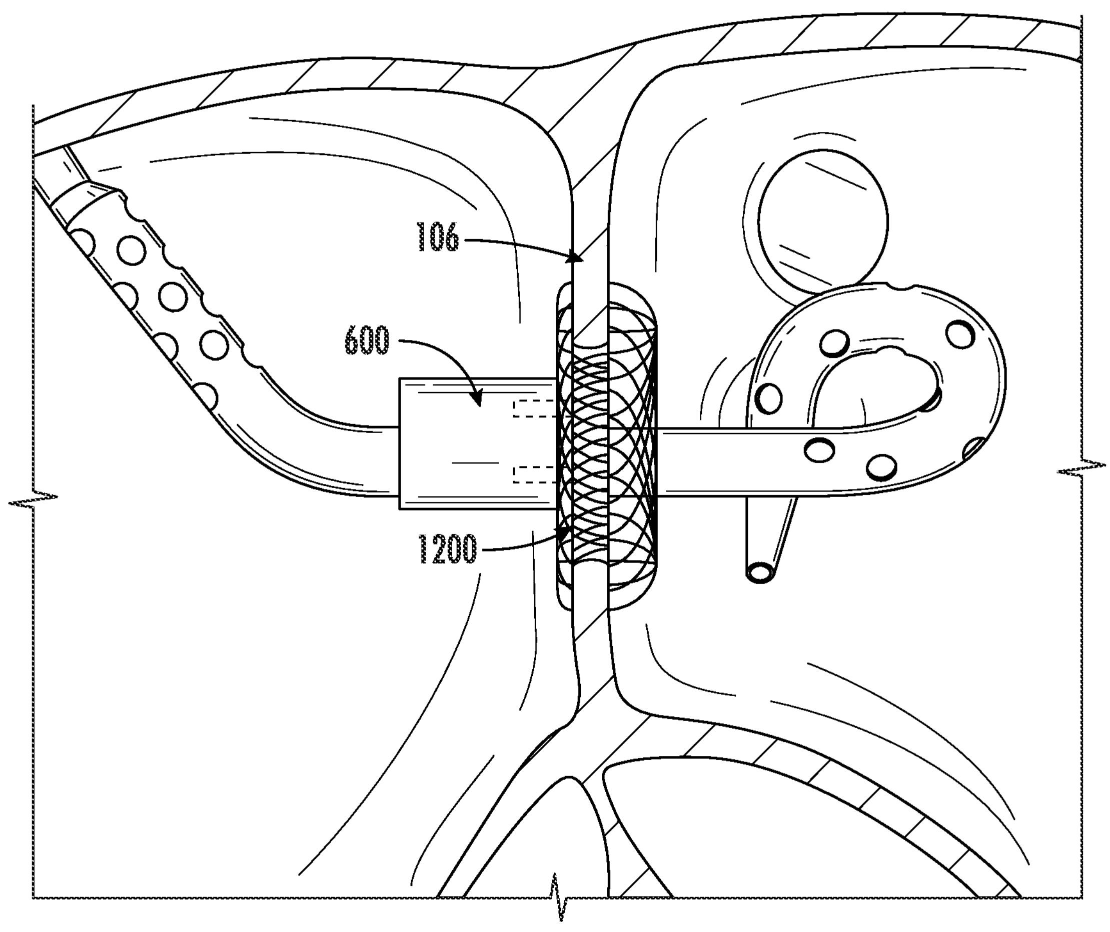
FIGS. 12A-12B show fixation of some of the catheters and atrial septal fixation and docking assemblies with an atrial septum in one aspect.
Figure 12B:
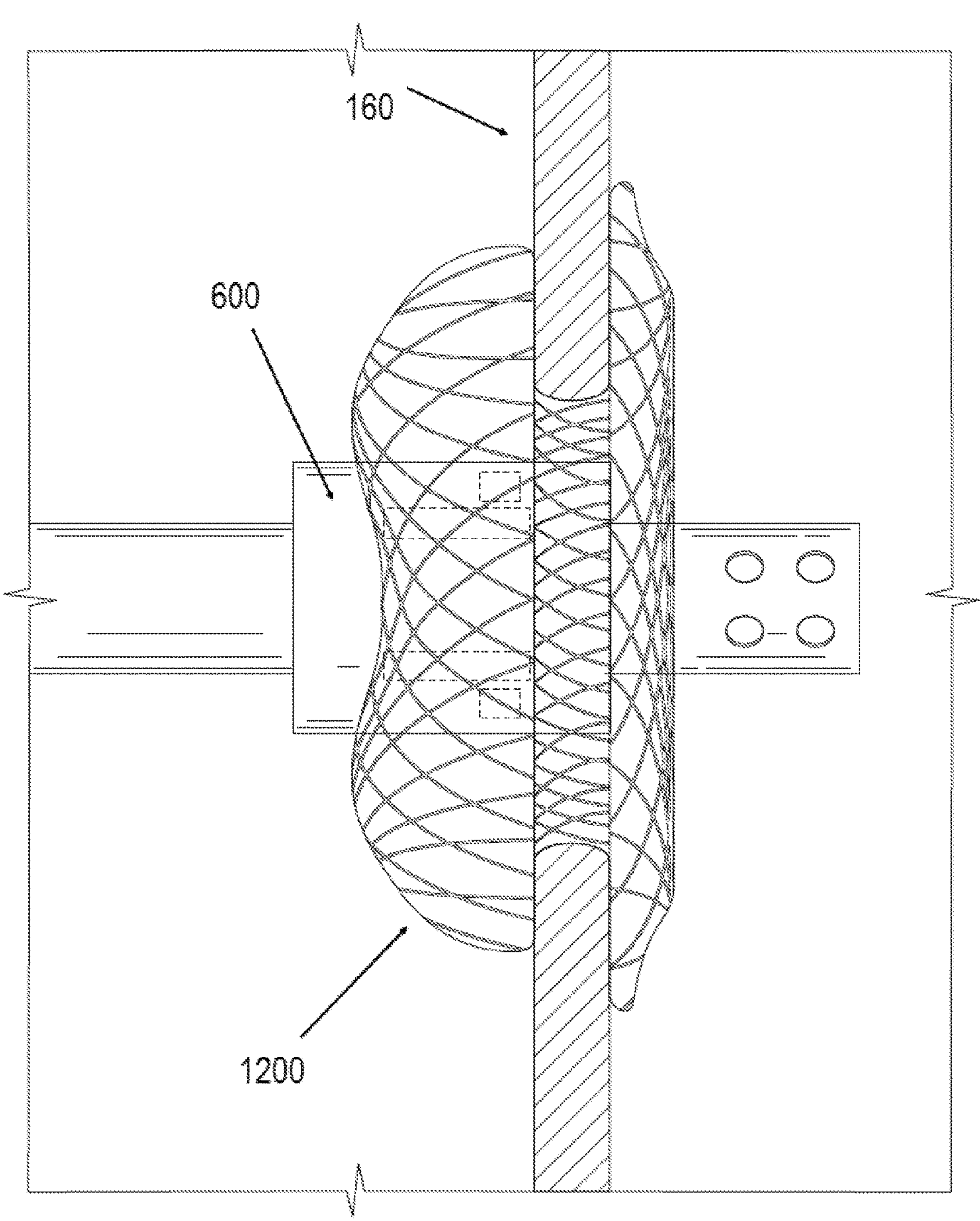

In still further aspects, the catheter disclosed herein can comprise an auxiliary member 600 positioned radially outward of the distal end 584 of the second portion 580. In still further aspects, the auxiliary member 600 is configured to removably attach the catheter to the atrium septum 106 (FIGS. 12A-12B).

Figure 6:
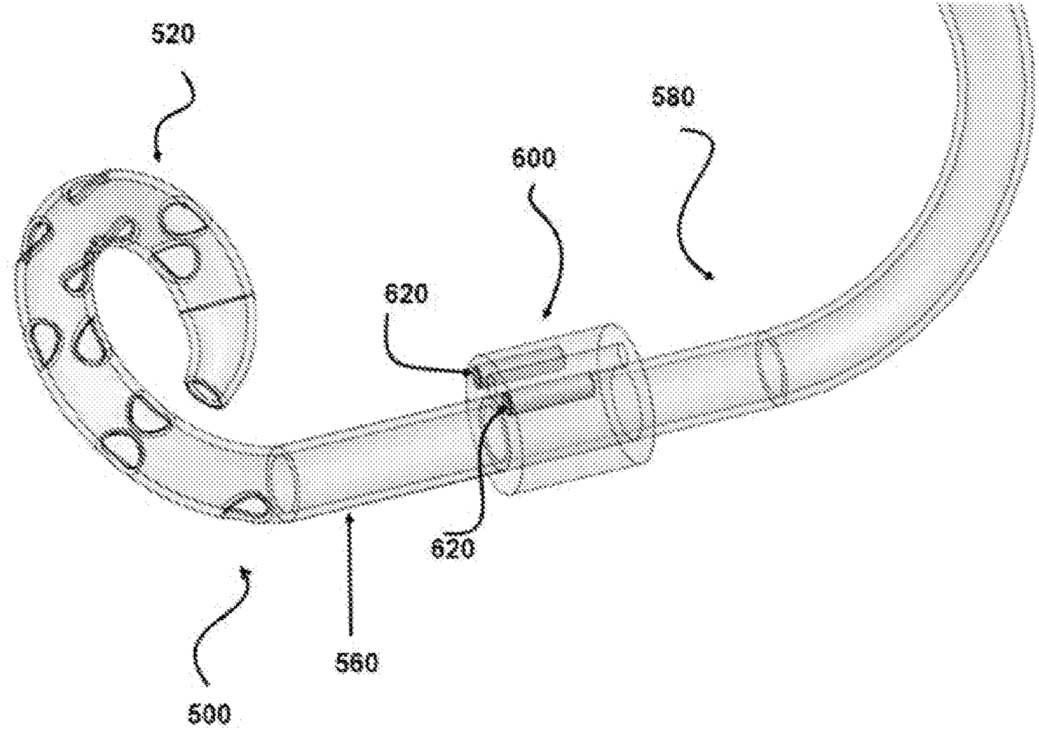
FIG. 6 shows a transparent perspective view of a first portion, a second portion of an exemplary catheter, an auxiliary member, and one or more exemplary magnets in one aspect.

FIG. 6 shows a transparent perspective view of the first portion 500 having a helical portion 520 with the plurality of fenestration and at least one portion that is free of any fenestrations 560, a second portion 580, and an auxiliary member 600. In certain aspects, the auxiliary member has a diameter greater than a diameter of the first and/or second portions (FIGS. 4 and 6). Yet, in other aspects, the auxiliary member can have a diameter greater, smaller, or substantially the same as a diameter of the third portion 660 (FIG. 4). In still further aspects, the auxiliary member has a predetermined length along the second length of the second portion. It is understood that this predetermined length can be determined based on the desired application.

In still further aspects, the auxiliary member 600 can comprise a plurality of magnets 620 (FIG. 4 and FIG. 6). It is understood that in such aspects, at least two of the plurality of magnets have opposite polarity. In still further aspects, the plurality of magnets can comprise from 2 to 10 magnets. It is understood that in such aspects, the plurality of magnets are permanent magnets and not electromagnets. In still further aspects, the plurality of magnets can be disposed in a predetermined orientation. In still further aspects, the magnets can comprise any material suitable for the desired application. For example, and without limitations, the plurality of magnets can comprise any known rare earth metal magnets. In certain aspects, the plurality of magnets comprise neodymium magnets. Yet, in other aspects, the plurality of magnets comprise samarium-cobalt magnets. Yet, in other aspects, the plurality of magnets can comprise alnico and ferrite. In yet still further aspects, the magnets are permanently magnetized normal to the planar end surfaces. In yet other aspects, the magnets can be disposed in an alternating pattern of magnetization to achieve the desired effect.

It is further understood, however, that the aspects where the second portion attaches to the right side of the atrium without the presence of the auxiliary member are also disclosed. In such aspects, the attachment can be done by direct incorporating of the one or more magnets into the second outer layer and/or second inner layer. In yet further aspects, the location where the second portion attaches to the right side of the atrium can be the same or different from the attachment location of the auxiliary member.

In still further aspects, and as disclosed herein, the catheter comprises a third portion 660 (FIG. 4, for example). In such aspects, the third portion has a diameter larger than a diameter of the first portion and/or second portion. As disclosed above, the third portion comprises both inflow and outflow lumens.

Figure 7:
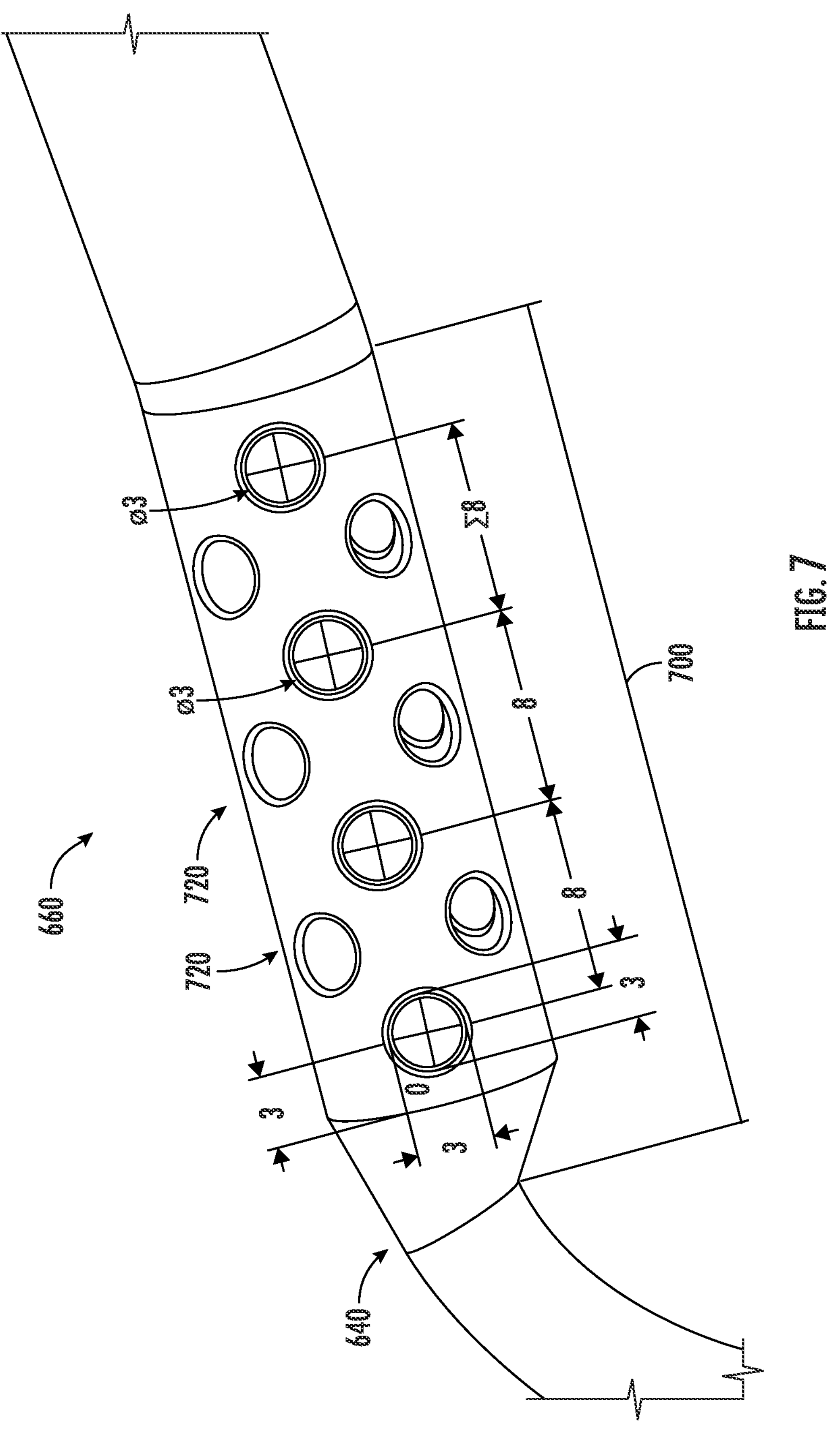
FIG. 7 shows a perspective view of an exemplary positioning of a second plurality of fenestrations in one aspect.

In yet still further aspects, the third portion comprises a portion having a second plurality of fenestrations. Referring to FIG. 7, for example, the third portion 660 comprises a portion 700 having the second plurality of fenestrations 720. It can be seen that in such aspects, the second plurality of fenestrations can abut the distal end 640 of the third portion 660 and have a third length. In still further aspects, the second plurality of fenestrations are configured to prevent suction of the atrial wall.

In certain aspects, the second plurality of fenestrations can be disposed circumferentially of the inlet lumen positioned in the third portion and wherein the outlet lumen positioned within the inlet lumen in the third portion is substantially free of any fenestrations. The second plurality of fenestration can have any regular or irregular shape. For example, and without limitations, any of the disclosed above shapes for the first plurality of fenestrations can also be applied to the second plurality of fenestrations.

In still further aspects, the second plurality of fenestrations are disposed in a predetermined or a random pattern. In still further aspects, the second plurality of fenestrations comprise from 4 to 30 fenestrations, including exemplary values of 5, 6, 7, 8, 9, 10, 11, 12, 13, 14, 15, 16, 17, 18, 19, 20, 21, 22, 23, 24, 25, 26, 27, 28, and 29.

In still further aspects, each of the second plurality of fenestrations can have the same or a different diameter. In some aspects, the diameter of each of the second plurality of fenestration is different from the diameter of each of the first plurality of fenestrations. However, aspects where the diameters of at least some of the first and the second pluralities of fenestrations are substantially the same are also disclosed.

In still further aspects, the third portion can further comprise a second sensory element. Again, it is understood that any known in the art sensory elements that are designed to achieve the desired application can be utilized. In some aspects, the second sensory element is a second pressure sensor. In some aspects, the second sensor can be disposed in the third portion and/or second portion.

Figure 10A:
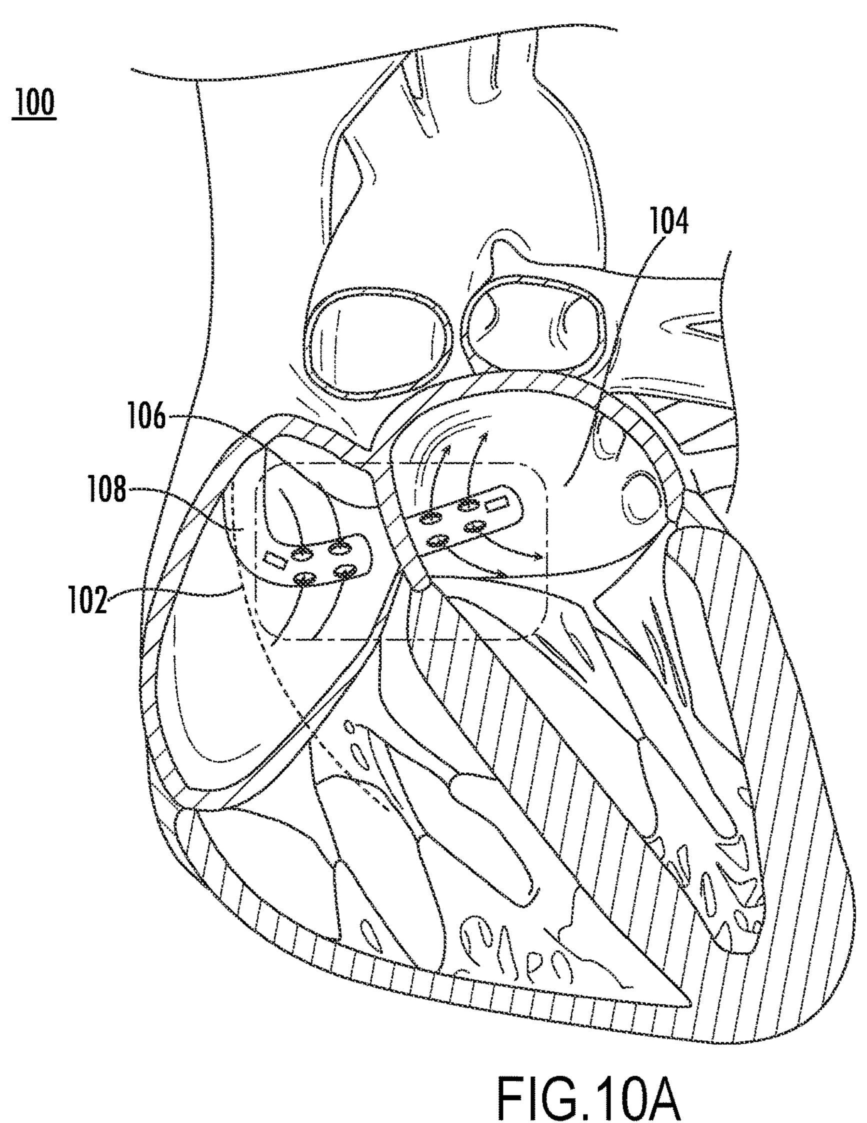
FIGS. 10A-10B show a schematic of positioning an exemplary system of an exemplary catheter and an exemplary atrial septal fixation and docking assembly in a heart in one aspect.
Figure 10B:
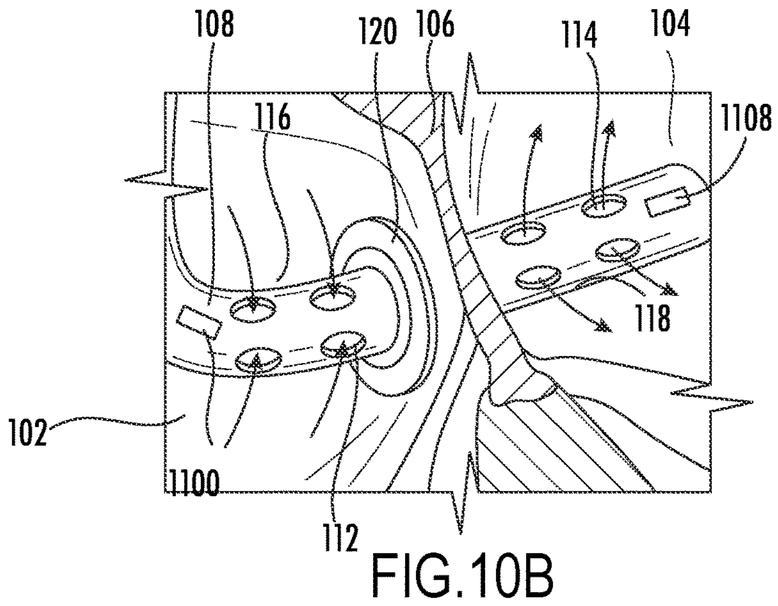

Some exemplary and unlimiting aspects, the third portion can also be schematically viewed in FIGS. 10A-10B. It can be seen that catheter 108 can be positioned in the heart such that it penetrates an atrium septum 106 when the first portion 118 of the catheter is positioned in the left atrium 104 and where the third portion 116 is positioned within the right atrium 102. The third portion has fenestrations 112 positioned on the right side of the atrium septum 106. It can be further seen that the second sensor 1100 can be disposed on a right side of the second plurality of fenestrations 112. In yet in other aspects, not shown, the second pressure sensor can be positioned anywhere within 0 to about 30 mm, including exemplary values of 0.25 mm, about 0.5 mm, about 0.75 mm, about 1 mm, about 1.5 mm, about 2 mm, about 3 mm, about 4 mm, about 5 mm, about 7 mm, about 10 mm, about 12 mm, about 15 mm, about 17 mm, about 20 mm, about 22 mm, about 25 mm, and about 27 mm from the terminal ends of the portion comprising the second plurality of fenestrations.

It is further understood that the second pressure sensor can be positioned anywhere on the second portion and/or third portion of the catheter. For example, and without limitations, it can be positioned in the second outer layer and/or second inner layer or within the outflow lumen cavity if desired if the second pressure sensor is positioned with the second portion. Yet, in other aspects, if the second pressure sensor is positioned within the third portion, it can be positioned within the first outer and/or inner layer of the inflow catheter or within the cavity of the inflow catheter. Yet in still further aspects, if the second pressure sensor is positioned within the third portion, it can be positioned within the second outer layer and/or second inner layer, or within the outflow lumen cavity if desired. Yet is still further aspects, the second pressure sensor can comprise more than one pressure sensors that can be positioned in any of the disclosed above locations.

It is understood that any known in the art pressure sensors that are compatible with the desired application can be utilized. For example, and without limitations, commercially available piezoelectric pressure sensors (Millar, Houston, TX) can be used to monitor RA pressure. In still further exemplary and unlimiting aspects, the pressure sensor can be connected to a control unit. Such connectivity can be achieved through wired or wireless communication. In the aspects where the wires are utilized, such wires can be routed within the first and/or second outer layer and/or the first and second inner layer of the second and/or third portions depending on its location and externalized to a connector at the proximal end of the catheter. It is understood that the second pressure sensor is compatible with a standard patient monitor that can be further incorporated into a long-term right ventricular assist system (FIGS. 14A-14C) that will help regulate pump flow manually or automatically.

In still further aspects, it is understood that the one or more second pressure sensors are not in close proximity to the second plurality of fenestrations. In still further aspects, the one or more second pressure sensors can be disposed at least 10 mm away from any of the terminals of the portion that comprises the second plurality of fenestrations. In such aspects, the one or more second pressure sensors can be disposed at least 10 mm on the right side from the second plurality of fenestrations within the third portion or on the left side from the second plurality of fenestrations within the second portion. In still further aspects, the one or more second pressure sensors can be disposed at least 10 mm, at least 12 mm, at least 15 mm, at least 17 mm, at least 20 mm, at least 22 mm, at least 25 mm, at least 27 mm, or at least 30 mm away from any of the terminals of the portion that comprises the second plurality of fenestrations.

Figure 13:
FIG. 13 shows a schematic of the catheter placement in the heart according to one aspect.

In still further aspects, the third portion has at least a portion 800 (FIG. 4) that is substantially free of any fenestrations. In still further aspects, when the catheter is inserted into the patient body, at least a portion of the third portion is positioned within the right atrium (FIG. 13). In yet further aspects, the at least a portion of the third portion that is positioned within the right atrium is at least a portion of the portion having the second plurality of fenestrations (FIG. 13, FIGS. 10A-10B). In yet still, further aspects, when the catheter is inserted into the patient body, at least a portion of the third portion is positioned within the superior vena cava (FIG. 13). In still further aspects, wherein at least a portion of the third portion that is positioned within superior vena cava is substantially free of the second plurality of fenestrations (FIG. 13).

In still further aspects, the catheter described herein is configured to support up to about 0.5 L/min, up to about 1 L/min, up to about 1.5 L/min, up to about 2 L/min, up to about 2.5 L/min, up to about 3 L/min, up to about 3.5 L/min or up to about 4/L min of the blood.

As disclosed herein, the catheter is inserted into the patient's body. In some aspects, the catheter can be introduced using a modified Seldinger technique, with the first portion being positioned on the left side of the atrial septum and the second portion on the right side of the atrium septum. To ensure the stable positioning of the catheter, the catheter will be locked within an atrial septal fixation and docking assembly. An exemplary and unlimiting schematics of such docking assemblies (1200) are shown, for example, in FIGS. 12A-12B. Such an assembly is described in detail below.

In certain aspects, disclosed herein is an atrial septal fixation and docking assembly comprising: an atrial member having a predetermined length, a first portion, and a second portion; wherein the atrial member has a crimped profile having a first diameter and an expanded profile having a second diameter, wherein the second diameter is greater than the first diameter. In further aspects, when the atrial member is inserted into an atrial septum to form an aperture of a predetermined dimension in the atrial septum, the first portion is fixated to a left side of the atrial septum, and the second portion is fixated to a right side of the atrial septum. In still further aspects, the atrial member encapsulates the aperture such that there is substantially no change in the predetermined dimension of the aperture for a predetermined period of time. In still further aspects, the atrial member is configured to be delivered to the atrial septum in the crimped profile, and when the atrial member is removably fixated with the atrial septum, the atrial member is present in the expanded profile. In yet further aspects, wherein the second portion of the atrial member can comprise one or more magnets.

It is understood that in order to deliver the atrial member to the atrial septum, an initial septostomy procedure needs to be performed.

Figure 8:
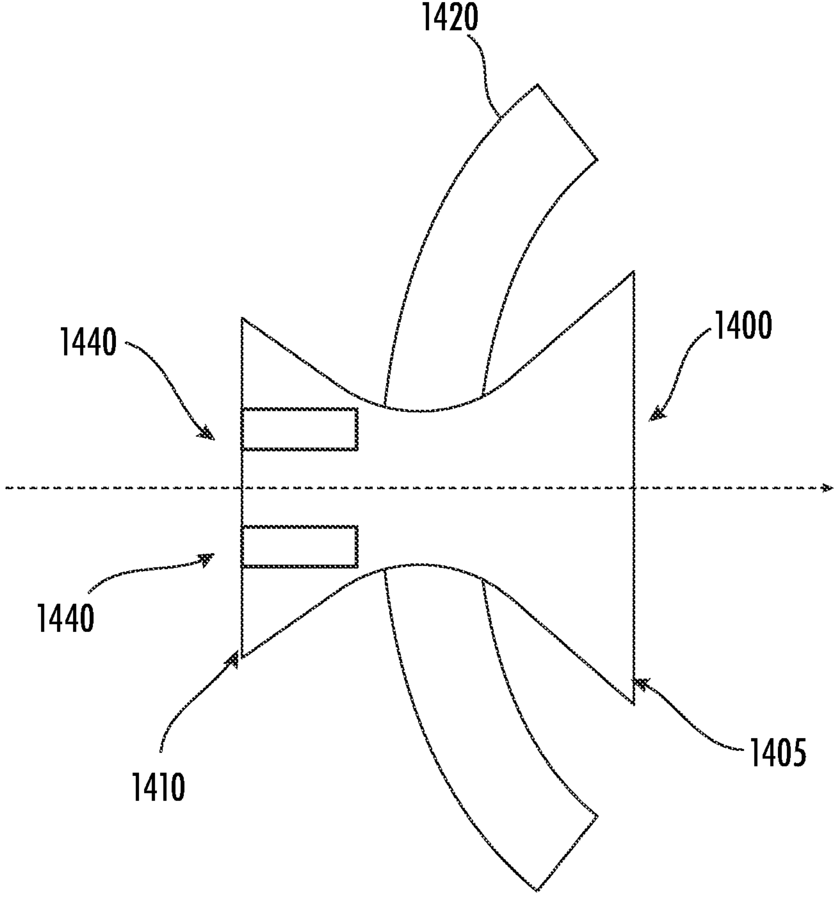
FIG. 8 shows a schematic of positioning of an exemplary atrial septal fixation and docking assembly within an atrial septum.

Exemplary the atrial septal fixation and docking assemblies are shown in FIGS. 8 and 9A-9H. Now referring to FIG. 8. FIG. 8 shows an atrial member 1400 inserted into the atrial septum 1420 along an axis 1402. The atrial member 1400 has a first portion 1405 disposed on the left side of the atrium septum 1420 and a second portion 1410 disposed on the right side of atrium septum 1420. The second portion 1410 comprises one or more magnets 1440 that are disposed such that when the catheter is inserted into the septum, the portion of the catheter that comprises the plurality of magnets is attracted to the one or more magnets of the atrium member and locks the catheter in place. The one or more magnets of the atrial members can be the same or different from the plurality of magnets disposed in the second portion of the catheter. It is understood that the one or more magnets present in the second portion of the atrial member and the plurality of magnets present in the second portion of the catheter are arranged in such a pattern of magnetization that the catheter is only locked-in in the desired orientation.

It is understood that the magnetic poles are configured such that they attract and automatically center the catheter for insertion and repel when twisted clockwise) (or counterclockwise) to facilitate decoupling and removal.

In still further aspects, the docking assembly described herein provides rapid localization of the catheter within the assembly and also permits removal and re-insertion without the need for fluoroscopic guidance. However, if needed, fluoroscopic guidance can also be employed.

In still further aspects, when the catheter is removed and no more needed, the apertured formed within the septum can be closed with a plug comprising a plurality of magnets and configured to be locked within the septum fixation and docking assembly.

In certain aspects, the atrium member formed by utilizing by adapting and modifying according to the disclosed aspects any known in the art ASD (atrium septum defect) closure devices. Some exemplary septum fixation and docking assemblies are shown in FIGS. 9A-9H.

Figures 9A, 9B:
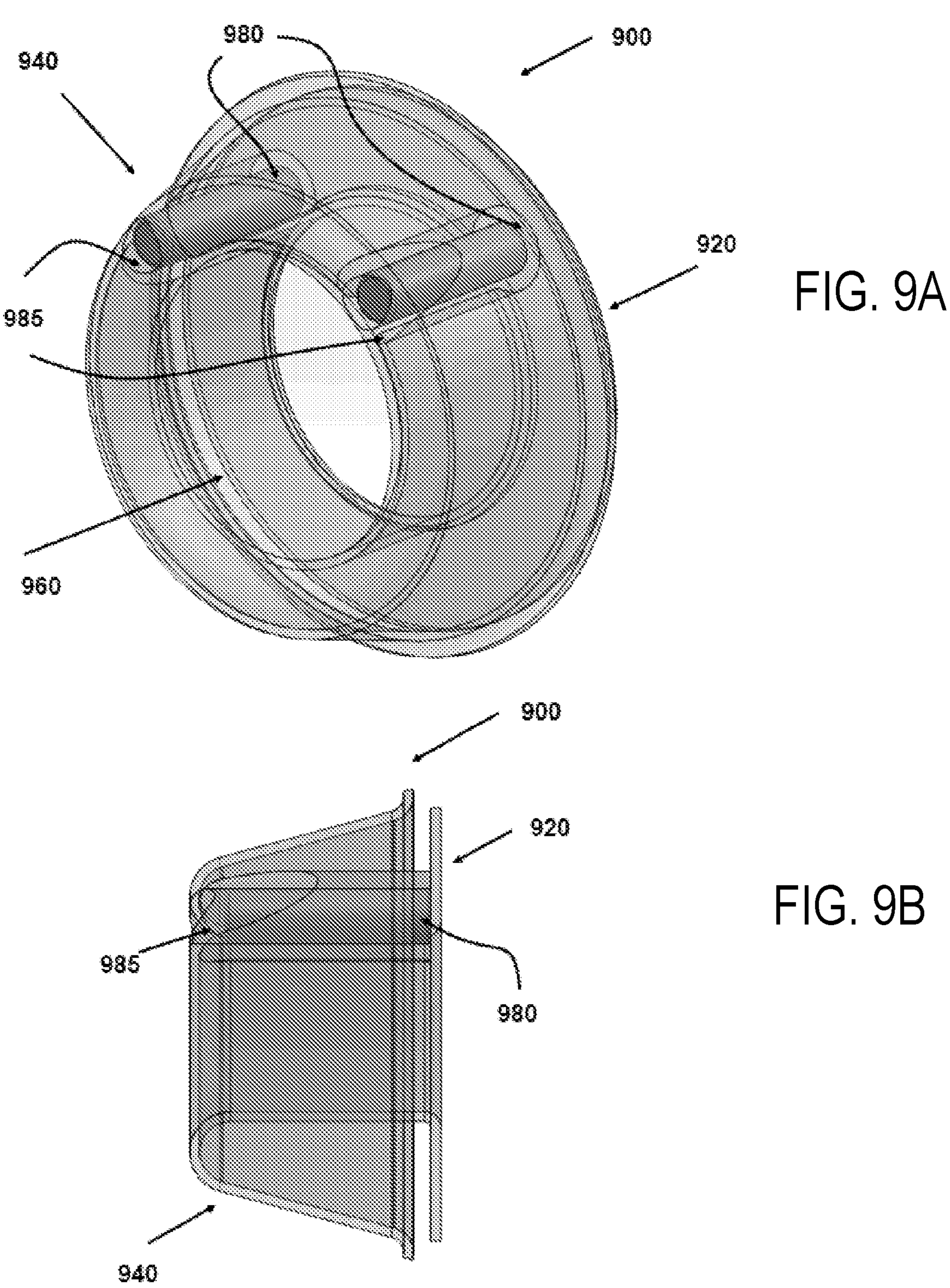
FIGS. 9A-9H show exemplary atrial septal fixations and docking assemblies in various aspects.

For example, FIGS. 9A and 9B show one aspect of the septum fixation and docking assembly 900 having a first portion 940 and a second portion 920 having magnets 980 incorporated within. The atrium member has an aperture 960 configured to receive the catheter. In certain aspects, the first portion 940 can also have apertures 985 configured to receive magnets 980 if desired. FIG. 11A shows an exemplary catheter locked within the septum fixation and docking assembly shown in FIGS. 9A and 9B.

Figure 9C:
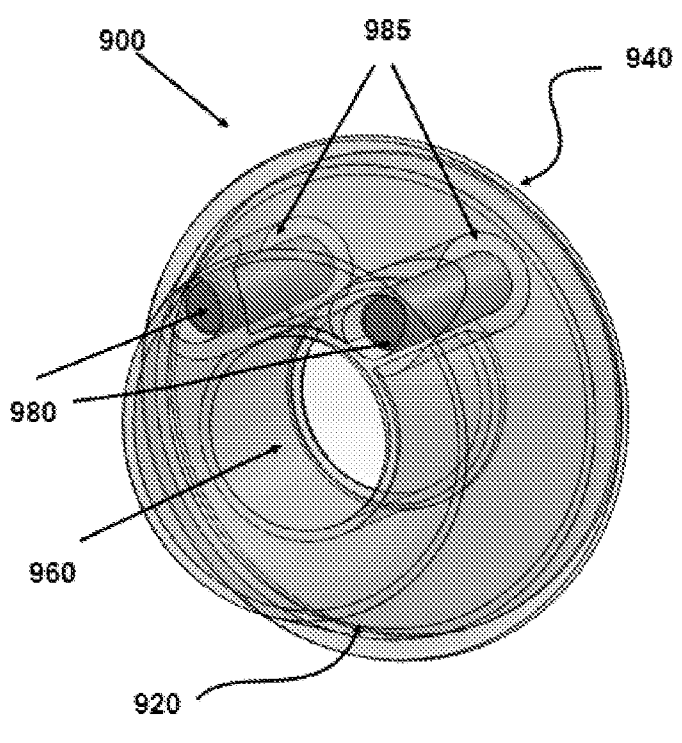
Figure 9D:
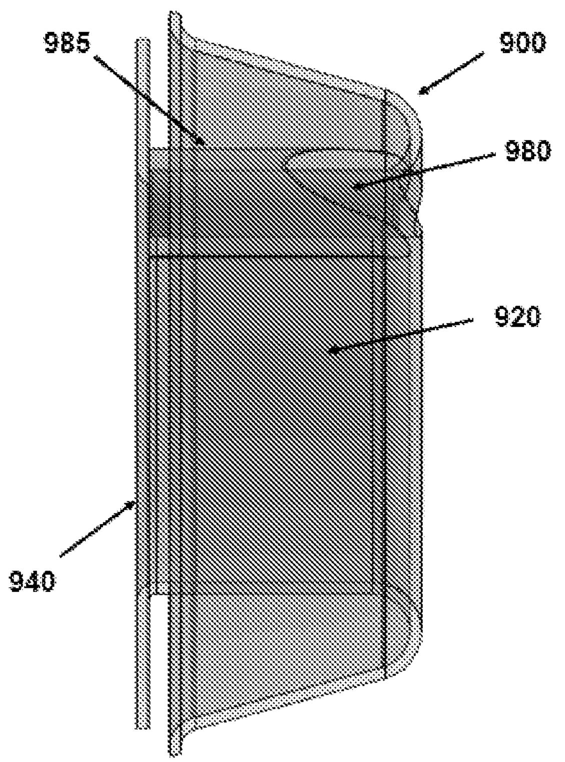

FIGS. 9C and 9D show a different configuration of the septum fixation and docking assembly 900 having a first portion 940 and a second portion 920 having magnets 980 incorporated within. The atrium member has an aperture 960 configured to receive the catheter. In certain aspects, the first portion 940 can also have apertures 985 configured to receive magnets 980 if desired. FIG. 11B shows an exemplary catheter locked within the septum fixation and docking assembly shown in FIGS. 9C and 9D. In this exemplary and unlimiting aspect, as it can be seen from FIGS. 9C-9D and 11B, the septum fixation and docking assembly can have a smaller footprint at at least a portion of the auxiliary member can be encapsulated by the second portion of the atrium member.

It is understood that the apertures shown in FIG. 9A-9D for the magnets 980 are only shown for the visual representations. It is understood that the magnets can be disposed in any applicable way whether the fixation station and docking assembly is a solid structure or a wire-made structure. It is understood that the FIG. 9A-9D are designed to indicate that there is a possible physical space that the docking system can unfold into. In such aspects, the magnets can be attached to the framework of the docking at a single point or node location so that the magnets essentially reside within the positions shown in these figures.

In still further aspects, it is understood that the fixation stations and docking assemblies are configured to be collapsible (have a crimped and expanded configuration) so they can be inserted through the femoral vein (or any other location through which the docking assembly is inserted into the patient body). Again, FIG. 9A-9D show only the final configuration of the docking.

Additional exemplary and unlimiting aspects of the septum fixation and docking assembly are shown in FIGS. 9E-9H.

Figure 9E:
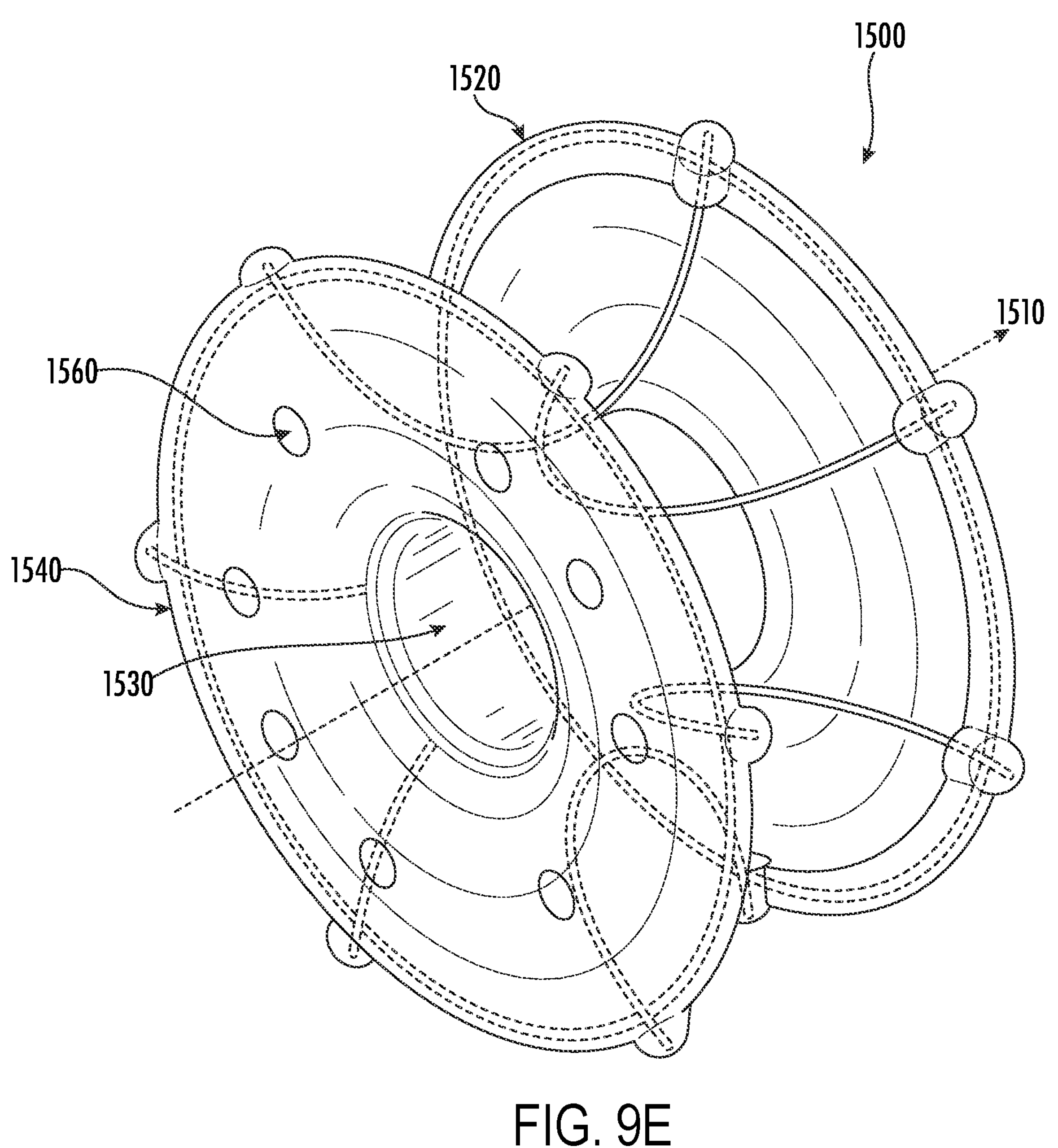
Figure 9F:
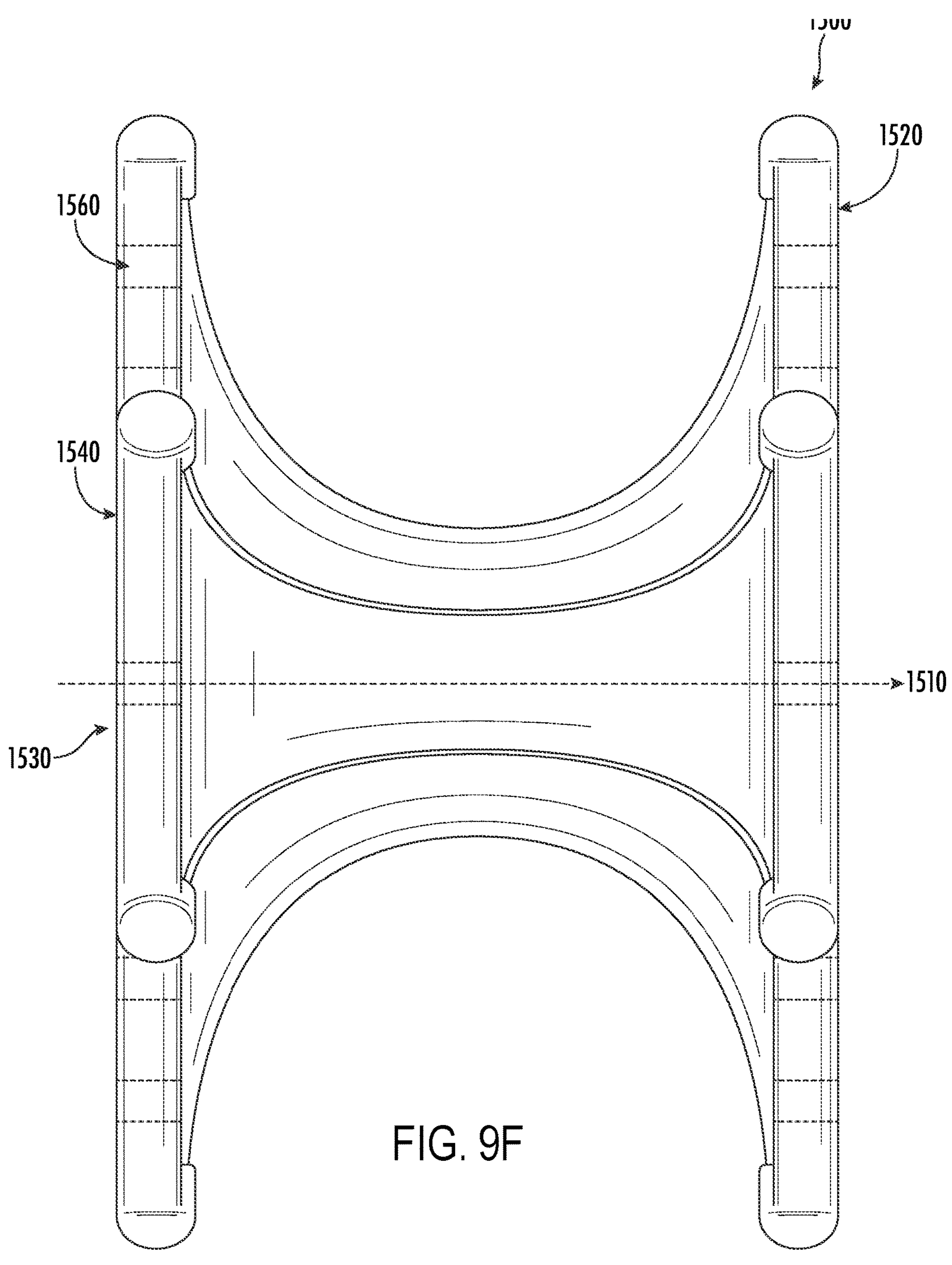

FIGS. 9E and 9F show additional exemplary septum fixation and docking assemblies. For example, in FIG. 9E, the shown atrium member 1500 can be constructed of flexible wiring and have textile materials that are adapted to be compatible with the human body and can be used for atrium septum insertion. Such an exemplary and unlimiting device can also comprise the first portion 1520 and the second portion 1540 that comprises a plurality of magnets 1560. The device has an aperture 1530 configured to receive the disclosed herein catheter and lock it in place.

Figure 9G:
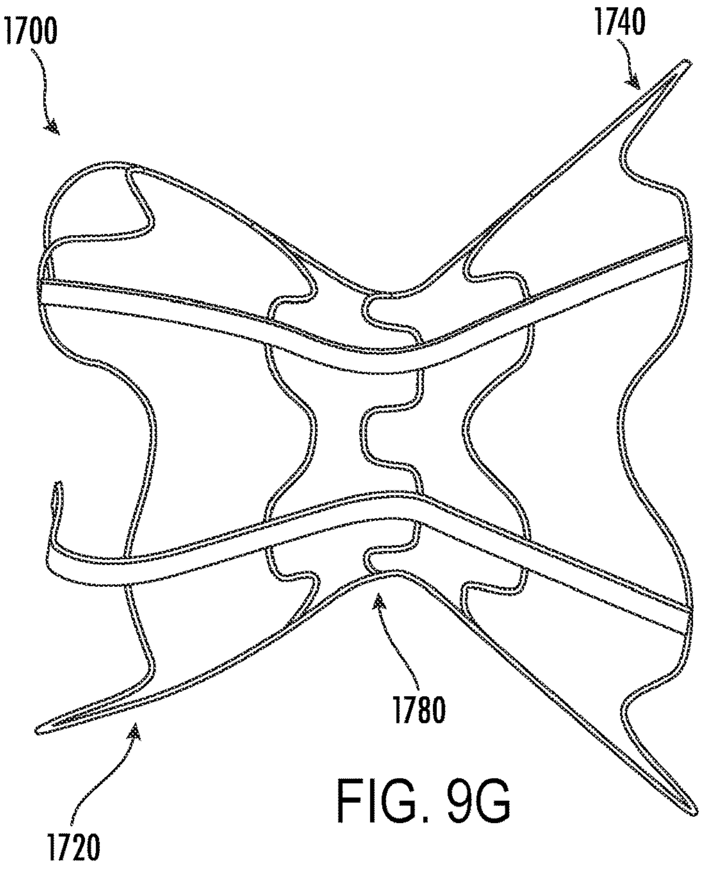
Figure 9H:
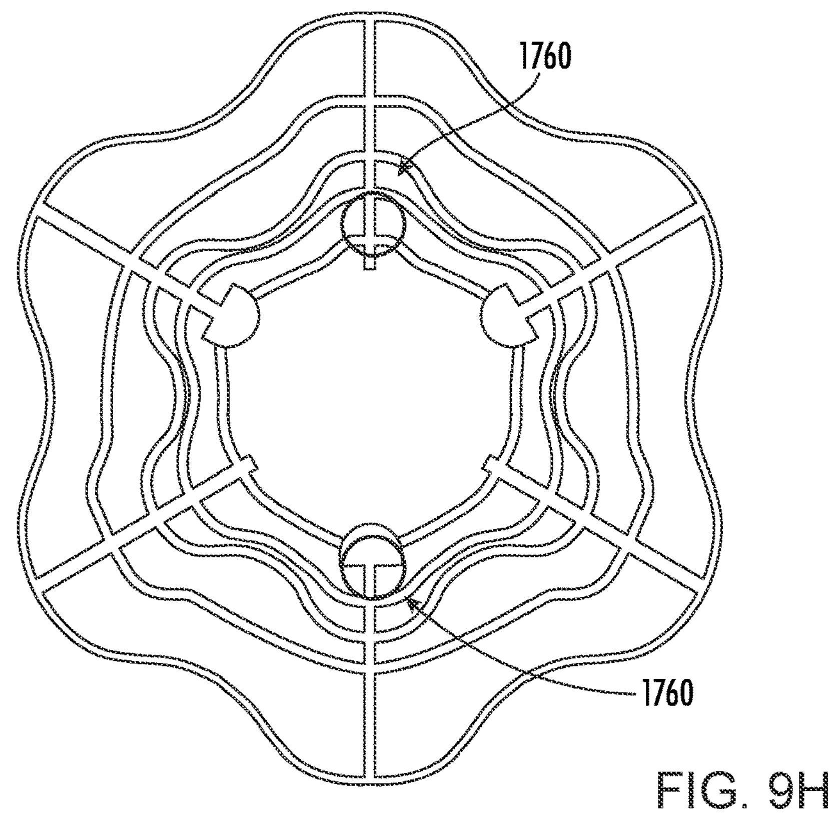

FIGS. 9G-9H show an additional exemplary and unlimiting septum fixation and docking assembly 1700 made of flexible struts configured to be inserted into the atrium septum such that the first portion 1740 is disposed on the left side of the atrium septum and the second portion 1720 is disposed on the right side of the atrium septum. In still further aspects, the second portion 1720 can comprise a plurality of magnets 1760.

Again, as described in detail herein, the disclosed system allows insertion of the septal fixation and docking assembly having one or more magnets during the septostomy. Then the assembly can latch onto the polar component of the plurality of magnets disposed on the catheter, securing it in place. With a maneuver that relies on the magnetic properties of magnets and reversing the polarity, the catheter can be disengaged when the support system is no longer needed, and the septostomy closed with a specially designed plug (all completed endovascularly).

FIG. 10A-10B, as disclosed above, shows exemplary and unlimiting positioning of the catheter within the heart when it is locked in the docking assembly 120.

Some additional positioning of the catheter and the septum fixation and docking assembly are shown in FIGS. 12A-12B. FIG. 12A shows the positioning of the catheter and the septum fixation and docking assembly similar to the one shown in FIG. 11A, while FIG. 12B shows the catheter and the septum fixation and docking assembly similar to the one shown in FIG. 11B.

In still further aspects, disclosed herein is a long-term right ventricular assist system comprising any of the disclosed above catheters; and any of the disclosed above the atrial septal fixation and docking assemblies, wherein the system is configured to effectively offload a failing right ventricular and to promote systemic perfusion with oxygenated blood.

In still further aspects, when the system is positioned within the patient body, the catheter is configured to pass through the aperture of the atrial septum and to be removably fixated within the atrial septal fixation and docking assembly. In still further aspects, the atrial septal fixation and docking assembly are permanently fixated to the atrium septum. In still further aspects, disclosed is a system where the one or more magnets of the atrial septal fixation and docking assembly are removably fixated with a plurality of magnets of the auxiliary member.

It is understood that the one or more magnets of the atrial septal fixation and docking assembly and the plurality of magnets of the auxiliary member can be configured to be tuned to lock the catheter within the assembly or decouple and remove the catheter from the assembly.

The systems disclosed herein can further comprise a blood pump positioned outside of the patient's body. It is understood that the systems can also comprise more than one pump if needed. In yet other aspects, and as described above, the system can comprise a double chamber pump. In yet further aspects, the system can further comprise an oxygenator. In such aspects, the pump is configured to pump the blood through the catheter to the oxygenator to allow blood to be oxygenated and then deliver the oxygenated blood to the left atrium of the patient.

In still further aspects, the system can also comprise a battery. Yet, in other aspects, the system can comprise a controller.

It is understood that the system can be mobile or can be stationary depending on the status of the patient. Some exemplary systems are shown in FIG. 14A-14C. Referring now to FIG. 14A, the disclosed herein catheter 1020 exiting the patient's body into a blood pump 1030, which pumps the blood collected by the inflow lumen into oxygenator 1040 that further delivers oxygenated blood into the outflow lumen to be delivered to the left atrium of the patient. The system can be positioned in the backpack 1000 for the convenience of the patient. The system can further comprise a battery and controller 1060 that can control the rate of blood diffusion depending on the internal pressures measured by the first and the second pressure sensors. Different aspects of such a system are shown in FIGS. 146-14C. FIG. 14B shows the inflow lumen 1020*a* bringing blood to the pump, while the outflow lumen 1020*b* brings oxygenated blood back to the patient's heart, forming a "y-type" configuration as described above In yet other aspects and as shown in FIG. 14C, the mobile system can also be designed as a shoulder harness with the "Fanny Pack." The catheter's lumens 1220 are hosted within the shoulder harness 1210 when battery and controller 1260 are disposed on the waist belt and along with "Fanny Pack" pump 1240. Oxygenators 1222 and 1224 are also hosted within the shoulder harness 1210, along with additional control systems 1228 if needed.

Methods

The present disclosure is also directed to the methods of making the disclosed herein catheters and docking systems as well as methods of using the same. It is understood that the catheter can be made by any known in the art methods. For example, and without limitations, it can be made by disposing the desired layer in the desired sequence on a mandrel and heat treating all the layers to form the desired shape. Yet, in other aspects, the catheter can be made by combining the premade elongated tubings and laminating the desired layers. In yet other aspects, the fenestrations can also be done by any known in the art methods.

In some aspects, the auxiliary member can be formed separately and then fixedly attached to the catheter. While in yet other aspects, the auxiliary member can be made as an integral part of the catheter. It is understood that these described methods are only exemplary, and other known methods for making the catheters can also be employed.

Also, in still further aspects, disclosed herein are methods of inserting and deploying the disclosed herein catheters and systems.

Disclosed are the methods comprising: inserting any of the disclosed above atrial septal fixation and docking assemblies of into an atrium septum and then inserting any of the disclosed above catheters. The methods further comprise reversibly locking the catheter in the disclosed above atrial septal fixation and docking assembly such that the first portion is disposed within a left atrium.

In still further aspects, the atrial septal fixation and docking assembly is first inserted via septostomy and is disposed within the atrium septum. In yet further aspects, the catheter is inserted percutaneously through a right or left internal jugular vein or a subclavian vein. It is understood that any known in venous insertion methods can be utilized. In some unlimiting aspects, for example, the catheter can be inserted using an introducer and wire. It is understood that any conventional methods of introducing the catheter can be utilized.

In still further aspects, the catheter's insertion can be fluoroscopically guided.

In still further aspects, the proximal end of the third portion of the catheter is connected to a pump. The methods further comprise oxygenating blood received from the inflow lumen in an oxygenator and flowing the oxygenated blood through the outflow lumen into a patient body, as disclosed in the aspects above.

EXAMPLES

Example 1: 1.1 Hemodynamic Modeling

Figures 15A, 15B:
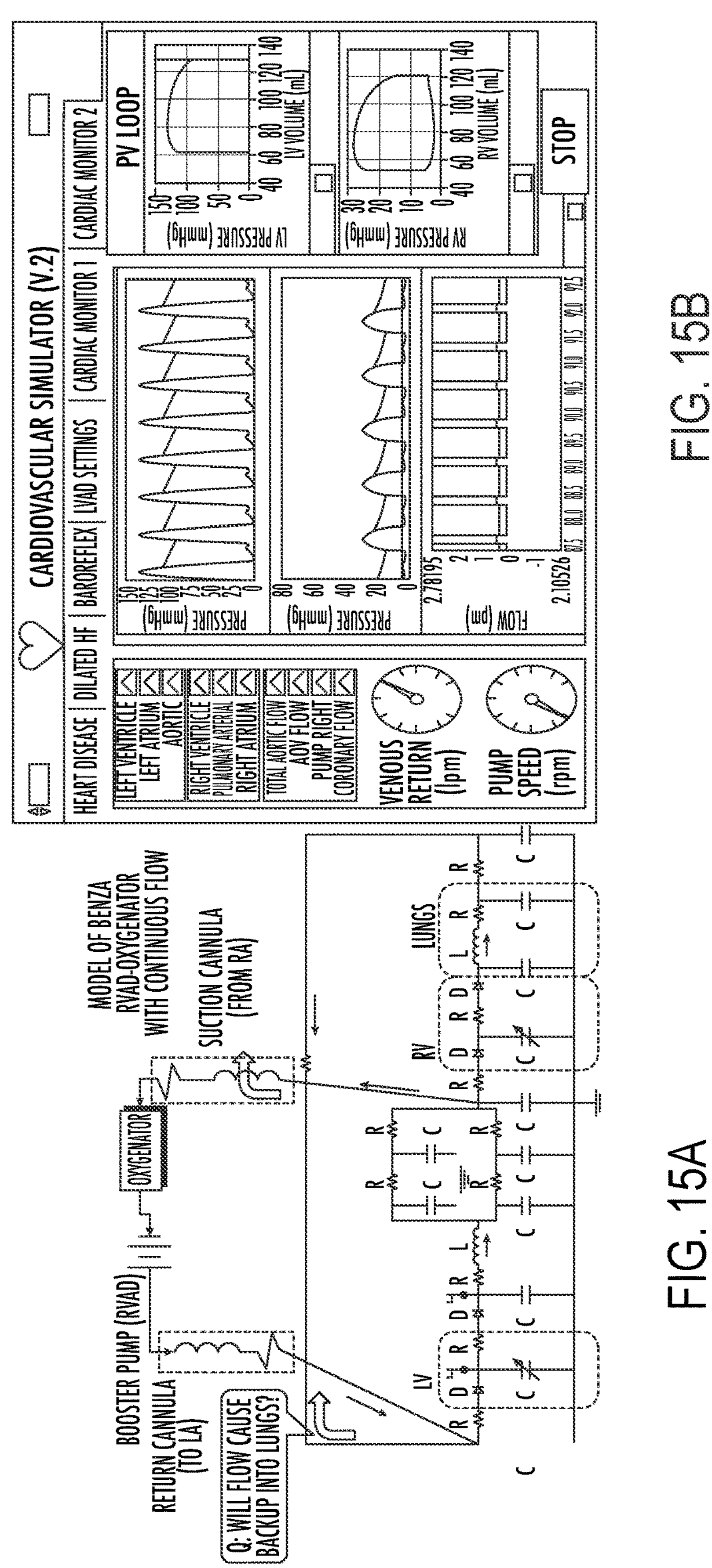
FIGS. 15A-15C show simulated performance of an exemplary catheter in one aspect.

The design and optimization of the indwelling portion of the catheter can be guided by computer simulation of the hemodynamics on two scales. Lumped parameter modeling (aka "one-dimensional") can be performed to identify the optimal sizing of the components based on the necessary pressure, flow, and gas exchange. In tandem, flow visualization can be performed to optimize the specific shape of the catheter tip and its positioning within the atria. The former will employ a lumped-parameter model representation of the circulatory system that includes the first-order cardiovascular compartments, ventricles, atria, and vasculature coupled with a model for the cannula, oxygenator, and external blood pump. (FIGS. 15A-15B.) The simulator represents these elements by electrical analogs: vascular resistance, compliance, and inertance by electrical resistors, capacitors, and inductors, respectively; valves by diodes; and pumping chambers by time-varying capacitors.

Figure 15C:
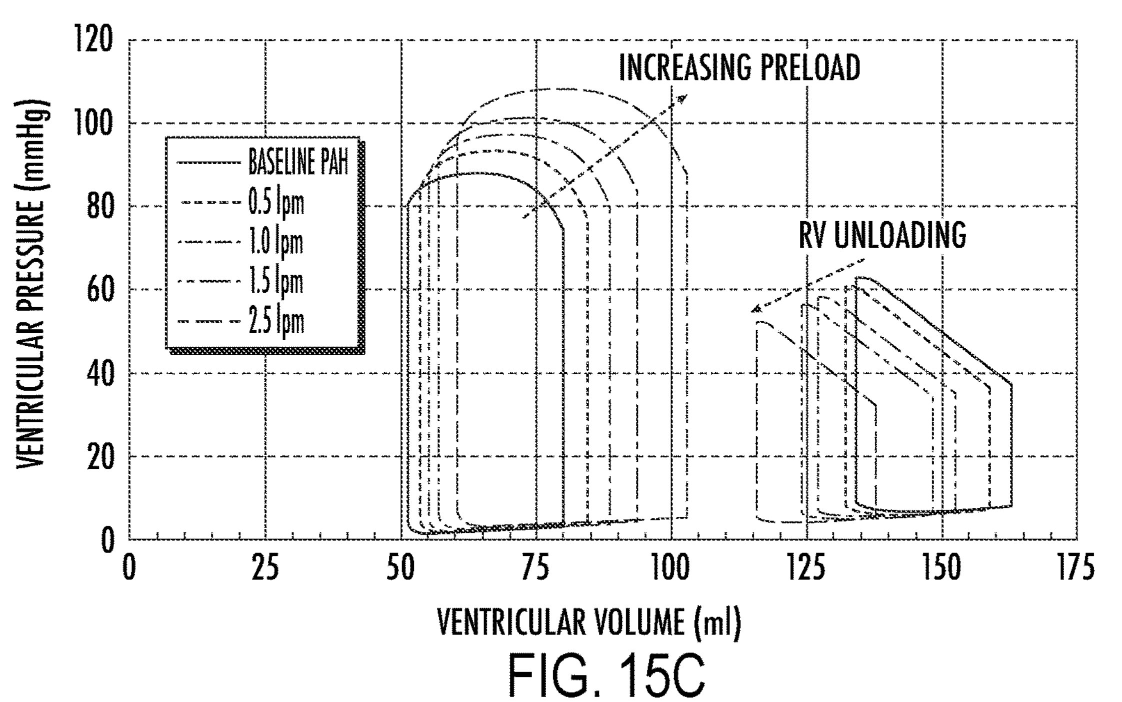

Such studies allow permit computer simulation of the time-varying pressure and flow to be solved on a computer workstation (FIG. 15C). For the current application, the model permits performing virtual experiments (e.g., "ramp" studies) using human parameters—that extrapolate beyond those that could be achieved experimentally.

Preliminary simulation results, provided in FIG. 15C demonstrates the proof of principle of the proposed system: namely, the concomitant unloading of the right ventricle and re-loading the left ventricle in a simulated PAH patient. These results also support the hypothesis that a marked therapeutic effect is achievable with a moderate bypass flow rate (0.5-2.5 lpm).

It is understood that various spectrum of clinical conditions encountered by the inventors clinically (Table 1) can be further stimulated to identify the optimal degree of support as a function of the severity and permutations of the disease. An oxygenator can be added to the simulation to evaluate oxygen transport.

A point of "diminishing returns" for which an adequate therapeutic effect is provided with the least invasive (smallest) catheter and minimally sized pump and oxygenator. These targets can be patient-specific; therefore, the exercise for a range ($5^{th}$-$99^{th}$% ile) of the severity of PAH can be repeated.

TABLE 1

Table 1: Simulation

| | Moderate PAH | +RVAD 0.5 lpm | +RVAD 1.0 lpm | +RVAD 1.5 lpm | +RVAD 2.5 lpm |
|---|---|---|---|---|---|
| mPAP (mmHg) | 50 | 48 | 46 | 45 | 42 |
| C.O. (lpm) | 3.6 | 3.8 | 4.2 | 4.5 | 5.3 |
| LV SV (ml) | 29 | 31 | 33 | 37 | 42 |
| RV SV (ml) | 29 | 27 | 26 | 24 | 22 |
| mLAP | 4 mmHg | 5 | 5 | 6 | 6 |
| mRAP | 8.7 mmHg | 8.0 | 7.2 | 6.7 | 5.6 |

Prophetic Example 2: Flow Visualization

Figure 16:
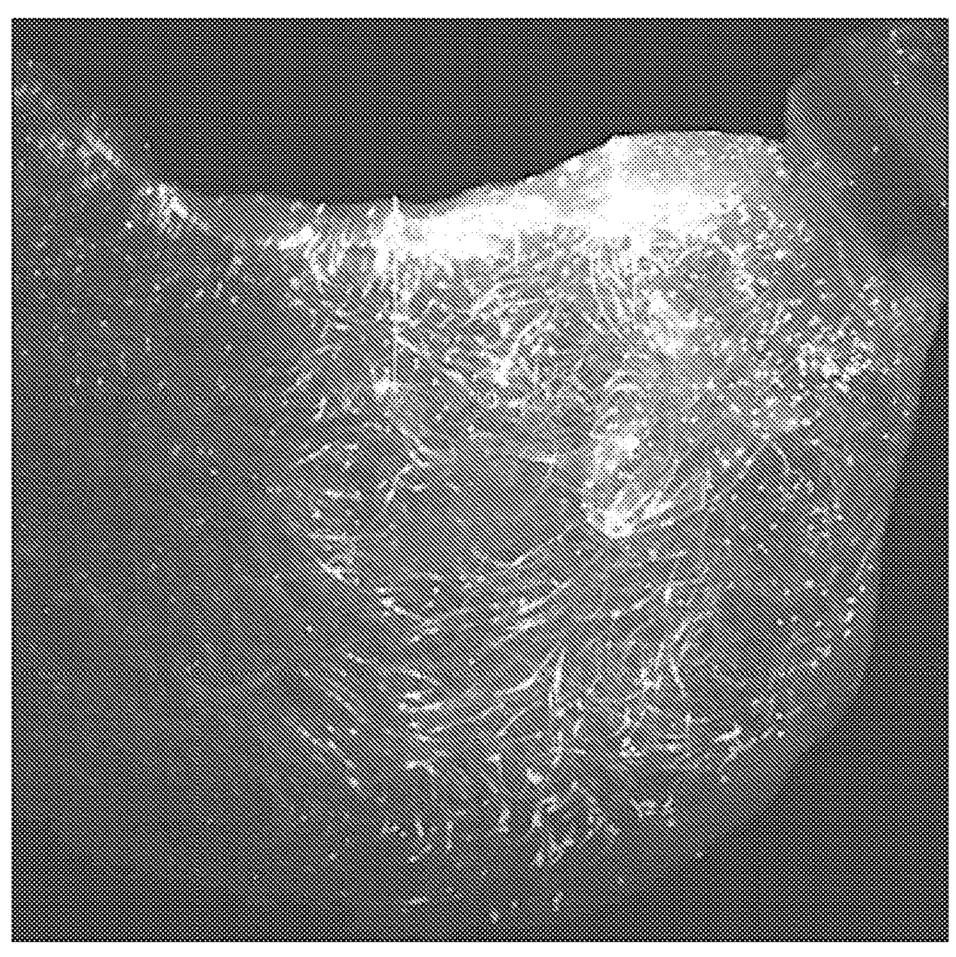
FIG. 16 shows a simulated blood flow delivered by an exemplary catheter to the patient's heart in one aspect.

In tandem with the above simulation studies, physical prototypes of the indwelling portion of the disclosed system can be produced for in-vitro validation in the flow-visualization laboratory. Such experiments allow: to optimize the flow characteristics within the atria and to simulate the procedure of insertion, removal, and positioning of the catheter, using the magnetic docking as described above. An exemplary and unlimiting flow streaklines obtained by such experiments is shown in FIG. 16.

The transparent casts of adult human hearts (dilated and healthy) can be used to conduct such experiments. The additional casts can be produced to assure representative anatomy of PAH patients (e.g., myocardial hypertrophy.) These will be produced from de-identified CT scans using previously developed protocols. Briefly, serial CT images will be segmented reconstructed using commercial CAD software, from which a 3-D printed replica is made.

Prophetic Example 3: Test the Capacity in which the Proposed Pulmonary Support System in a Human PH Model Utilizing Brain Dead, Beating Heart Donors This example will allow demonstrate that in a human brain-dead, beating heart donor model of PH, the system will be initiated and adequately unload the RV and maintain LAP using the paired RA/LA pressure sensors. It will also confirm appropriate device delivery, positioning, secure locking in the septum, and safe removal.

Placement: In certain aspects, to study the effect of the disclosed herein catheter, it can be inserted into the human brain-dead will be obtained, beating heart donors whose families have consented for donation to science.

The ventilated donor would be prepared for a surgery by any known in the art methods. The disclosed herein catheter will be placed in the left internal jugular vein to the right (or left) proximal pulmonary artery. A conductance catheter to generate pressure-volume loops (Science ADVantage, Transonic, Ithaca, NY) will be placed percutaneously from the contralateral femoral vein. Arterial line monitoring will be via the femoral arteries for heart rate (HR), systolic (SBP), diastolic (DBP), and mean arterial pressures (MAP). An initial arterial blood gas will be checked. Ventilator settings will be maintained at 100% FiO2, PEEP 7, rate of 22 as long as saturations remain >95%. A TEE probe will be placed and positioned to visualize the interatrial septum. Initial hemodynamic data will be collected from the PA catheter, including RA pressure (RAP), PA pressure (PAP), pulmonary capillary wedge pressure (WP), and mixed venous blood gas. The RV PV-loop signals provided by the conductance catheter system will be acquired by a data acquisition system (PowerLab 8/35 and LabChart Pro). From the arterial line, blood pressure and arterial blood gas (noting the ventilator settings) will be recorded. TEE measurements will be collected, including LV end-diastolic volume (LVEDV), LV end-systolic volume (LVESV), LA diameter, ejection fraction (LVEF), RV end-systolic volume (RVESV), RV end-diastolic volume (RVEDV), and RV fractional area change (RVFAC). Thereafter, the PA catheter will be withdrawn to the RV. LA pressure will be obtained from a micro-tipped pressure catheter (Millar, Inc.) placed into LA (see below) via thoracotomy.

Thoracotomy and PA Banding: A left anterior thoracotomy will be made, and the left thoracic cavity will be entered. The pericardium will be opened. The main and left pulmonary arteries will be isolated, and a Rommel tourniquet will be placed around these arteries loosely. The LA will be identified, and a sensor will be directly inserted.

Catheter Placement Technique: Using the closed Seldinger technique and ultrasound guidance, access to the right internal jugular vein will be obtained. Weight-based intravenous heparin will then be administered at 150 Units/kg and titrated for an ACT>250 seconds. An atrial septostomy will then be created using fluoroscopy and TEE guidance at the mid-fossa ovael using a Brockenbrough trans-septal needle and confirmed by measuring LA pressure. The atrial septal anchor will then be deployed based on the described parameters. A long guide wire will then be used to cross into the LA and across the mitral valve into the LV. Dilators will then be used to approach the final catheter diameter at the skin surface and entry point of the jugular vein. Using fluoroscopy, the catheter will be delivered over the wire into the right atrium and towards the LA. The magnetic portion of the catheter will then make contact with its opposite poled septal anchor. This will secure the catheter in place and at the correct position in the LA. TEE, fluoroscopy will be used to confirm placement.

Prophetic Example 4: Methods, Initiation of the Circuit, and Effective Unloading A standard primed ECMO circuit with Quadrox oxygenator (Maquet) and Revolution pump (LivaNova) will be brought to the field. ACT will be measured for a goal ACT>250 seconds; given at 150 U/kg initial bolus (from above) and weight-based re-dosing based on ACT. The circuit will be primed and controlled by the AGH perfusionist.

The circuit will be connected so that the catheter outflow (withdrawn from the RA) enters the pump and is oxygenated and re-introduced to the inflow (to the LA.) Oxygenation will be monitored and adjusted throughout by checking serial arterial blood gases. The lines will be designed and connected, and flow will be initiated at a nominal flow rate of 2.0 L/min with collected data from the sources (Swan, Millar, LA pressure sensor). The RAP from the pulmonary catheter will be used to compare with the RAP determined by the transseptal catheter sensor. RV PV-loop signals from the conductance catheter will continue to be recorded along with the LA pressure from the previously placed pressure catheter. From the arterial line blood pressure and arterial blood gas (noting the ventilator settings) will be recorded. TEE measurements as in 2.1 will be recorded. Laboratories will be completed (chemistries, lactic acid, and LFTs).

The flow will be adjusted in 1 L increments up to 4 L/min, and data will be collected. Each collection period should last at least 2 minutes to allow for equilibration of hemodynamics. After this baseline assessment, the pump will be stopped. The Rommel tourniquet will be used and occlude the PA and monitor the swan to ensure the appropriate acute changes in hemodynamics are expected. The ECMO pump will then be started again at 2 L, and measurements will be repeated in the same fashion. If this segment of the assessment goes well, it will be repeated only this time, partially occluding the main PA, particularly if the PV loops did not change significantly between the $1^{st}$ and $2^{nd}$ assessments.

The ECMO circuit will be turned off; the catheter will be separated from its interatrial locking mechanism and removed. The LA pressure sensor and tourniquets will be removed, and the thoracotomy closed. This will be the end of the procedure, and the donor will be handled per CORE protocol.

The proposed experiments will allow the placement of the catheter. After placement and initiation, the PV loops will resemble those from the simulation studies (FIG. 15C). The RA and LAP sensors on the PHope Catheter will correlate with the PA catheter and surgically placed standard LAP monitor at any given flow. The other hemodynamic/structural measurements obtained from the PA catheter and echocardiography can correlate with the physiologic response to loading/unloading of the RV and LV (higher flow=unloading RV and loading LV, lower flow=loading RV and unloading of LV).

If after the catheter is removed from the magnetic coupler, an unacceptable inter-atrial flow (leakage) can occur. To avoid such undesirable results, a miniature duck-bill valve into an anchor or insert a magnetic plug into the orifice using a guidewire introduced through the disclosed catheter prior to its removal.

Prophetic Example 5: Compare the Short-Term Efficacy of a PHope Support System Vs. Traditional VA ECMO in a Chronic Animal Model of PH The efficacy of the PHope Catheter in comparison to conventional VA ECMO to (i) unload the RV and PAs, (ii) restore normal CO, (iii) maintain normal arterial blood gases and tissue perfusion, and (iv) monitor diastolic LV function. A cohort of sheep with chronic PH and RV failure will be supported either on VA ECMO (control) or the disclosed herein system for four hours. Data will focus on RV function, CO, arterial oxygenation, and LAP. Another cohort of sheep with chronic PH will then be supported either on VA ECMO or the system disclosed herein for a period of 2 weeks with the same focus on data but including further assessment of RV recovery.

Prophetic Example 6: Sheep Model of Pulmonary Hypertension and RV Failure

The sheep model of pulmonary hypertension will be created by progressive pulmonary artery banding, with a goal of reaching proximal mean pulmonary artery pressures of 50-60 mmHg. The Lange model will be adapted to achieve this level of PH. Progressive PA banding avoids the acute inflammatory responses to embolization that cause transient increases in PVR, respiratory distress, RV failure, and mortality, yet will create a hypertensive/hypertrophied RV that will enable the study of the catheter in a more realistic heart. This model can show the generation of systolic PA pressure of up to 100 mmHg within one month and 125 mmHg within two months.

A left thoracotomy will be performed on sheep weighing 50-60 kg. The left PA will be ligated, and an inflatable cuff occluder will be placed on the main PA (now effectively the right PA) to control PVR. PA and aortic flow probes will also be placed for measuring PA and aortic flow in later experiments. A PA catheter will also be placed via the left internal jugular vein, and a conductance catheter will be placed into the RV via the right internal jugular vein for regular measurement. Both catheters will be tunneled to the sheep's back, and the sheep will be recovered. Two days following surgery, the PA occluder will be inflated to begin increasing the PA pressure proximal to the cuff. The cuff will be inflated to increase the mean PAP by approximately 1 mmHg every other day for the first 24 days, 0.5 mmHg every other day over the next 24 days, and then 0.5 mmHg per day every three days thereafter. The rate of banding will be reduced as necessary upon signs of significant dyspnea, with an emphasis on reducing mortality over achieving rapid development of PH. Oxygen will be delivered via facemask upon any signs of dyspnea following increased PA occlusion, and standard euthanasia criteria will be employed. Without wishing to be bound by any theory, it is speculated that a mean PAP of approximately 25-30 mmHg following LPA occlusion and up to another 20 mmHg increase via progressive PA occlusion can be achieved. This will require significant care and attention but should be achievable based on the inventors' previous experience.

Prophetic Example 7: Testing of Trans-Septal ECMO Support System—4-Hour Testing

The methods for this experiment will be similar to those used in several ovine ECMO and PA-LA artificial lung studies previously conducted by the inventors. Each sheep with PH will be anesthetized, intubated, and mechanically ventilated using 1-5% isoflurane. All cardiac instrumentation will be placed via a thoracotomy. Neck cutdowns will be used for jugular venous and carotid artery access. A 100 U/kg bolus of intravenous heparin will be administered, and an arterial line will be placed in the left carotid artery. Under fluoroscopic guidance, endovascular wires will be used to access the right atrium with a catheter. Placement of the ECMO circuit will depend on the support mode being tested below.

Placement of PAHope Catheter: Using previously described techniques, an atrial septostomy will be made with guidance from a transesophageal echocardiogram and fluoroscopy.

The septum will be crossed with a catheter to enter the left atrium, and the septal fixation and docking assembly will be inserted. Following this, a stiff wire will be replaced to maintain access through the anchor and in the left atrium. The disclosed herein PHope Catheter will then be carefully guided into the left atrium and anchored to the septum by a magnetic field between the plurality of magnets on the assembly and the catheter as described above. Each lumen of the catheter will be appropriately connected to a standard ECMO circuit using a Quadrox oxygenator with a commercial centrifugal pump (e.g., Centrimag or Maquet revolution).

Placement of ECMO circuit: control group: A cut-down will be used to place a 24 Fr venous drainage catheter via the right internal jugular and a 16 Fr arterial reinfusion catheter via the carotid artery. The catheters will be appropriately connected to the same ECMO circuit as the trans-septal system.

Common methods: Prior to initiating ECMO flow, an acute increase in the PVR to induce RV failure will be generated. This will be achieved by restricting the main PA until CO falls by 40-50% to model an acute-on-chronic insult and RV failure. From previous experience, it is expected that these sheep are stable for short periods (s two hours) under anesthesia with up to 50% reduction in cardiac output. To avoid any sudden death, however, ECMO support will be initiated immediately after creating RV failure since cannulation will have been done prior to the insult. ECMO circuit flow will be maintained at 2-2.5 L/min of flow with a sweep gas flow rate of 5 L/min of 95% O2 and 5% CO2 gas. The combination of elevated sweep flow and 5% $CO_2$ maintains the gas flow paths free of excessive condensation and maintains normal arterial $PCO_2$ in sheep with normal respiratory function. In each case, the sheep will be given 0.5 g of Solumedrol within the circuit prime to control for any changes in pulmonary resistance due to blood-biomaterial-induced inflammation. The ACT will be maintained between 200-400 seconds for the duration of the study using a heparin drip.

The sheep will be supported in this fashion for 4 hours. Over the course of the experiment, heart rate; systolic (SBP), diastolic (DBP), and mean arterial (MAP), pulmonary arterial systolic (PAS), pulmonary arterial diastolic (PAD), pulmonary arterial mean (PAM), and right ventricular systolic, diastolic, and mean blood pressure (RVSP, RVDP, RVMP); central venous pressure (CVP); left atrial pressure via the novel transducer (LAP/LVEDP); pulmonary artery pressure index (PAPI); cardiac output (CO); RV volume; PA, circuit, and proximal aortic flow rate; and pump speed (RPMs) will be recorded prior to initiating acute RV failure, after initiating RV failure and every hour after starting circuit flow. A data acquisition system will be used to record RV, PA, CV, and LA pressures and PA flow rate waveforms at 250 Hz. Arterial, venous, circuit inlet and outlet blood gases and total hemoglobin; ACT; platelet and white cell counts; and plasma free hemoglobin concentrations will be measured prior to initiating acute RV failure, after initiating RV failure, and every hour thereafter. Transesophageal echocardiography will be performed upon initiation of anesthesia to record indices of RV size and performance, including RVSP, RV end-diastolic, and end-systolic areas (RVEDA and RVESA), RV fractional area change (RVFAC), RV free wall thickness, and tricuspid annular plane systolic excursion (TAPSE). The other heart dimensions, including RA, LA, and LV size, as well as LVEF (%), will be measured, and interatrial septal position will be documented.

Following four hours of support, each sheep will be euthanized with the catheter still implanted and undergo a necropsy to examine the placement of the catheter within the heart. The hearts will be examined, and further evidence of RV remodeling that occurred grossly during the development of PH in this ovine model by weighing the RV-free wall and left ventricle (LV), including the septum, will be recorded, and the RV to LV weight ratio will also be calculated. This will be compared to the TEE estimated values of RV morphology recorded above for further confirmation of the RV remodeling.

Prophetic Example 8: Data Analysis and Outcome Measures

Device blood flow resistance and $O_2$ transfer rates will be calculated according to previously published methods. During trans-septal ECMO, there is the possibility of leakage back through the septum if the catheter does not seat effectively. As such, the cardiac output will be approximated by the aortic flow rate with the understanding that this will not capture coronary artery flow. This study is solely examining the effectiveness of the disclosed herein support in a short-term setting prior to embarking on 14 days studies. The values of i) systolic, diastolic, and mean RV pressures, ii) LAP, iii) cardiac output, iv) arterial blood gases, and v) hemolysis and platelet counts will be compared vs. time using a linear mixed model with repeated measures within SPSS. In particular, particular attention to the change in values between initial RV failure and after initiation of ECMO support will be paid. An effective system will reduce RV pressures and maintain normal cardiac output, LAP, and blood gases, and have a low degree of hemolysis and platelet losses.

Prophetic Example 9

Without wishing to be bound by any theory, it is hypothesized that the trans-septal system will lead to a significant decrease in systolic RVP and an increase in CO while maintaining normal LAP and arterial blood gases.

14-Day In-Vivo Validation of PHope Supported ECMO System:

The methods for this experiment will be similar to those used in several long-term sheep ECMO and PA-LA artificial lung studies within previously employed by the inventors. Placement of the ECMO system and venous and carotid artery lines will proceed as described above. ECMO circuit flow will be maintained at 2-2.5 L/min with a sweep gas flow rate of 5 L/min of 95% O2 and 5% CO2 gas, and ACT will be maintained between 180-240 seconds for the duration of the study using a heparin drip.

The sheep will be supported in this fashion for 14 days. The external portion of the catheter will be securely fixed and directed to the sheep's flank to minimize tampering with the apparatus. The sheep will be recovered from anesthesia and transported to a stanchion, and monitored with 24-hour care over the course of 14 days. This will ensure that the system is not damaged by the sheep and that the animal is appropriately supported physically and medically. The ACT will be checked every 12 hours or as needed for heparin dosage adjustment. Complete blood cell counts and plasma-free hemoglobin will be taken every day, and a blood chemistry panel will be taken prior to starting the study and on days 3, 7, and 14 days. In the first 48 hours, measurements will be obtained every 4 hours that include heart rate; systolic (SBP), diastolic (DBP), and meanarterial (MAP), left atrial pressure via the novel transducer (LAP/LVEDP); CO: pump speed (RPMs); and arterial blood gases and then every 12 hours after that. Adjustments to pump flows will be made as clinically determined to support the sheep. On day 3, 7, and 14, a transthoracic echocardiogram will also be performed to record indices of RV size and performance, including RVSP, RV end-diastolic and end-systolic areas (RVEDA and RVESA), RV fractional area change (RVFAC), RV free wall thickness, and tricuspid annular plane systolic excursion (TAPSE). The heart dimensions, including RA, LA, and LV size, as well as LVEF (%), will be measured, and interatrial septal position with be documented. A conductance catheter will also be placed into the RV using fluoroscopy to measure the RV PV-loop.

Following 14 days of support, each sheep will be euthanized and undergo a necropsy to examine gross and microscopic pathology in the heart, lungs, liver, spleen, and kidneys. To determine if RV remodeling occurred, the RV free wall and left ventricle (LV), including the septum, will be weighed, and the RV to LV weight ratio will be calculated.

Data Analysis and Outcome Measures:

Device blood flow resistance and $O_2$ transfer rates will be calculated according to previously published methods. During VA ECMO, the aortic flow rate will not be equal to the cardiac output. Therefore, cardiac output will be assumed to be equal to ECMO circuit flow rate plus PA flow rate. During trans-septal ECMO, there is the possibility of leakage back through the septum if the catheter does not seat effectively. As such, the cardiac output will be approximated by the aortic flow rate with the understanding that this will not capture coronary artery flow.

The longitudinal data for both groups will be compared using repeated measures mixed models in SPSS to determine significant differences between RA-LA trans-septal support and traditional VA ECMO. Particular attention will be paid to differences in i) systolic, diastolic, and mean RV pressures, ii) CO, and iii) arterial blood gases, and iv) hemolysis and platelet counts between the two treatments modes. An effective system will reduce RV pressures and maintain normal cardia output, LAP, and blood gases and minimize hemolysis and platelet losses Lastly, to assess the extent of reverse RV remodeling during chronic support, the RV to LV weight ratio in each group will be compared with historic data from healthy sheep and the values from the acute studies using one-way ANOVA.

Without wishing to be bound by any theory, it is hypothesized that the trans-septal system will provide a statistically similar reduction in RV pressures and arterial blood gases as VA ECMO, as the right to left flow rates will be the same. Still further and again wishing to be bound by any theory, it is hypothesized that the trans-septal system will better maintain CO by providing more normal LV filling and preload. The trans-septal method will also enable pumping to the low-pressure LA, which reduces the mean pressure head on the pump by approximately 80 mmHg. This will lead to lower pump RPMs, lower blood shear stress, and lesser hemolysis and platelet activation. Lastly, it is further hypothesized that the sheep can be supported for 14 days with significant RV unloading, as measured by significantly lower RVP and good RV and LV function as measured by a normal cardiac output.

EXEMPLARY ASPECTS

In view of the described processes and compositions, hereinbelow are described certain more particularly described aspects of the disclosures. These particularly recited aspects should not, however, be interpreted to have any limiting effect on any different claims containing different or more general teachings described herein, or that the "particular" aspects are somehow limited in some way other than the inherent meanings of the language and formulas literally used therein.

EXAMPLE 1: A catheter comprising: a first portion having a proximal end and a distal end, a second portion having a proximal end and a distal end, and a third portion having a proximal end and a distal end; wherein the first and the second portions comprise an outflow lumen; wherein the third portion comprises an inflow lumen and the outflow lumen; wherein the first portion has a helical portion having a first length and extending from the distal end of the first portion toward the distal end of the second portion; and wherein the catheter is configured to be inserted into a patient body such that the first portion penetrates an atrial septum to extend into a left atrium to assist with systemic perfusion with oxygenated blood.

EXAMPLE 2: The catheter of any examples herein, particularly example 1, wherein the inflow lumen has an elongated tubular body having a proximal end and a distal end and has a first diameter and configured to withdraw oxygen-depleted blood from a patient; and the outflow lumen has an elongated tubular body having a proximal end, a distal end and has a second diameter and configured to deliver oxygen-rich blood to the patient; wherein the first diameter is greater than the second diameter; wherein at least a portion of the elongated tubular body of the outflow lumen is disposed within at least a portion of the elongated tubular body of the inflow lumen; and wherein the distal end of the outflow lumen extends beyond the distal end of the inflow lumen.

EXAMPLE 3: The catheter of any examples herein, particularly example 1 or 2, wherein the inflow lumen has a first outer layer defining an outer surface of the elongated tubular body of the inflow lumen of the catheter and a first inner layer defining an inner surface of the elongated tubular body of the inflow lumen; and wherein the outflow lumen has a second outer layer defining an outer surface of the elongated tubular body the outflow lumen and a second inner layer defining an inner surface of the elongated tubular body of the outflow lumen.

EXAMPLE 4: The catheter of any examples herein, particularly examples 2-3, wherein the first outer layer, first inner layer, second outer layer, and the second inner layer are the same or different.

EXAMPLE 5: The catheter of any examples herein, particularly examples 2-4, wherein the elongated tubular body of the outflow lumen is positioned within at least a portion of the elongated tubular body of the inflow lumen such that a center of the outflow lumen is offset of a center of the inflow lumen.

EXAMPLE 6: The catheter of any examples herein, particularly examples 2-5, wherein the elongated tubular body of the outflow lumen is positioned within at least a portion of the elongated tubular body of the inflow lumen such that a center of the outflow lumen and a center of the inflow lumen substantially overlap.

EXAMPLE 7: The catheter of any examples herein, particularly examples 2-6, wherein the distal end of the outflow lumen is substantially the same as the distal end of the first portion and wherein the distal end of the inflow lumen is substantially the same as the distal end of the third portion.

EXAMPLE 8: The catheter of any examples herein, particularly examples 1-7, wherein the proximal end of the first portion extends into the distal end of the second portion and wherein the distal end comprises an outlet of the outflow lumen.

EXAMPLE 9: The catheter of any examples herein, particularly example 8, wherein the distal end of the first portion is tapered.

EXAMPLE 10: The catheter of any examples herein, particularly examples 1-9, wherein the proximal end of the second portion extends into the distal end of the third portion and wherein the proximal end of the third portion comprises an outlet of the inflow lumen.

EXAMPLE 11: The catheter of any examples herein, particularly examples 1-10, wherein the helical portion of the first portion follows a helical path having a pitch from 0 mm to about 30 mm.

EXAMPLE 12: The catheter of any examples herein, particularly examples 1-11, wherein the helical portion has an initial curvature radius from about 2 mm to about 30 mm.

EXAMPLE 13: The catheter of any examples herein, particularly examples 1-12, wherein the helical portion comprises from about 0.2 to about 1.5 revolutions.

EXAMPLE 14: The catheter of any examples herein, particularly examples 1-13, wherein the helical portion of the first portion comprises a first plurality of fenestrations configured to prevent jet impingement on an endocardial surface of the left atrium and pulmonary veins.

EXAMPLE 15: The catheter of any examples herein, particularly example 14, wherein the first plurality of fenestrations are disposed around a circumference of the first portion in a predetermined or a random pattern.

EXAMPLE 16: The catheter of any examples herein, particularly examples 14 or 15, wherein the first plurality of fenestration comprises from 2 to 25 fenestrations.

EXAMPLE 17: The catheter of any examples herein, particularly examples 9-16, wherein each of the first plurality of fenestrations has the same or a different diameter.

EXAMPLE 18: The catheter of any examples herein, particularly examples 1-17, wherein when the catheter is introduced into the patient body, the first portion of the catheter is positioned within the left atrium such that there is substantially no contact with the natural anatomy of the left atrium.

EXAMPLE 19: The catheter of any examples herein, particularly examples 1-18, wherein when the catheter is introduced into the patient's body, the distal end of the first portion faces downward to a mitral valve and away from a pulmonary vein.

EXAMPLE 20: The catheter of any examples herein, particularly examples 1-19, wherein the first portion comprises a first pressure sensor.

EXAMPLE 21: The catheter of any examples herein, particularly example 20, wherein the first pressure sensor is disposed within 0 to about 30 mm from the distal end of the second portion towards the first portion.

EXAMPLE 22: The catheter of any examples herein, particularly examples 14-21 wherein the first portion comprises at least a portion that is substantially free of any fenestrations.

EXAMPLE 23: The catheter of any examples herein, particularly example 22, wherein the at least a portion of the first portion that is substantially free of any fenestrations has a length that is the same or different from the first length.

EXAMPLE 24: The catheter of any examples herein, particularly examples 1-23, wherein when the catheter is inserted into the patient body, the proximal end of the first portion is positioned on a left side of the atrium septum.

EXAMPLE 25: The catheter of any examples herein, particularly examples 1-24, wherein the second portion has a second length.

EXAMPLE 26: The catheter of any examples herein, particularly examples 1-25, wherein when the catheter is inserted into the patient body, at least a portion of the second portion is positioned within a right atrium.

EXAMPLE 27: The catheter of any examples herein, particularly examples 1-26, wherein when the catheter is inserted into the patient body, the distal end of the second portion is positioned on a right side of the atrium septum.

EXAMPLE 28: The catheter of any examples herein, particularly examples 1-27, wherein the proximal end of the second portion extends into the distal end of the third portion, wherein the distal end of the third portion is tapered.

EXAMPLE 29: The catheter of any examples herein, particularly examples 1-28, wherein the catheter comprises an auxiliary member positioned radially outward of the distal end of the second portion and wherein the auxiliary member is configured to removably attach the catheter to the atrium septum.

EXAMPLE 30: The catheter of any examples herein, particularly example 29, wherein the auxiliary member has a diameter greater than a diameter of the first and/or second portions.

EXAMPLE 31: The catheter of any examples herein, particularly examples 29 or 30, wherein the auxiliary member has a diameter greater, smaller, or substantially the same as a diameter of the third portion.

EXAMPLE 32: The catheter of any examples herein, particularly examples 29-31, wherein the auxiliary member has a predetermined length along the second length of the second portion.

EXAMPLE 33: The catheter of any examples herein, particularly examples 29-32, wherein the auxiliary member comprises a plurality of magnets, wherein at least two of the plurality of magnets have opposite polarity.

EXAMPLE 34: The catheter of any examples herein, particularly examples 1-33, wherein the third portion has a diameter larger than a diameter of the first portion and/or second portion.

EXAMPLE 35: The catheter of any examples herein, particularly examples 1-34, wherein the third portion comprises a portion having a second plurality of fenestrations, wherein the portion having the second plurality of fenestrations abuts the distal end of the third portion and has a third length.

EXAMPLE 36: The catheter of any examples herein, particularly example 35, wherein the second plurality of fenestrations are configured to prevent suction of the atrial wall.

EXAMPLE 37: The catheter of any examples herein, particularly example 35 or 36, wherein the second plurality of fenestrations are disposed circumferentially of the inlet lumen positioned in the third portion and wherein the outlet lumen positioned within the inlet lumen in the third portion is substantially free of any fenestrations.

EXAMPLE 38: The catheter of any examples herein, particularly examples 35-37, wherein the second plurality of fenestrations are disposed in a predetermined or a random pattern.

EXAMPLE 39: The catheter of any examples herein, particularly examples 35-38, wherein the second plurality of fenestrations comprise from 4 to 30 fenestrations.

EXAMPLE 40: The catheter of any examples herein, particularly examples 35-39, wherein each of the second plurality of fenestrations has the same or a different diameter.

EXAMPLE 41: The catheter of any examples herein, particularly examples 35-40, wherein the first and the second plurality of fenestrations are different.

EXAMPLE 42: The catheter of any examples herein, particularly examples 35-41, wherein the third portion and/or second portion comprises one or more second pressure sensors.

EXAMPLE 43: The catheter of any examples herein, particularly example 42, wherein the one or more second pressure sensors are not in close proximity to the second plurality of fenestrations.

EXAMPLE 44: The catheter of any examples herein, particularly examples 42 or 43, wherein the one or more second pressure sensors are disposed at least 10 mm away from the second plurality of fenestrations.

EXAMPLE 45: The catheter of any examples herein, particularly examples 1-44, wherein the third portion has at least a portion that is substantially free of any fenestrations.

EXAMPLE 46: The catheter of any examples herein, particularly examples 1-45, wherein when the catheter is inserted into the patient body, at least a portion of the third portion is positioned within the right atrium.

EXAMPLE 47: The catheter of any examples herein, particularly example 46, wherein the at least a portion of the third portion that is positioned within the right atrium is at least a portion of the portion having the second plurality of fenestrations.

EXAMPLE 48: The catheter of any examples herein, particularly examples 1-47, wherein when the catheter is inserted into the patient body, at least a portion of the third portion is positioned within the superior vena cava.

EXAMPLE 49: The catheter of any examples herein, particularly example 48, wherein at least a portion of the third portion that is positioned within superior vena cava is substantially free of the second plurality of fenestrations.

EXAMPLE 50: The catheter of any examples herein, particularly examples 1-49, wherein the first and/or second outer layer comprises a polymeric material comprising reinforced polyurethane, styrene-based elastomer, polyolefin-based elastomers (POE), polyethylene terephthalate (PET), polytetrafluoroethylene (PTFE), ethylene-vinyl acetate (EVA), fluorinated ethylene propylene (FEP), polyether block amide (PEBAX), or any combination thereof.

EXAMPLE 51: The catheter of any examples herein, particularly examples 1-50 wherein the first and/or second inner layer comprises a reinforced polyurethane, styrene-based elastomer, polyolefin-based elastomers (POE), polyethylene terephthalate (PET), polytetrafluoroethylene (PTFE), ethylene-vinyl acetate (EVA), fluorinated ethylene propylene (FEP), polyether block amide (PEBAX), or any combination thereof.

EXAMPLE 52: The catheter of any examples herein, particularly examples 1-51, wherein the catheter further compromises a reinforcing layer.

EXAMPLE 53: The catheter of any examples herein, particularly example 52, wherein the reinforcing layer is substantially encapsulated within the outer layer.

EXAMPLE 54: The catheter of any examples herein, particularly example 52, wherein the reinforcing layer is disposed between the outer layer and the inner layer.

EXAMPLE 55: The catheter of any examples herein, particularly examples 52-54, wherein the reinforcing layer comprises a braid, a metal frame, or any combination thereof.

EXAMPLE 56: The catheter of any examples herein, particularly example 55, wherein the braid comprises a flat-wound wire.

EXAMPLE 57: The catheter of any examples herein, particularly example 55, wherein the metal frame comprises a laser-cut hypotube.

EXAMPLE 58: The catheter of any examples herein, particularly examples 52-58, wherein the reinforcing layer comprises stainless steel or nitinol.

EXAMPLE 59: The catheter of any examples herein, particularly examples 1-58, wherein the catheter is substantially kink-free.

EXAMPLE 60: The catheter of any examples herein, particularly examples 1-59, wherein the inner and/or the outer layer further comprises a pharmaceutically active agent.

EXAMPLE 61: The catheter of any examples herein, particularly example 60, wherein the pharmaceutically active agent comprises at least one of an antibiotic agent, antithrombotic agent, or any combination thereof.

EXAMPLE 62: The catheter of any examples herein, particularly examples 1-61, wherein the catheter is configured to support up to about 4/L min of the blood.

EXAMPLE 63: An atrial septal fixation and docking assembly comprising: a atrial member having a predetermined length, a first portion and a second portion; wherein the atrial member has a crimped profile having a first diameter and an expanded profile having a second diameter, wherein the second diameter is greater than the first diameter; wherein when the atrial member is inserted into an atrial septum to form an aperture of a predetermined dimension in the atrial septum, the first portion is fixated to a left side of the atrial septum, and the second portion is fixated to a right side of the atrial septum, wherein the atrial member encapsulates the aperture such that there is substantially no change in the predetermined dimension of the aperture for a predetermined period of time: and wherein the atrial member is configured to be delivered to the atrial septum in the crimped profile, and when the atrial member is removably fixated with the atrial septum, the atrial member is present in the expanded profile.

EXAMPLE 64: The atrial septal fixation and docking assembly of any examples herein, particularly example 63, wherein the second portion of the atrial member comprises one or more magnets.

EXAMPLE 65: A long-term right ventricular assist system comprising: a) the catheter of any examples herein, particularly examples 1-62, and b) the atrial septal fixation and docking assembly of any examples herein, particularly examples 63 or 64, wherein the system is configured to effectively offload a failing right ventricular and to promote systemic perfusion with oxygenated blood.

EXAMPLE 66: The long-term right ventricular assist system of any examples herein, particularly example 65, wherein when the system is positioned within the patient body, the catheter is configured to pass through the aperture of the atrial septum and to be removably fixated within the atrial septal fixation and docking assembly.

EXAMPLE 67: The long-term right ventricular assist system of any examples herein, particularly examples 65 or 66, wherein the atrial septal fixation and docking assembly is permanently fixated to the atrium septum.

EXAMPLE 68: The long-term right ventricular assist system of any examples herein, particularly example 67, wherein the one or more magnets of the atrial septal fixation and docking assembly are removably fixated the plurality of magnets of the auxiliary member.

EXAMPLE 69: The long-term right ventricular assist system of any examples herein, particularly example 68, wherein the one or more magnets of the atrial septal fixation and docking assembly and the plurality of magnets of the auxiliary member are configured to be tuned to lock the catheter within the assembly or decouple and remove the catheter from the assembly.

EXAMPLE 70: The long-term right ventricular assist system of any examples herein, particularly examples 65-69, wherein the system further comprises a blood pump.

EXAMPLE 71: The long-term right ventricular assist system of any examples herein, particularly examples 65-70, wherein the system further comprises an oxygenator.

EXAMPLE 72: The long-term right ventricular assist system of any examples herein, particularly examples 65-71, further comprises a battery and a controller.

EXAMPLE 73: A method comprising: a) inserting the atrial septal fixation and docking assembly of any examples herein, particularly examples 63 or 64; b) inserting the catheter of any examples herein, particularly examples 1-62; and c) reversibly locking the first portion in the atrial septal fixation and docking assembly such that the first portion is disposed within a left atrium.

EXAMPLE 74: The method of any examples herein, particularly example 73, wherein the atrial septal fixation and docking assembly is inserted via septostomy.

EXAMPLE 75: The method of any examples herein, particularly examples 73-74, wherein the catheter is inserted percutaneously through a right or left internal jugular vein or a subclavian vein.

EXAMPLE 76: The method of any examples herein, particularly example 75, wherein the insertion is fluoroscopically guided.

EXAMPLE 77: The method of any examples herein, particularly examples 73-76, further comprising connecting the proximal end of the third portion of the catheter to a pump.

EXAMPLE 78: The method of any examples herein, particularly example 77, further oxygenating blood received from the inflow lumen in an oxygenator and flowing the oxygenated blood through the outflow lumen into a patient body.

Although several aspects of the invention have been disclosed in the foregoing specification, it is understood by those skilled in the art that many modifications and other aspects of the invention will come to mind to which the invention pertains, having the benefit of the teaching presented in the foregoing description and associated drawings. It is thus understood that the invention is not limited to the specific aspects disclosed hereinabove and that many modifications and other aspects are intended to be included within the scope of the appended claims. Moreover, although specific terms are employed herein, as well as in the claims which follow, they are used only in a generic and descriptive sense and not for the purposes of limiting the described invention nor the claims which follow. We, therefore, claim as our invention all that comes within the scope and spirit of these claims.

We claim:

1. A catheter comprising a first portion having a proximal end and a distal end, a second portion having a proximal end and a distal end and extending between the first portion and a third portion of the catheter, and the third portion having a proximal end and a distal end, the distal end defining a distal end of the catheter, wherein the first and the second portions comprise an outflow lumen;

wherein the third portion comprises an inflow lumen and the outflow lumen;

wherein the first portion has a helical portion having a first length and extending from the distal end of the first portion toward the distal end of the second portion, the helical portion following a helical path having a pitch greater than zero and with a distal end surface of the first portion oriented in a direction away from the catheter; and wherein the catheter is configured to be inserted into a patient body such that the first portion penetrates an atrial septum and extends into a left atrium and the helical portion is positioned within the left atrium to assist with systemic perfusion with oxygenated blood.

2. The catheter of claim 1, wherein the inflow lumen has an elongated tubular body having a proximal end and a distal end and has a first diameter and configured to withdraw oxygen-depleted blood from a patient; and the outflow lumen has an elongated tubular body having a proximal end, a distal end and has a second diameter and configured to deliver oxygen-rich blood to the patient;

wherein the first diameter is greater than the second diameter;

wherein at least a portion of the elongated tubular body of the outflow lumen is disposed within at least a portion of the elongated tubular body of the inflow lumen; and wherein the distal end of the outflow lumen extends beyond the distal end of the inflow lumen.

3. The catheter of claim 2, wherein the elongated tubular body of the outflow lumen is positioned within at least a portion of the elongated tubular body of the inflow lumen such that a center of the outflow lumen is offset of a center of the inflow lumen; or wherein the elongated tubular body of the outflow lumen is positioned within at least a portion of the elongated tubular body of the inflow lumen such that a center of the outflow lumen and a center of the inflow lumen substantially overlap.

4. The catheter of claim 2, wherein the inflow lumen has a first outer layer defining an outer surface of the elongated tubular body of the inflow lumen and a first inner layer defining an inner surface of the elongated tubular body of the inflow lumen; and wherein the outflow lumen has a second outer layer defining an outer surface of the elongated tubular body the outflow lumen and a second inner layer defining an inner surface of the elongated tubular body of the outflow lumen.

5. The catheter of claim 4, wherein the first and/or second outer layer comprises a polymeric material comprising reinforced polyurethane, styrene-based elastomer, polyolefin-based elastomers (POE), polyethylene terephthalate (PET), polytetrafluoroethylene (PTFE), ethylene-vinyl acetate (EVA), fluorinated ethylene propylene (FEP), polyether block amide (PEBAX), or any combination thereof; and/or wherein the first and/or second inner layer comprises a reinforced polyurethane, styrene-based elastomer, polyolefin-based elastomers (POE), polyethylene terephthalate (PET), polytetrafluoroethylene (PTFE), ethylene-vinyl acetate (EVA), fluorinated ethylene propylene (FEP), polyether block amide (PEBAX), or any combination thereof.

6. The catheter of claim 4, wherein the catheter further comprises a reinforcing layer, and wherein the reinforcing layer is substantially encapsulated within the outer layer or wherein the reinforcing layer is disposed between the outer layer and the inner layer.

7. The catheter of claim 1, wherein the proximal end of the first portion extends into the distal end of the second portion and wherein the distal end comprises an outlet of the outflow lumen and/or wherein the proximal end of the second portion extends into the distal end of the third portion and wherein the proximal end of the third portion comprises an outlet of the inflow lumen.

8. The catheter of claim 1, wherein the helical portion of the first portion:

a) the helical path having a pitch less than about 30 mm; and b) has an initial curvature radius from about 2 mm to about 30 mm; and/or c) comprises from about 0.2 to about 1.5 revolutions.

9. The catheter of claim 1, wherein the helical portion of the first portion comprises a first plurality of fenestrations disposed around a circumference of the first portion and along a length of the first portion, the first plurality of fenestrations configured to prevent jet impingement on an endocardial surface of the left atrium and pulmonary veins.

10. The catheter of claim 9, wherein the first portion comprises at least a portion that is substantially free of any fenestrations.

11. The catheter of claim 1, wherein the catheter is configured to be introduced into the patient body such that the first portion of the catheter is positioned within the left atrium and there is substantially no contact with the natural anatomy of the left atrium and/or wherein the distal end of the first portion faces downward to a mitral valve and away from a pulmonary vein.

12. The catheter of claim 1, wherein the first portion comprises a first pressure sensor, wherein the first pressure sensor is disposed within 0 to about 30 mm from the distal end of the second portion towards the first portion.

13. The catheter of claim 1, wherein when the catheter is inserted into the patient body, at least a portion of the second portion is positioned within a right atrium.

14. The catheter of claim 1, wherein the catheter comprises an auxiliary member positioned radially outward of the distal end of the second portion, and an atrial member sized and configured to be inserted into an opening in an atrium septum, wherein the auxiliary member includes a magnet for coupling with a corresponding magnet of the atrial member such that the auxiliary member and the atrial member are configured to removably attach the catheter to the atrium septum.

15. The catheter of claim 14, wherein the auxiliary member comprises a plurality of magnets, wherein at least two of the plurality of magnets have opposite polarity.

16. The catheter of claim 1, wherein the third portion comprises a portion having a second plurality of fenestrations, wherein the portion having the second plurality of fenestrations abuts the distal end of the third portion and has a third length.

17. The catheter of claim 16, wherein the second plurality of fenestrations are disposed circumferentially of the inflow lumen positioned in the third portion and wherein the outflow lumen positioned within the inflow lumen in the third portion is substantially free of any fenestrations.

18. The catheter of claim 16, wherein the catheter is configured to be inserted into the patient body such that at least a portion of the third portion is positioned within the superior vena cava and is substantially free of the second plurality of fenestrations.

19. The catheter of claim 1, wherein the first portion comprises a first pressure sensor and the third portion and/or second portion comprises a second pressure sensor, wherein a flow of oxygenated blood through the outflow lumen is increased or reduced in response to a pressure reading at the first pressure sensor below or above a first set threshold pressure, respectively, wherein the flow of de-oxygenated blood through the inflow lumen is reduced or increased in response to a pressure reading at the second pressure sensor below or above a second set threshold pressure, respectively.

20. The catheter of claim 1, wherein the third portion has at least a portion that is substantially free of any fenestrations.

* * * * *